(12) United States Patent
Weber et al.

(10) Patent No.: US 11,193,101 B2
(45) Date of Patent: *Dec. 7, 2021

(54) METHODS AND APPARATUS FOR SEPARATING LIVE FROM DEAD ORGANISMS IN A SAMPLE

(71) Applicant: Fluid-Screen, Inc., Beverly, MA (US)

(72) Inventors: Monika Weber, Fredericksburg, VA (US); Slawomir Antoszczyk, Somerville, MA (US); Robert Weber, Dorchester, MA (US)

(73) Assignee: Fluid-Screen, Inc., Beverly, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/139,498

(22) Filed: Dec. 31, 2020

(65) Prior Publication Data

US 2021/0139831 A1 May 13, 2021

Related U.S. Application Data

(63) Continuation of application No. PCT/US2020/060412, filed on Nov. 13, 2020.

(Continued)

(51) Int. Cl.
*B01L 3/00* (2006.01)
*C12M 3/06* (2006.01)

(Continued)

(52) U.S. Cl.
CPC ....... *C12M 23/16* (2013.01); *B01L 3/502715* (2013.01); *B01L 3/502753* (2013.01); *B01L 3/502761* (2013.01); *B03C 5/005* (2013.01); *C12Q 1/04* (2013.01); *C12Q 1/06* (2013.01); *C12Q 1/24* (2013.01); *G01N 21/6428* (2013.01); *G01N 21/6458* (2013.01); *G01N 27/44791* (2013.01); *G01N 33/56911* (2013.01); *B01L 2200/027* (2013.01); *B01L 2200/0652* (2013.01); *B01L 2300/0636* (2013.01); *B01L 2300/0645* (2013.01);

(Continued)

(58) Field of Classification Search
None
See application file for complete search history.

(56) References Cited

U.S. PATENT DOCUMENTS 4,970,154 A 11/1990 Chang
5,622,588 A 4/1997 Weber (Continued)

OTHER PUBLICATIONS

Extended European Search Report for European Application No. 15874123.1 dated Aug. 27, 2018.

(Continued)

*Primary Examiner* — Rebecca M Giere
(74) *Attorney, Agent, or Firm* — Wolf, Greenfield & Sacks, P.C.

(57) ABSTRACT

Methods and apparatus for detecting, quantifying, enriching, and/or separating bacterial species in fluid sample are provided. The fluid sample is provided as input to a microfluidic passage of a microfluidic device, wherein the microfluidic device comprises at least one electrode disposed adjacent to the microfluidic passage. The at least one electrode is activated to capture bacteria in the sample using dielectrophoresis, wherein the capture efficiency of bacteria is at least 99%.

20 Claims, 39 Drawing Sheets

Related U.S. Application Data

(60) Provisional application No. 62/934,856, filed on Nov. 13, 2019.

(51) Int. Cl.

| | | |
|---|---|---|
| *G01N 27/447* | (2006.01) | |
| *G01N 33/569* | (2006.01) | |
| *C12Q 1/04* | (2006.01) | |
| *C12Q 1/24* | (2006.01) | |
| *G01N 21/64* | (2006.01) | |
| *B03C 5/00* | (2006.01) | |
| *C12Q 1/06* | (2006.01) | |

(52) U.S. Cl.
CPC .............. *B01L 2300/0816* (2013.01); *B01L 2300/0877* (2013.01); *B01L 2400/0415* (2013.01); *B01L 2400/0424* (2013.01); *B01L 2400/0475* (2013.01); *B01L 2400/082* (2013.01); *G01N 2021/6439* (2013.01); *G01N 2201/062* (2013.01)

(56) References Cited

U.S. PATENT DOCUMENTS

| | | | |
|---|---|---|---|
| 5,814,200 | A | 9/1998 | Pethig et al. |
| 6,071,394 | A | 6/2000 | Cheng et al. |
| 6,264,815 | B1 | 7/2001 | Pethig et al. |
| 6,280,590 | B1 | 8/2001 | Cheng et al. |
| 6,576,459 | B2 | 6/2003 | Miles et al. |
| 6,875,329 | B2 | 4/2005 | Washizu et al. |
| 6,887,362 | B2 | 5/2005 | Huang et al. |
| 6,989,086 | B2 | 1/2006 | Cheng et al. |
| 7,081,192 | B1 | 7/2006 | Wang et al. |
| 7,115,422 | B1 | 10/2006 | Gilton |
| 7,153,648 | B2 | 12/2006 | Jing et al. |
| 7,169,282 | B2 | 1/2007 | Talary et al. |
| 7,198,702 | B1 | 4/2007 | Washizu et al. |
| 7,384,791 | B2 | 6/2008 | Tyvoll et al. |
| 7,390,387 | B2 | 6/2008 | Childers et al. |
| 7,390,388 | B2 | 6/2008 | Childers et al. |
| 7,470,533 | B2 | 12/2008 | Xu et al. |
| 7,534,334 | B1 | 5/2009 | Fiechtner et al. |
| 7,615,762 | B2 | 11/2009 | Satyanarayana et al. |
| 7,658,829 | B2 | 2/2010 | Kanagasabapathi et al. |
| 7,666,289 | B2 | 2/2010 | Simmons et al. |
| 7,686,934 | B2 | 3/2010 | Hodko et al. |
| 7,744,738 | B1 | 6/2010 | Gagnon et al. |
| 8,029,657 | B1 | 10/2011 | Wu |
| 9,120,105 | B2 | 9/2015 | Weber et al. |
| 2002/0036142 | A1 | 3/2002 | Gascoyne et al. |
| 2003/0022393 | A1 | 1/2003 | Seul et al. |
| 2003/0146100 | A1 | 8/2003 | Huang et al. |
| 2004/0011651 | A1 | 1/2004 | Becker et al. |
| 2004/0077074 | A1 | 4/2004 | Ackley et al. |
| 2004/0109793 | A1 | 6/2004 | McNeely et al. |
| 2004/0226819 | A1 | 11/2004 | Talary et al. |
| 2005/0112544 | A1 | 5/2005 | Xu et al. |
| 2005/0158704 | A1 | 7/2005 | Tyvoll et al. |
| 2006/0226012 | A1 | 10/2006 | Kanagasabapathi et al. |
| 2007/0125650 | A1 | 6/2007 | Scurati et al. |
| 2008/0105565 | A1 | 5/2008 | Davalos et al. |
| 2008/0134792 | A1 | 6/2008 | Lee et al. |
| 2008/0221806 | A1 | 9/2008 | Bryant et al. |
| 2009/0020428 | A1 | 1/2009 | Levitan et al. |
| 2009/0294291 | A1 | 12/2009 | Voldman et al. |
| 2009/0304644 | A1 | 12/2009 | Hedrick et al. |
| 2010/0219075 | A1 | 9/2010 | Furusawa |
| 2010/0297608 | A1 | 11/2010 | Stern et al. |
| 2011/0123979 | A1 | 5/2011 | Salmon et al. |
| 2011/0147917 | A1 | 6/2011 | England et al. |
| 2012/0088295 | A1* | 4/2012 | Yasuda ............... C12M 47/04 435/288.7 |
| 2013/0105317 | A1 | 5/2013 | Weber et al. |
| 2013/0292247 | A1 | 11/2013 | Peyrade et al. |
| 2014/0083855 | A1 | 3/2014 | Cheng et al. |
| 2015/0107999 | A1 | 4/2015 | Weber et al. |
| 2015/0283553 | A1 | 10/2015 | Charlot et al. |
| 2015/0318161 | A1 | 11/2015 | Brown et al. |
| 2016/0339423 | A1 | 11/2016 | Quake et al. |
| 2017/0028408 | A1 | 2/2017 | Menachery et al. |
| 2018/0106759 | A1 | 4/2018 | de Oliveira Botelho et al. |
| 2020/0179947 | A1 | 6/2020 | Weber |
| 2021/0039098 | A1 | 2/2021 | Weber et al. |
| 2021/0039099 | A1 | 2/2021 | Weber et al. |
| 2021/0138466 | A1 | 5/2021 | Weber et al. |
| 2021/0146358 | A1 | 5/2021 | Weber et al. |
| 2021/0146359 | A1 | 5/2021 | Weber et al. |

OTHER PUBLICATIONS

International Search Report and Written Opinion for International Application No. PCT/US2017/027659 dated Feb. 12, 2018.

International Search Report and Written Opinion for International Application No. PCT/US2015/65229 dated Feb. 16, 2016.

International Preliminary Report on Patentability for International Application No. PCT/US2015/065229 dated Jul. 6, 2017.

International Preliminary Report on Patentability for International Application No. PCT/US2017/027659 dated Oct. 25, 2018.

Extended European Search Report for European Application No. 17783251.6 dated Oct. 24, 2019.

Invitation to Pay Additional Fees dated Jan. 25, 2021 in connection with International Application No. PCT/US2020/060412.

Beving et al., Dielectric Properties Of Human Blood And Erythrocytes at Radio Frequencies (0.2-10 MHz); Dependence On Cell Volume Fraction and Medium Composition. Eur Biophys J. 1994;23:207-15.

Carstensen, Passive Electrical Properties Of Microorganisms. Biophysical Journal. 1967;7:493-503.

Chang et al., A Continuous Size-Dependent Particle Separator Using A Negative Dielectrophoretic Virtual Pillar Array. Lab Chip. 2008;8:1930-6.

Cheng et al., An Integrated Dielectrophoretic Chip for Continuous Bioparticle Filtering, Focusing, Sorting, Trapping, and Detecting. Biomicrofluidics. 1, 021503. 2007. 15 pages.

Cho et al., Creating, Transporting, Cutting, and Merging Liquid Droplets by Electrowetting-Based Actuation for Digital Microfluidic Circuits. Journal of Microelectromechanical Systems. 2003;12(1):70-80.

Choi et al., 3-Dimensional Electrode Patterning Within A Microfluidic Channel Using Metal ION Implantation. Lab Chip. 2010;10(6):783-8.

Cociancich et al., Insect Defensin, an Inducible Antibacterial Peptide, Forms Voltage-Dependent Channels In Micrococcus Luteus. The Journal Of Biological Chemistry. 1993;268(26);19239-45.

Fritz, Anomalous Diffusion of Erythrocytes in the Presence of Polyvinylpyrrolidone. Biophys. J. Society. 1984;46:219-228.

Ho et al., Rapid heterogeneous liver-cell on-chip patterning via the enhanced field-induced dielectrophoresis trap. Lab on a Chip. 2006;6:724-734. doi: 10.1039/b602036d.

Huang et al., Differences In The AC Electrodynamics Of Viable And Non-Viable Yeast Cells Determined Through Combined Dielectrophoresis And Electrorotation Studies. Phys. Med. Biol. 1992;37(7):1499-517.

Kuczenski et al., Dielectrophoretic Microfluidic Device for the Continuous Sorting of *Escherichia coli* From Blood Cells. Biomicrofluidics. 2011;5:032005. 16 pages.

Lee et al., Electrowetting and Electrowetting-On-Dielectric for Microscale Liquid Handling. Sensors And Actuators A. 95. 2002:259-68.

Markx et al., Dielectrophoretic Characterization and Separation of Micro-Organisms. Microbiology. 1994;140:585-91.

Pethig, Review Article-Dielectrophoresis: Status of the Theory, Technology, and Applications. Biomicrofluidics. 2010;4:022811. 36 pages.

Pohl et al., Separation Of Living And Dead Cells By Dielectrophoresis. Science. Apr. 29, 1966;152:647-9.

(56) References Cited

OTHER PUBLICATIONS

Pohl et al., The Continuous Positive and Negative Dielectrophoresis of Microorganisms. Forum Press, Inc. J. Biol. Phys. 1981;9:67-86.
Pollack et al., Electrowetting-Based Actuation of Droplets for Integrated Microfluidics. Lab Chip. 2002;2:96-101.
Pollack et al., Electrowetting-Based Actuation of Liquid Droplets for Microfluidic Applications. Appl. Phys. Lett. 2000;77(11):1725-6.
Printen et al., Membrane Changes In Lipopolysaccharide-Stimulated Murine B Lymphocytes Associated With Cell Activation. Biochimica et Biophysica Acta. 1993;1148:91-96.
Shah et al., Specific binding and magnetic concentration of CD8+ T-lymphocytes on electrowetting-on-dielectric platform. Biomicrofluidics. 2010;4:044106. 13 pages.
Sher, Dielectrophoresis in Lossy Dielectric Media. Nature. 1968;220:695-6.
Stern et al., Label-free biomarker detection from whole blood. Nature Nanotechnology. 2010;5:138-42.
Stern et al., Label-free Electronic Detection of the Antigen-Specific T-Cell Immune Response. Nano Lett. 2008;8(10):3310-4.
Surowiec et al., Dielectric Properties Of Human B And T Lymphocytes at Frequencies From 20 kHz To 100 MHz. Phys. Med. Biol. 1986;31(1):43-53.
Unni et al., Characterization and Separation of Cryptosporidium and Giardia Cells Using On-Chip Dielectrophoresis. Biomicrofluidics 6, 012805. 2012. 25 pages.
Urdaneta et al., Multiple frequency dielectrophoresis. Electrophoresis. 2007;28:3145-55.
Vacic et al., Multiplexed SOI BioFETs. Biosens. Bioelectron. 2011;28:239-42.
Vahey et al., High-Throughput Cell and Particle Characterization Using Isodielectric Separation. Anal. Chemistry. 2009;81(7):2446-55.
Voldman, Electrical Forces for Microscale Cell Manipulation. Annual Review of Biomedical Engineering. 2006;8:425-54.
Wu, Biased AC Electro-Osmosis for On-Chip Bioparticle Processing. IEEE Transactions on Nanotechnology. 2006;5(2):84-89.
Xie et al., A three-phased circular electrode array for electro-osmotic microfluidic pumping. Microsyst Technol. 2011;17:367-72.
Yang et al., Dielectric Properties of Human Leukocyte Subpopulations Determined By Electrorotation as a Cell Separation Criterion. Biophysical Journal. 1999;76:3307-14.
Yang et al., Differential Analysis Of Human Leukocytes By Dielectrophoretic Field-Flow-Fractionation. Biophysical Journal. 2000;78:2680-89.
International Search Report and Written Opinion dated Apr. 12, 2021 in connection with International Application No. PCT/US2020/060412.

\* cited by examiner

Electric field

| Influent Concentration [CFU/ml] | Effluent Concentration [CFU/ml] | Capture Efficiency (%) |
|---|---|---|
| 8.70E+05 | 0.00E+00 | 100% |
| 4.30E+06 | 6.50E+01 | 99.9985% |
| 6.60E+06 | 3.00E+01 | 99.9995% |
| 1.40E+02 | 0.0E+00 | 100% |

FIG. 12A

| Electric Field | Flow Rate [µl/min] | Influent [CFU/ml] | Effluent [CFU/ml] | Capture Efficiency [%] |
|---|---|---|---|---|
| Settings 1 | 240 | $10^7$ | 0 | 100.000 |
| Settings 1 | 240 | $10^7$ | $10^2$ | 99.990 |
| Settings 1 | 240 | $10^7$ | $10^1$ | 99.9996 |
| Settings 1 | 240 | $10^7$ | 0 | 100.00 |
| Settings 1 | 480 | $10^7$ | $10^5$ | 99.991 |
| Settings 1 | 720 | $10^6$ | $10^4$ | 99.88 |
| Settings 1 | 720 | $10^6$ | $10^3$ | 99.99 |
| Settings 1 | 720 | $10^6$ | $10^2$ | 99.996 |
| Settings 1 | 720 | $10^6$ | $10^3$ | 99.78 |
| Settings 1 | 840 | $10^6$ | $10^3$ | 99.95 |
| Settings 1 | 960 | $10^6$ | $10^4$ | 99.61 |
| Settings 1 | 960 | $10^6$ | $10^3$ | 99.97 |
| Settings 1 | 960 | $10^6$ | $10^3$ | 99.96 |
| Settings 1 | 1080 | $10^6$ | $10^6$ | 85.15 |
| Settings 1 | 1080 | $10^6$ | $10^4$ | 98.62 |

FIG. 12B

| Electric Field | Flow Rate [ul/min] | Influent [CFU/ml] | Effluent [CFU/ml] | Capture Efficiency [%] |
|---|---|---|---|---|
| Settings 2 | 216 | 10^7 | 10^3 | 99.94 |
| Settings 2 | 216 | 10^6 | 10^2 | 99.997 |
| Settings 2 | 216 | 10^6 | 10^3 | 99.79 |
| Settings 2 | 216 | 10^6 | 10^3 | 99.91 |
| Settings 2 | 240 | 10^7 | 10^4 | 99.67 |
| Settings 2 | 264 | 10^7 | 10^4 | 99.57 |
| Settings 2 | 288 | 10^7 | 10^5 | 98.5 |
| Settings 2 | 312 | 10^7 | 10^5 | 98.83 |
| Settings 2 | 336 | 10^6 | 10^5 | 95.71 |
| Settings 2 | 336 | 10^7 | 10^5 | 98.84 |
| Settings 2 | 360 | 10^6 | 10^5 | 95.806 |
| Settings 2 | 384 | 10^6 | 10^5 | 95.269 |
| Settings 2 | 408 | 10^6 | 10^5 | 93.011 |
| Settings 2 | 432 | 10^6 | 10^5 | 92.473 |
| Settings 2 | 456 | 10^6 | 10^5 | 86.559 |
| Settings 2 | 480 | 10^6 | 10^5 | 87.41 |
| Settings 2 | 600 | 10^6 | 10^6 | 82.14 |
| Settings 2 | 720 | 10^6 | 10^6 | 86.455 |
| Settings 2 | 840 | 10^6 | 10^6 | 83.704 |

FIG. 12C

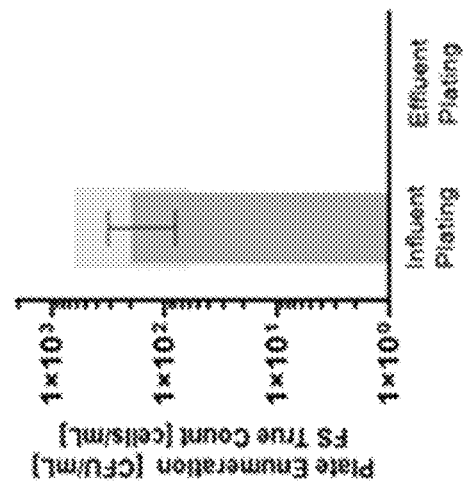
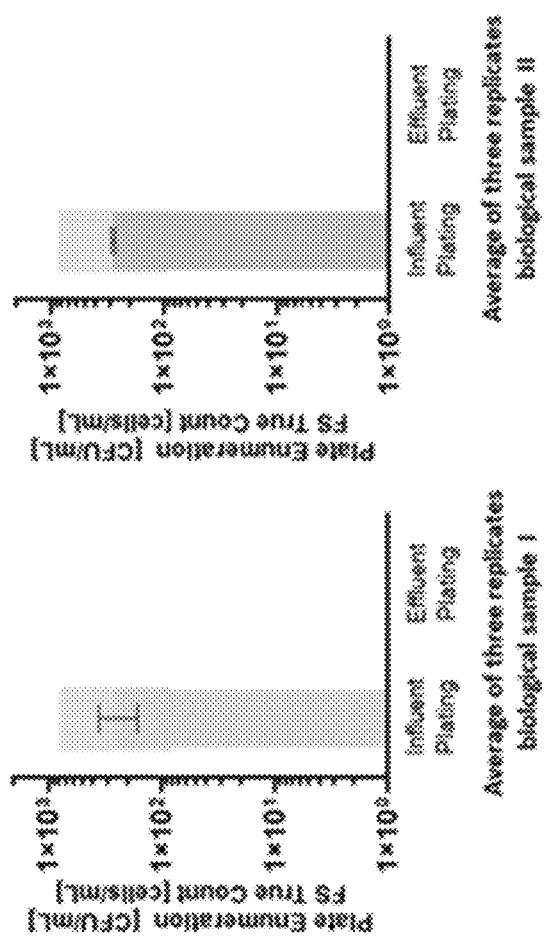
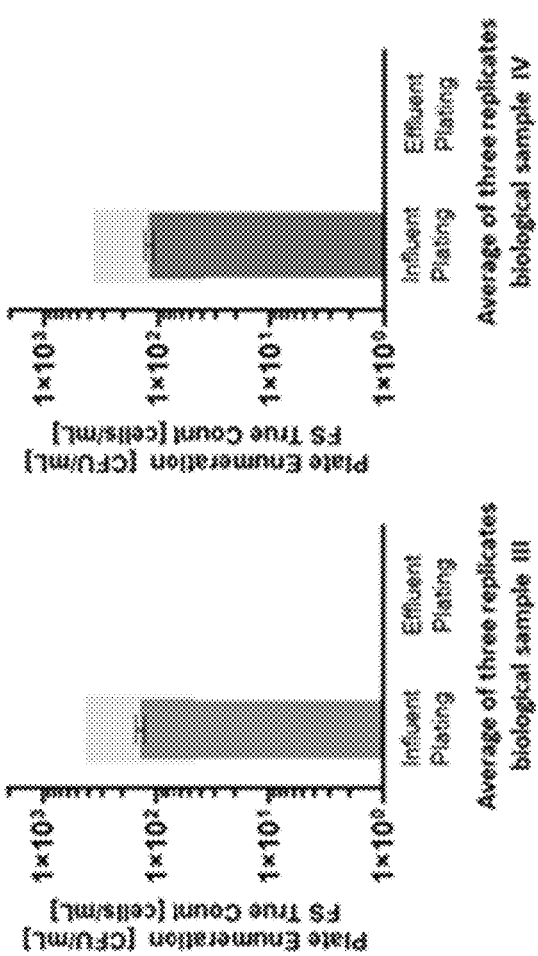
FIG. 13B
FIG. 13A

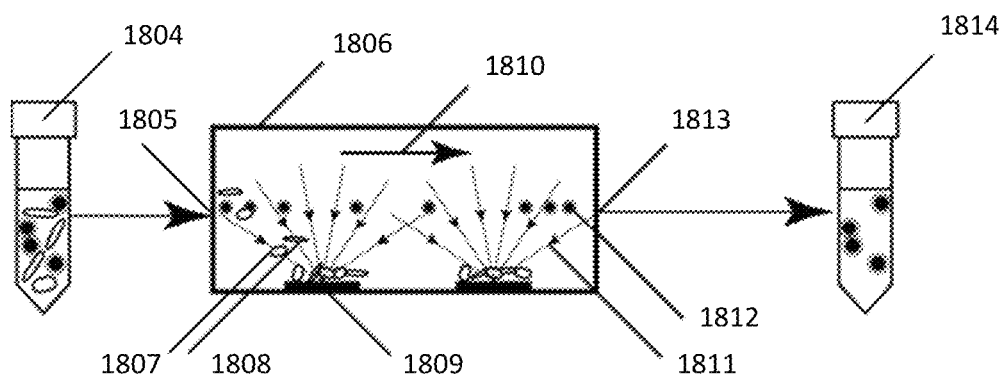
FIG. 18A
FIG. 18B
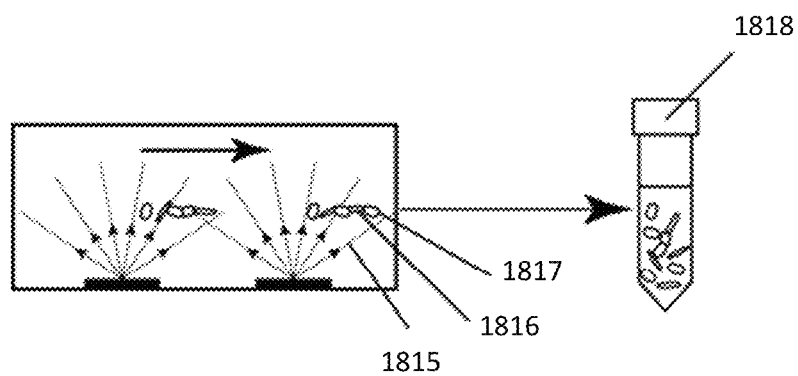
FIG. 18C
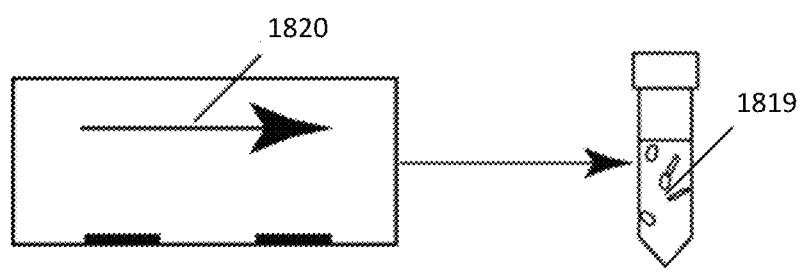
FIG. 18D

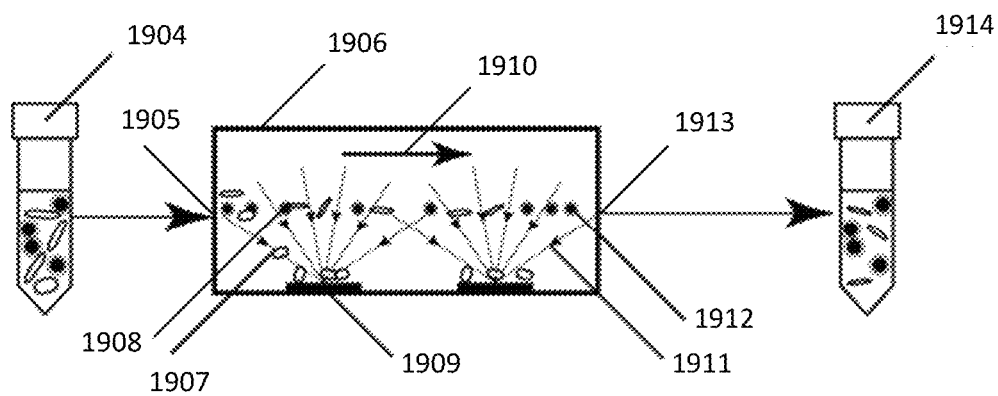
FIG. 19A
FIG. 19B
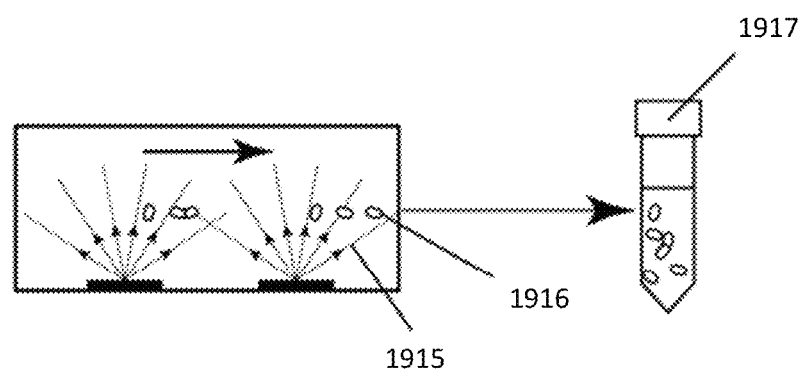
FIG. 19C
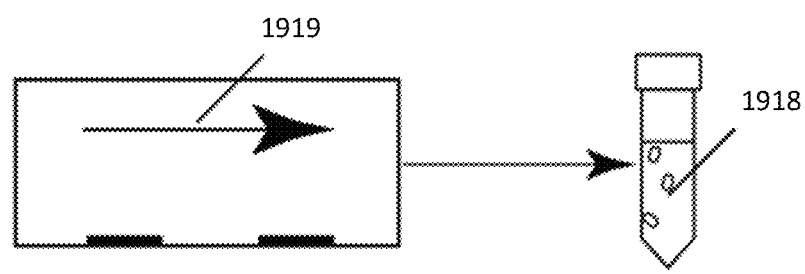
FIG. 19D

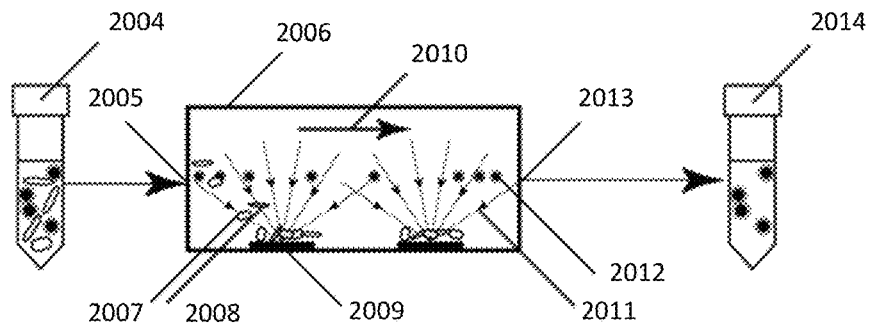
FIG. 20A
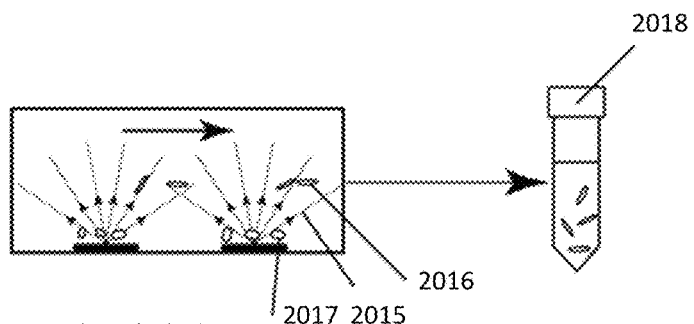
FIG. 20B
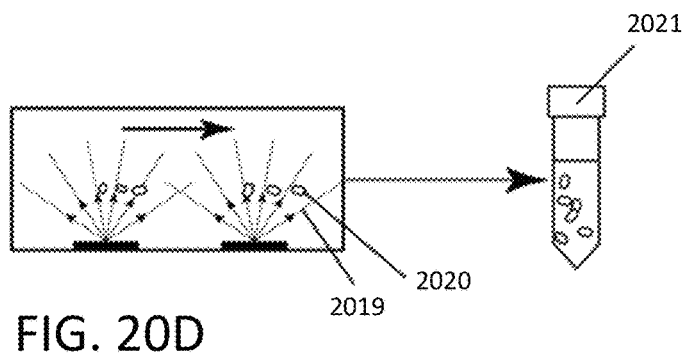
FIG. 20C
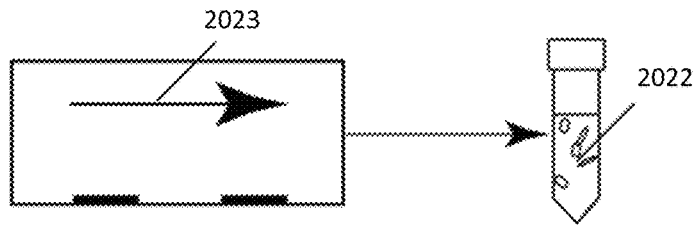
FIG. 20D
FIG. 20E

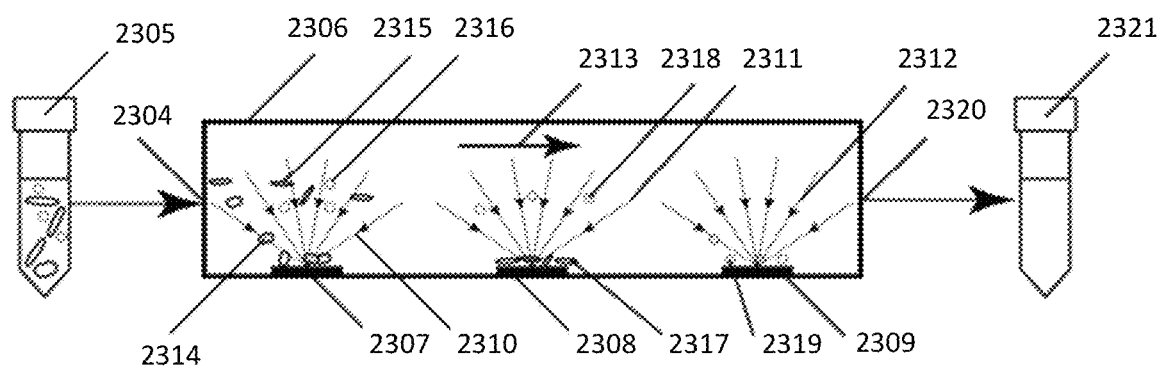
FIG. 23A
FIG. 23B
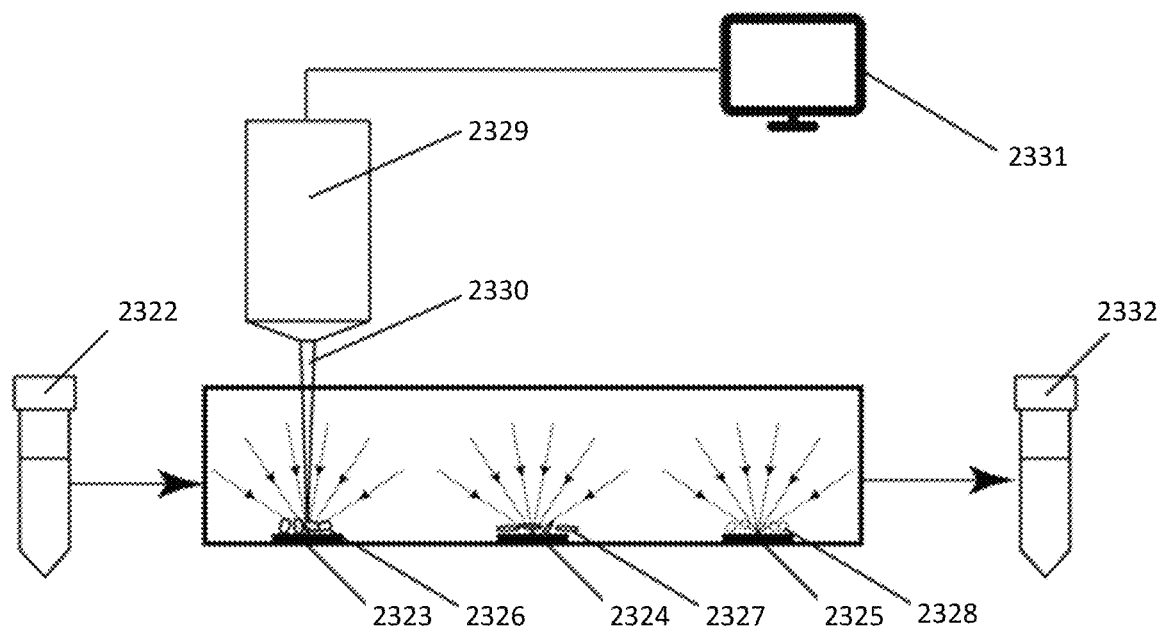
FIG. 23C

○ —— 2401
⊶ —— 2402
∘ —— 2403
✱ —— 2404
FIG. 24A
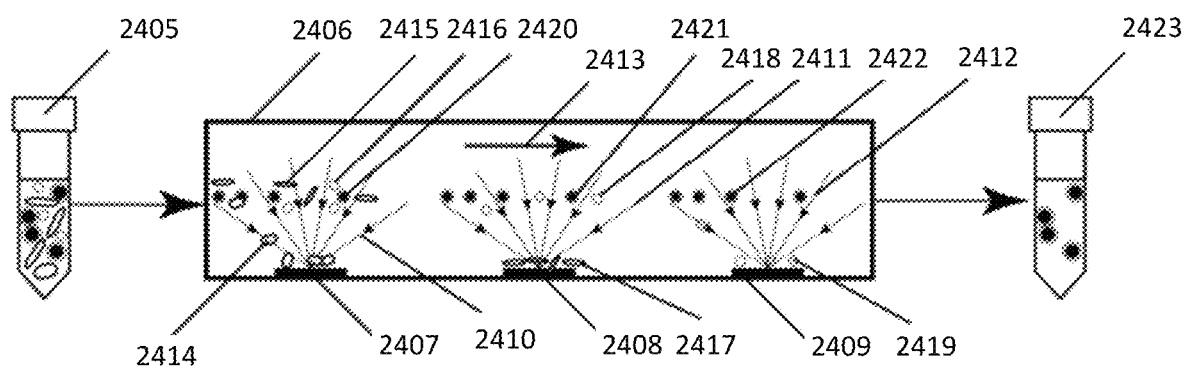
FIG. 24B
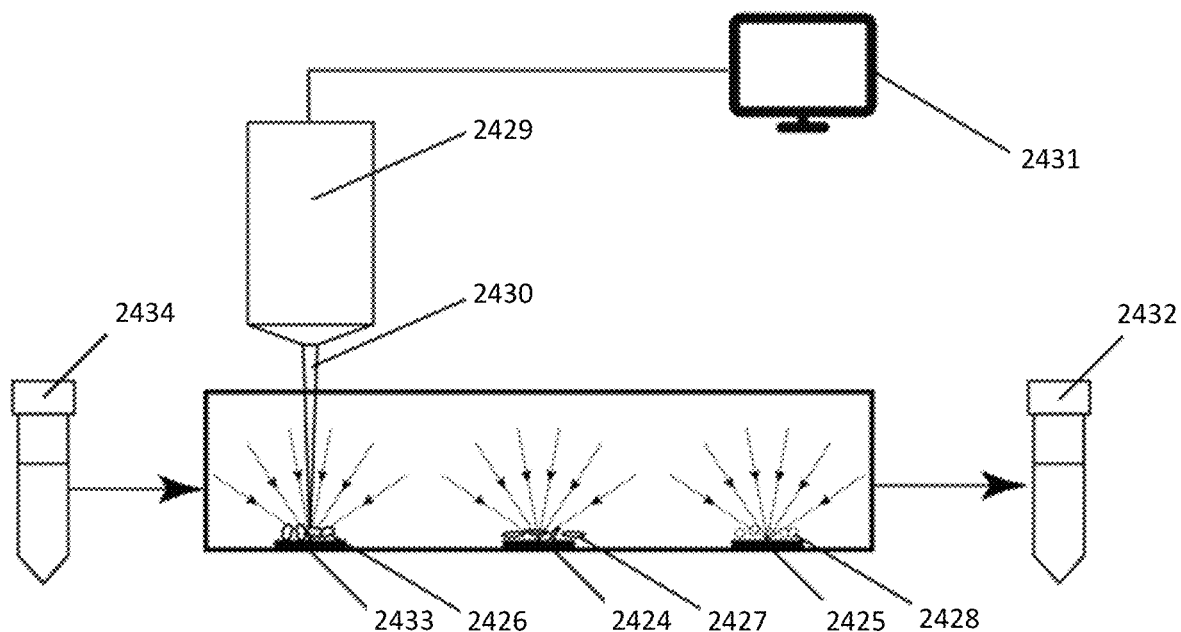
FIG. 24C ○————— 2501
●————— 2502
FIG. 25A
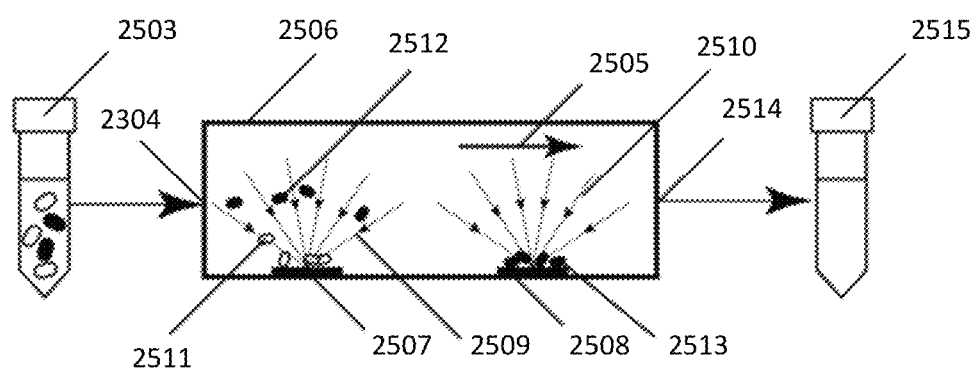
FIG. 25B
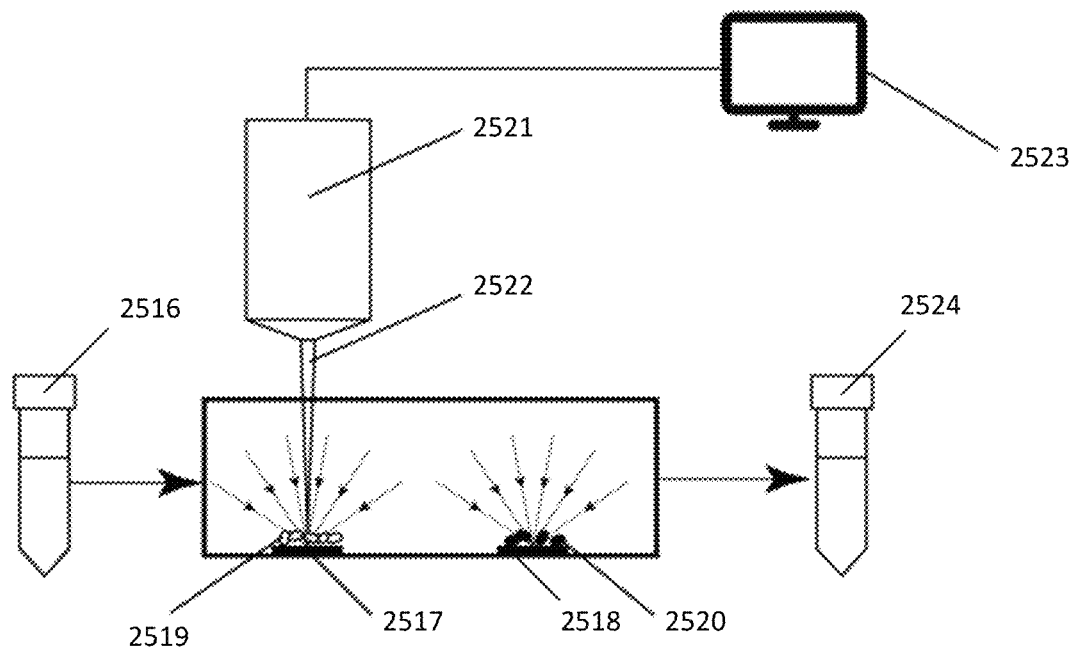
FIG. 25C ○ ———— 2601
● ———— 2602
FIG. 26A
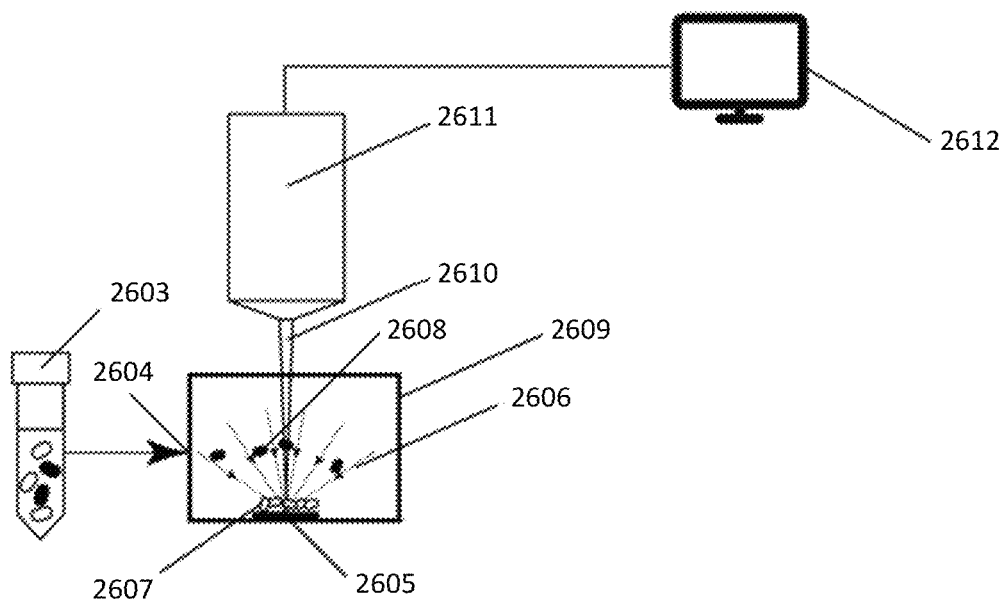
FIG. 26B
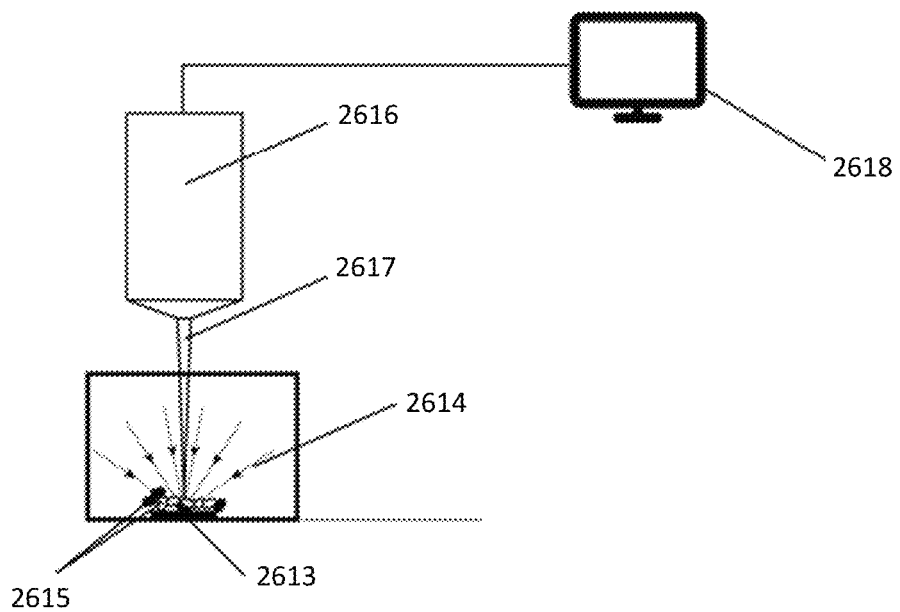
FIG. 26C

| Number of bacteria captured on the Fluid-Screen Sample Sorter | Number of bacteria released from the Fluid-Screen Sample Sorter and cultured | Release & Viability (%) |
|---|---|---|
| 1.18 E+06 CFU | 8.0 E+05 CFU | 68% |

FIG. 30

METHODS AND APPARATUS FOR SEPARATING LIVE FROM DEAD ORGANISMS IN A SAMPLE

RELATED APPLICATIONS

This application is a Continuation of International Patent Application Serial No. PCT/US2020/060412, filed Nov. 13, 2020, entitled "METHODS AND APPARATUS FOR DETECTION OF BACTERIA IN A SAMPLE USING DIELECTROPHORESIS", which claims priority under 35 U.S.C. § 119(e) to U.S. Provisional Application No.: 62/934,856 filed Nov. 13, 2019 and entitled BACTERIAL AND VIRAL TESTING IN 30 MINUTES WITH AN AI ENABLED MICROCHIP," the entire contents of which is incorporated by reference herein.

BACKGROUND

Detection and identification of bacterial and viral pathogens present in cell containing solutions (e.g., blood, urine, CSF), protein containing solutions (e.g., for quality control in pharmaceuticals during manufacturing), analyte extraction from microbiome samples, water, sterile fluids and other fluids is possible by employing isolation on cultural media and metabolic fingerprinting methods. Isozyme analysis, direct colony thin layer chromatography and gel electrophoresis techniques have been successfully applied for the detection of some bacterial pathogens. Immunoassay and nucleic acid-based assays are now widely accepted techniques, providing more sensitive and specific detection and quantification of bacterial pathogens.

Dielectrophoresis (DEP) relates to a force of an electric field gradient on objects having dielectric moments. DEP has shown promise for particle separation, but has not yet been applied in clinical settings. DEP uses a natural or induced dipole to cause a net force on a particle in a region having an electric field gradient. The force depends on the Clausius-Mossotti factor associated with particle.

SUMMARY

Some embodiments relate to a method of high-efficiency capture of bacteria in sample. The method comprises providing the sample as input to a microfluidic passage of a microfluidic device at a predetermined flow rate, wherein the microfluidic device comprises at least one electrode disposed adjacent to the microfluidic passage and activating the at least one electrode to capture bacteria in the sample by the at least one electrode using dielectrophoresis as the sample flows through the microfluidic passage at the predetermined flow rate, wherein the capture efficiency of bacteria is at least 99% when the predetermined flow rate is between 10-960 ul/min.

In at least one aspect, the capture efficiency of bacteria is at least 99% when the predetermined flow rate is between 480-960 ul/min. In at least one aspect, the capture efficiency of bacteria is at least 99% when the predetermined flow rate is between 720-960 ul/min. In at least one aspect, the capture efficiency of bacteria is at least 99% when the predetermined flow rate is between 840-960 ul/min. In at least one aspect, the capture efficiency of bacteria is at least 99.6%. In at least one aspect, the capture efficiency of bacteria is at least 99.9% when the predetermined flow rate is between 240-480 ul/min. In at least one aspect, the capture efficiency of bacteria is at least 99.99% when the predetermined flow rate is 240 ul/min.

In at least one aspect, the method further comprises quantifying, using an optical system, an amount of bacteria captured by the at least one electrode during activation of the at least one electrode. In at least one aspect, quantifying the amount of bacteria comprises capturing one or more images using the optical system, and processing, using at least one computing device, the one or more images to quantify the amount of bacteria. In at least one aspect, quantifying the amount of bacteria comprises counting a number of spots in one or more images captured by the optical system.

In at least one aspect, the method further comprises labeling the bacteria captured on the at least one electrode with a fluorescent dye, exciting the fluorescent dye with at least one light source of the optical system to produce a fluorescent signal, and capturing the fluorescent signal using the optical system, and quantifying the amount of bacteria based, at least in part, on the captured fluorescent signal.

In at least one aspect, the method further comprises collecting effluent fluid at an output of the microfluidic channel, determining an amount of bacteria in the collected effluent fluid, and calculating the capture efficiency based, at least in part, on the determined amount of bacteria in the effluent fluid. In at least one aspect, calculating the capture efficiency based, at least in part, on the determined amount of bacteria in the effluent fluid comprises comparing a concentration of bacteria in the sample provided as input to the microfluidic channel and a concentration of bacteria in the collected effluent fluid.

In at least one aspect, activating the at least one electrode comprises applying an alternating current (AC) voltage to the at least one electrode, wherein the AC voltage has a frequency between 900 Hz and 2 MHz. In at least one aspect, the AC voltage has a frequency of 1 MHz.

In at least one aspect, the at least one electrode comprises a plurality of concentric rings or arcs.

In at least one aspect, the microfluidic passage comprises a microfluidic channel formed in a microfluidic chip.

In at least one aspect, the method further comprises altering a characteristic of an AC voltage provided to activate the at least one electrode, wherein altering the characteristic of the AC voltage causes the capture bacteria to be released from the at least one electrode. In at least one aspect, the characteristic is a frequency of the AC voltage. In at least one aspect, altering the frequency of the AC voltage comprises providing a higher frequency AC voltage to the at least one electrode to apply negative dielectrophoresis to the bacteria. In at least one aspect, the characteristic is an amplitude of the AC voltage.

In at least one aspect, the method further comprises flushing a buffer solution through the microfluidic passage to mechanically release the bacteria from the at least one electrode.

Some embodiments relate to a bacterial detection system. The bacterial detection system comprises a microfluidic device including a microfluidic passage having an inlet and an outlet and at least one electrode disposed adjacent to the microfluidic passage, wherein the at least one electrode when activated, is configured to capture, using dielectrophoresis, bacteria in a sample flowing through the microfluidic passage at a predetermined flow rate, and wherein a capture efficiency of bacteria by the at least one electrode is at least 99% when the predetermined flow rate is between 10-960 ul/min.

In at least one aspect, the bacterial detection system further comprises a first pump coupled to the microfluidic passage, wherein first pump is configured to pump the sample through the microfluidic passage at the predetermined flow rate. In at least one aspect, the first pump is coupled to the outlet of the microfluidic passage. In at least one aspect, the first pump is coupled to the inlet of the microfluidic passage.

In at least one aspect, the bacterial detection system further comprises a second pump coupled to the output of the microfluidic passage, wherein the second pump is configured to pump the sample out of the microfluidic passage.

In at least one aspect, the bacterial detection system further comprises an optical system configured to capture one or more images of the at least one electrode during capture of the bacteria.

In at least one aspect, the bacterial detection system further comprises at least one computing device configured to process the one or more images to quantify an amount of bacteria captured by the at least one electrode.

In at least one aspect, the at least one electrode comprises an array of electrodes arranged in at least one dimension along the microfluidic passage. In at least one aspect, the array of electrodes is arranged in at least two dimensions along the microfluidic passage.

In at least one aspect, the bacterial detection system further comprises a signal generator configured to activate the at least one electrode by applying an alternating current (AC) voltage thereto to generate an electric field. In at least one aspect, the signal generator is configured to apply a same AC voltage to each of the electrodes in the array of electrodes. In at least one aspect, the signal generator is configured to apply a first AC voltage to a first electrode in the array of electrodes and a second AC voltage to a second electrode in the array of electrodes, the first AC voltage and the second AC voltage being different. In at least one aspect, the first AC voltage and the second AC voltage have a different amplitude and/or frequency.

In at least one aspect, the microfluidic passage comprises a microfluidic channel.

In at least one aspect, the microfluidic device comprises a microfluidic chip having a plurality of microfluidic passages configured to process a plurality of samples in parallel.

Some embodiments relate to a method of quantifying bacteria in sample. The method comprises providing, in a first run, a first portion of the sample as input to a microfluidic channel of a microfluidic chip, wherein the microfluidic chip comprises at least one electrode disposed adjacent to the microfluidic channel, activating the at least one electrode to capture bacteria in the first portion of the sample by the at least one electrode using dielectrophoresis, quantifying a first amount of bacteria captured by the at least one electrode during activation of the at least one electrode during the first run, providing, in a second run, a second portion of the sample as input to the microfluidic channel of the microfluidic chip, activating the at least one electrode to capture bacteria in the second portion of the sample by the at least one electrode using dielectrophoresis, and quantifying a second amount of bacteria captured by the at least one electrode during activation of the at least one electrode during the second run, wherein the first amount and second amount are within +/−0.5 log.

In at least one aspect, the method further comprises performing at least ten runs including the first run and the second run and quantifying an amount of bacteria in each of the at least ten runs, wherein an amount of variability in the quantified amount of bacteria across the at least ten runs is less than +/−0.5 log.

Some embodiments relate to a bacterial capture system. The bacterial capture system comprising a microfluidic chip including a microfluidic passage and at least one electrode disposed adjacent to the microfluidic passage, wherein the at least one electrode when activated, is configured to capture, using dielectrophoresis, bacteria in a sample flowing through the microfluidic passage, and wherein a variability of an amount of bacteria captured across multiple runs of the sample flowing through the microfluidic passage is less than +/−0.5 log.

Some embodiments relate to a method for enriching a bacterial species in a sample containing a first target bacterial species and other components. The method comprises providing the sample as input to a microfluidic passage included as a portion of a microfluidic device, wherein the microfluidic passage has at least one electrode disposed adjacent thereto, selecting at least one characteristic of an AC voltage applied to the at least one electrode, wherein the selection of the at least one characteristic is based, at least in part, on the first target bacterial species, applying the AC voltage having the selected at least one characteristic to the at least one electrode to generate an electric field that produces a positive dielectrophoresis force to capture on a surface of the at least one electrode, the first target bacterial species as the sample flows through the microfluidic channel, releasing the captured first target bacterial species from the at least one electrode, and collecting effluent fluid including the captured first target bacterial species, wherein a relative abundance of the first target bacterial species in the effluent fluid is increased compared to the relative abundance of the first target bacterial species in the sample.

In at least one aspect, the other components include a second target bacterial species, and the selection of the at least one characteristic is further based, at least in part, on the second target bacterial species such that both the first and the second target bacterial species are captured on the surface of the at least one electrode as the sample flows through the microfluidic channel when the AC voltage is applied to the at least one electrode.

In at least one aspect, releasing the captured first target bacterial species from the at least one electrode comprises releasing only the first target bacterial species captured on the surface of the at least one electrode.

In at least one aspect, releasing only the first target bacterial species captured on the surface of the at least one electrode comprises adjusting a frequency of the AC voltage applied to the at least one electrode such that a negative dielectrophoresis force is applied to the first target bacterial species to cause the first target bacterial species to be released from the surface of the at least one electrode.

In at least one aspect, adjusting a frequency of the AC voltage comprises increasing the frequency of the AC voltage.

In at least one aspect, collecting effluent fluid including the captured first target bacterial species comprises collecting effluent fluid including only the captured first target bacterial species.

In at least one aspect, the method further comprises releasing all remaining bacterial species captured on the surface of the at least one electrode.

In at least one aspect, releasing all remaining bacterial species captured on the at least one electrode comprises turning deactivating the at least one electrode.

In at least one aspect, releasing all remaining bacterial species captured on the at least one electrode comprises mechanically releasing all remaining bacterial species.

In at least one aspect, mechanically releasing all remaining bacterial species comprises flushing the microfluidic channel with a fluid.

In at least one aspect, the other components include a second target bacterial species, and the selection of the at least one characteristic of the AC voltage is further based, at least in part, on the second target bacterial species such that first target bacterial species is captured on the surface of the at least one electrode as the sample flows through the microfluidic passage and the second target bacterial species is not captured on the surface of the at least one electrode.

In at least one aspect, the at least one characteristic is an amplitude and/or a frequency of the AC voltage.

In at least one aspect, the at least one characteristic comprises the amplitude and the frequency of the AC voltage.

In at least one aspect, the method further comprises pumping the sample through the microfluidic passage.

In at least one aspect, the one or more bacterial species include gram positive bacterial species and gram negative bacterial species, and wherein selecting at least one characteristic of an AC voltage applied to the at least one electrode comprises selecting the at least one characteristic of the AC voltage such than only one of the gram positive bacterial species and the gram negative bacterial species is captured by the at least one electrode.

In at least one aspect, a relative abundance of the first target bacterial species in the effluent fluid is increased at least 20 times compared to the relative abundance of the first target bacterial species in the sample.

In at least one aspect, the sample is a fecal sample or a microbiome sample.

In at least one aspect, the relative abundance of the first target bacterial species in the sample is below a detection limit of DNA sequencing.

In at least one aspect, the first target bacterial species comprises live bacteria and the other components include dead bacteria.

In at least one aspect, quantifying an amount of first target bacterial species captured on the surface of the at least one electrode.

Some embodiments relate to a bacterial enrichment system. The bacterial enrichment system comprising a microfluidic chip including a microfluidic passage and at least one electrode disposed adjacent to the microfluidic passage, a pump coupled to the microfluidic chip and configured to pump a sample from an inlet of the microfluidic passage to an outlet of the microfluidic passage, a signal generator electrically connected to the at least one electrode and configured to generate an AC voltage to drive the at least one electrode to produce an electric field within the microfluidic passage, and a controller configured to control the signal generator to generate the AC voltage having frequency and amplitude characteristics such that when produced, the electric field captures on the surface of the at least one electrode, a target bacterial species in the sample while not capturing one or more other components in a sample as the sample is pumped through the microfluidic channel, and control the signal generator to alter generation of the AC voltage to release the captured target bacterial species in the sample.

In at least one aspect, the pump is coupled to the inlet of the at least one microfluidic channel.

In at least one aspect, the pump is coupled to an outlet of the at least one microfluidic channel.

In at least one aspect, the pump is coupled to the microfluidic chip outside of flow path of the sample.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

Various non-limiting embodiments of the technology will be described with reference to the following figures. It should be appreciated that the figures are not necessarily drawn to scale.

FIG. 12A shows results of an experiment demonstrating the bacteria capture efficiency of a microfluidic system designed in accordance with some embodiments;

FIGS. 12B and 12C show results of an experiment demonstrating the bacteria capture efficiency of a microfluidic system at different flow rates and electric field settings in accordance with some embodiments;

FIGS. 13A and 13B show the results of capture efficiency experiments performed using a microfluidic device designed in accordance with some embodiments;

FIGS. 18A-18D illustrate a process for non-specific (broad spectrum) capture of bacteria in a sample in accordance with some embodiments;

FIGS. 19A-19D illustrate a process for capturing a target bacterial species in a sample including multiple bacterial species in accordance with some embodiments;

FIGS. 20A-20E illustrate a process for non-specific capture and selective release of bacteria in a sample in accordance with some embodiments;

FIGS. 23A-23C illustrate a process for separating multiple bacterial species in a complex sample in accordance with some embodiments;

FIGS. 24A-24C illustrate a process for separating multiple bacterial species and other components in a complex sample in accordance with some embodiments;

FIGS. 25A-25C illustrate a process for separating live from dead bacterial species using multiple electrode systems in accordance with some embodiments;

FIGS. 26A-26C illustrate a process for separating live from dead bacterial species using a single electrode system in accordance with some embodiments;

FIG. 30 shows viability results for bacteria captured and released in accordance with some embodiments;

DETAILED DESCRIPTION

Figure 1:
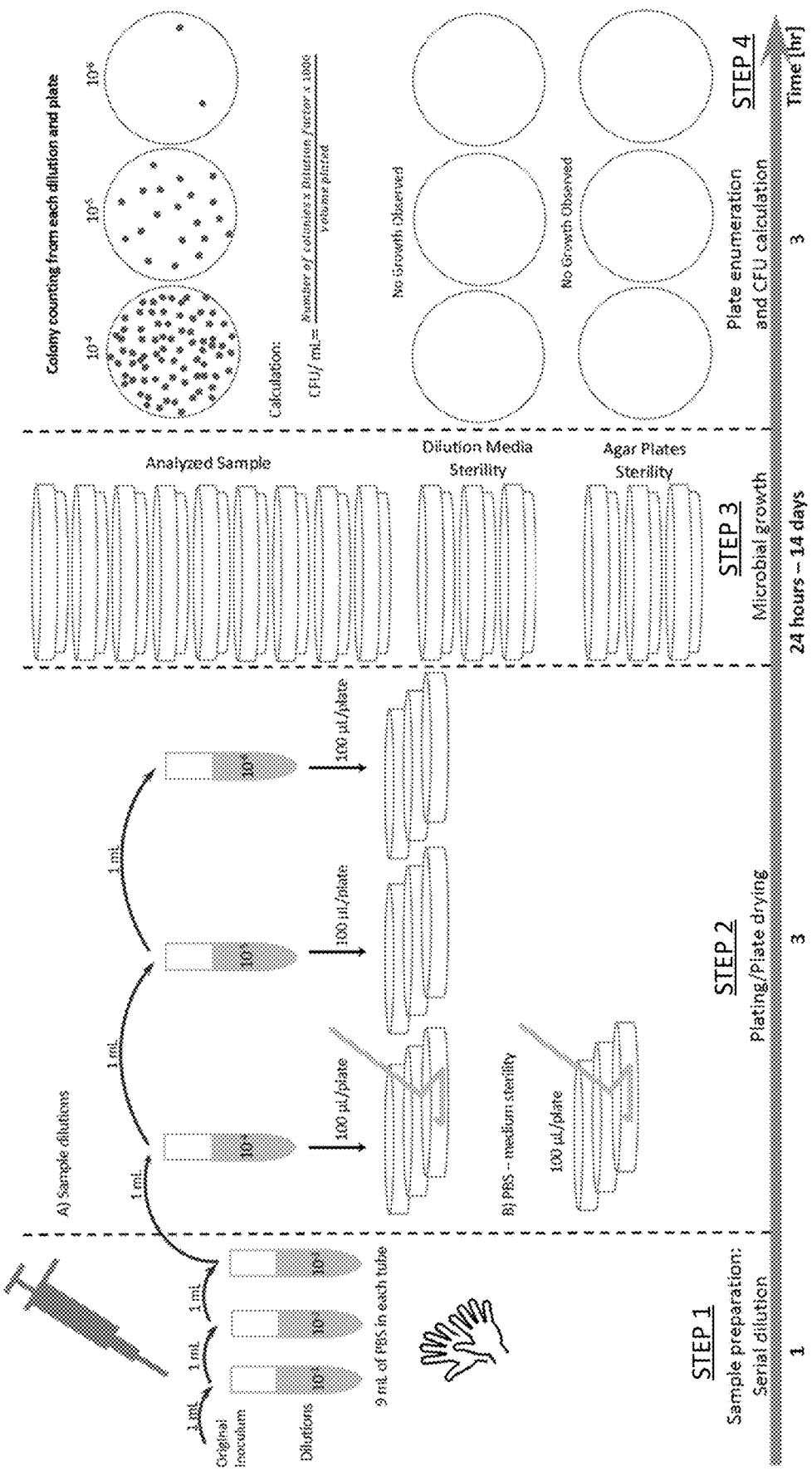
FIG. 1 illustrates a plate counting technique for detecting bacteria in a sample.

Aspects of the technology described herein relate to an apparatus and methods for detecting, separating, quantifying, and/or enriching biological organisms (e.g., bacteria) present in a fluid sample. In particular, the technology described herein provides techniques for rapid detection, separation, purification, and/or quantification of bacteria in a sample using a microfluidic system comprising one or more electrodes configured to generate dielectrophoretic forces that act on the sample.

Microbial (e.g., bacterial, viral and fungal) contamination is a serious and growing global threat to human health and economic development. An example of a conventional technique to assess the presence and degree of microbial contamination in a sample is the Plate Counting Method (PCM), which is shown schematically in FIG. 1. As shown, PCM typically includes at least four steps. In step 1, a sample to be analyzed is manually placed in each of multiple test tubes, and the sample in each test tube is diluted to a desired concentration using a buffer solution. In step 2, the diluted samples are plated onto petri dishes containing agar media. Petri dishes including dilution media only (i.e., without the sample) are also plated for use as controls for comparison against the plated diluted samples. In step 3, the plurality of plated samples, the dilution media plates, and empty agar plates are cultured for 24 hours to 14 days to enable microbial particles to grow on the media within the petri dishes. In step 4, the number of bacterial colonies on each of the plates cultured in step 3 is determined, for example, using a microscope.

PCM is routinely used in medical, pharmacological and food industries to identify bacterial contamination. However, PCM is slow, only moderately sensitive, labor intensive and prone to human errors. For instance, as shown, the entire PCM process takes 1-14 days, includes several manual steps in which human intervention is needed, and requires a large number of plated samples at different dilutions and controls. There is therefore a need for new technologies that allow for faster, more sensitive and more reliable assessment of microbial contamination.

Dielectrophoresis (DEP) has shown promise for particle separation; however, it has not yet been applied in clinical settings. For instance, only small sample volumes with unrealistically high bacterial concentrations on the order of $10^3$-$10^7$ CFU/mL have been processed, which limits the applicability of DEP microbial capture methods. DEP particle separation has been achieved only to a limited extent and the separation is restricted to specific cell types, (e.g., separation of *Escherichia coli* from *Bacillus subtilis*). Unfortunately, separation of small cells (~1 μm in diameter, the size of many pathogenic bacteria) using DEP has been notoriously difficult. For instance, small bacterial particles undergo significant Brownian motion that adds a time dependent variation in their position, and thus the specificity of separation decreases for small cells, which has previously been thought to limit the applicability of the DEP technique for detecting and/or separating bacteria in a sample.

Some embodiments of the technology described herein relate to a novel DEP bacterial capture and separation technique (also referred to herein as "Fluid-Screen" or "FS") that addresses at least some of the limitations of prior DEP techniques. As described in further detail below, the efficiency of bacterial capture using the techniques described herein are measured and compared to bacterial capture using the standard PCM technique.

Although capture and separation of bacteria from a sample is described herein, it should be appreciated that biological particles other than bacteria, for example, different cells, yeast, mold, fungus, viruses, etc. can also be detected, quantified, separated, and/or enriched using one or more of the techniques described herein. Indeed, the technology described herein has been shown to effectively capture, detect, quantify, and separate a wide range of diverse microorganisms including, but not limited to, both Gram (−) and Gram (+) bacteria, multiple bacterial morphologies, both individual bacteria and cell aggregates, yeasts or molds (including conidia, conidiophores and hyphae), and viruses. Table 1 below illustrates a summary of some microorganisms that have been successfully captured and detected using the techniques described herein.

TABLE 1

Example microorganisms detected using the techniques described herein

| | Microorganism Differentiation | Media [Dilution] | Media pH | PBS [Dilution] | PBS pH | Microfluidic Chip Type | Stain |
|---|---|---|---|---|---|---|---|
| E. coli | Gram (−) | CHO, 1:100 | 7.09 | 1:1000 | 7.4 | Static | Sybr Green |
| B. subtilis | Gram (+) | CHO, 1:100 | 7.09 | 1:1000 | 7.4 | Static | Sybr Green |
| P. aeruginosa | Gram (−) | CHO, 1:100 | 7.09 | 1:1000 | 7.4 | Static | Sybr Green |
| S. aureus | Gram (+) | CHO, 1:100 | 7.09 | 1:1000 | 7.4 | Static | Sybr Green |
| C. albicans | Yeast | CHO, 1:100 | 7.09 | 1:1000 | 7.4 | Static | Sybr Green |
| A. brosiliensis | Mold | CHO, 1:100 | 7.09 | 1:1000 | 7.4 | Static | N/A |

Figures 32A, 32B:
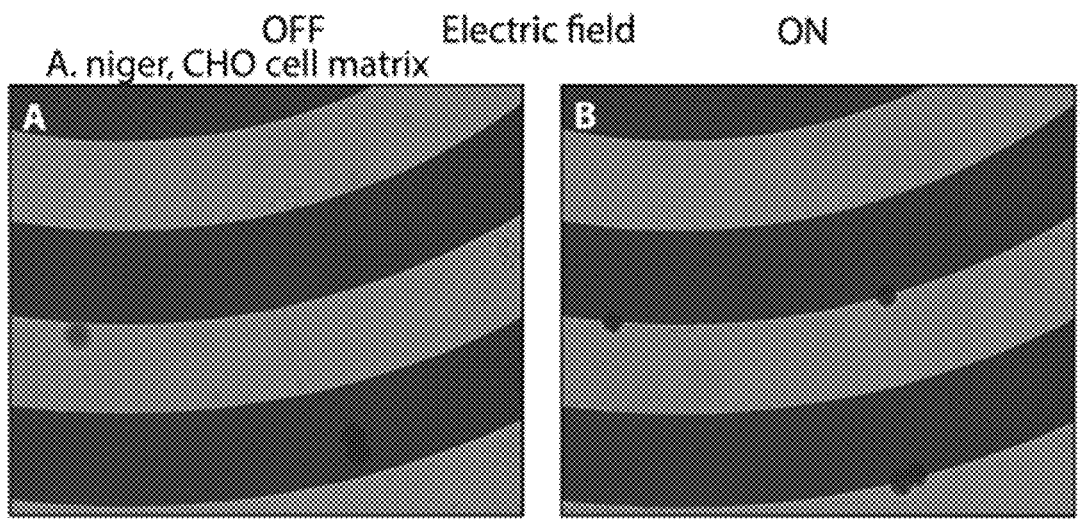
FIGS. 32A-32F illustrates capture of fungus, yeast, and bacteria, respectively in accordance with some embodiments.
Figures 32C, 32D:
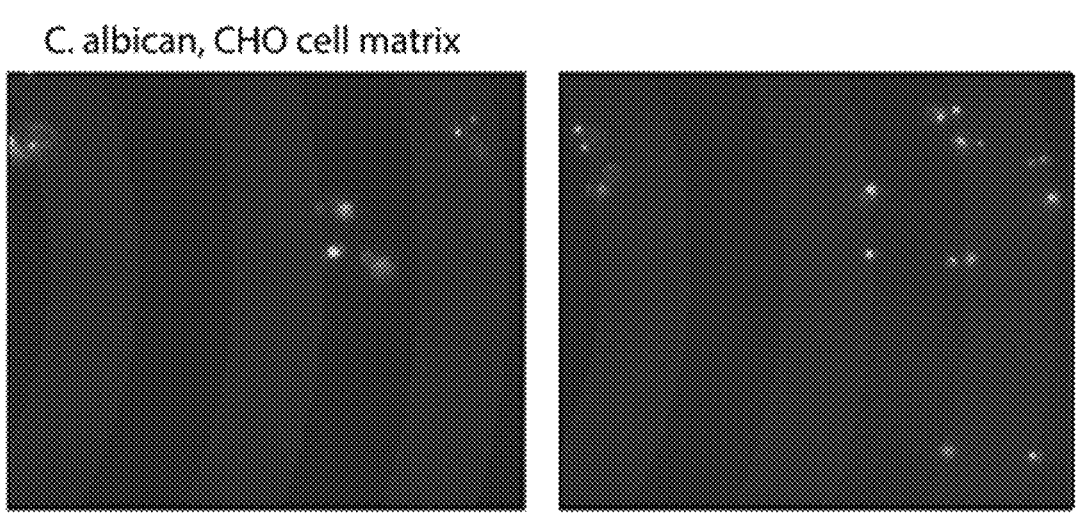
Figures 32E, 32F:
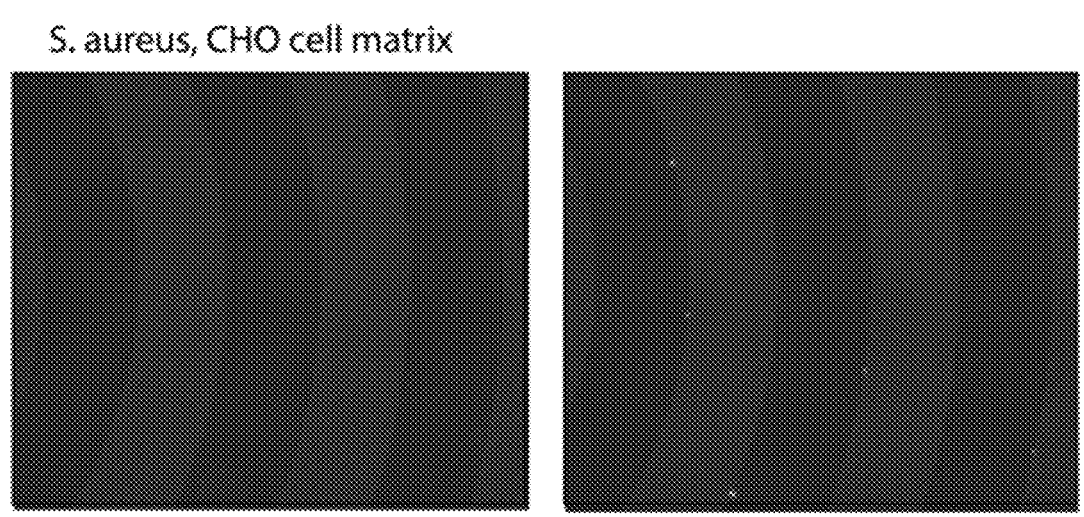

A microfluidic system designed in accordance with some embodiments may also be used to capture yeast, mold, and bacteria in a Chinese hamster ovary (CHO) cell matrix, examples of which are shown in FIGS. 32A-E. FIGS. 32A and 32B show the response of the fungus *Aspergillus niger* when the electric field is off (FIG. 32A) resulting in no capture and when the electric field is on (FIG. 32B) resulting in capture on the edges of the electrode. FIGS. 32C and 32D show the response of the yeast *C. albicans* when the electric field is off (FIG. 32C) resulting in no capture and when the electric field is on (FIG. 32D) resulting in capture on the edges of the electrode. FIGS. 32E and 32F show the response of the bacteria *S. aureus* when the electric field is off (FIG. 32E) resulting in no capture and when the electric field is on (FIG. 32F) resulting in capture on the edges of the electrode.

In accordance with some embodiments, a fluid sample containing bacteria is processed in a microfluidic system. For example, in a microfluidic device, the sample may be subjected to DEP forces and/or electroosmosis (EO) to enable detection, separation, purification and/or quantification of bacterial particles in the fluid sample. Examples of a microfluidic system suitable for use in accordance with the techniques described herein, include the Fluid-Screen Microfluidic System, aspects of which are described in U.S. patent application Ser. No. 16/093,883 under Attorney Docket No. F0777.70000US03 and titled "ANALYTE DETECTION METHODS AND APPARATUS USING DIELECTROPHORESIS AND ELECTROOSMOSIS," filed on Oct. 15, 2018, and U.S. patent application Ser. No. 14/582,525 under Attorney Docket No. F0777.70002US01 and titled "APPARATUS FOR PATHOGEN DETECTION" filed on Dec. 24, 2014, each of which is hereby incorporated by reference in its entirety.

Figure 2:
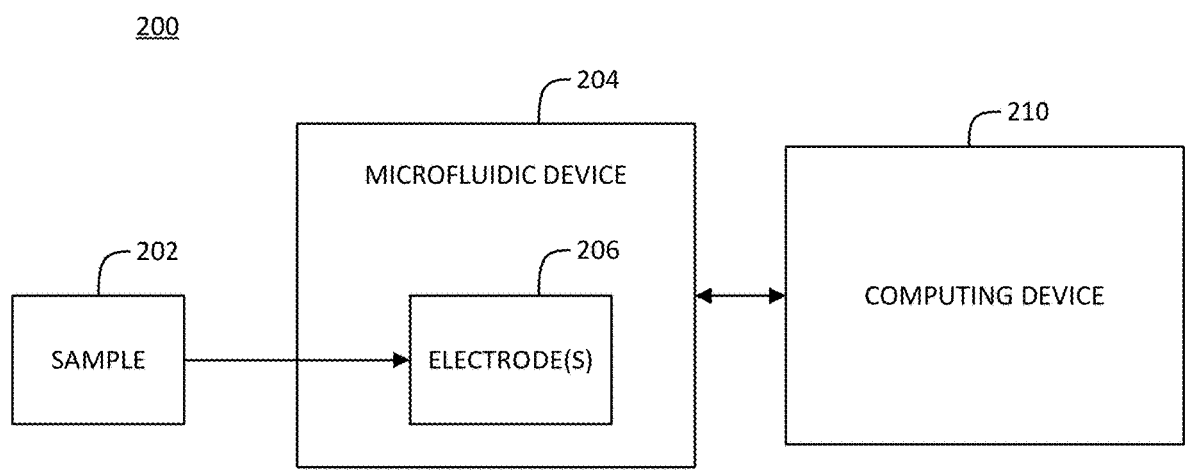
FIG. 2 illustrates a system for detecting the presence of bacteria in a sample, according to some embodiments.

FIG. 2 illustrates an example system for detecting bacteria in a sample, in accordance with some embodiments. As shown in FIG. 2, the system 200 comprises a microfluidic device 204 in communication with a computing device 210.

Figure 3:
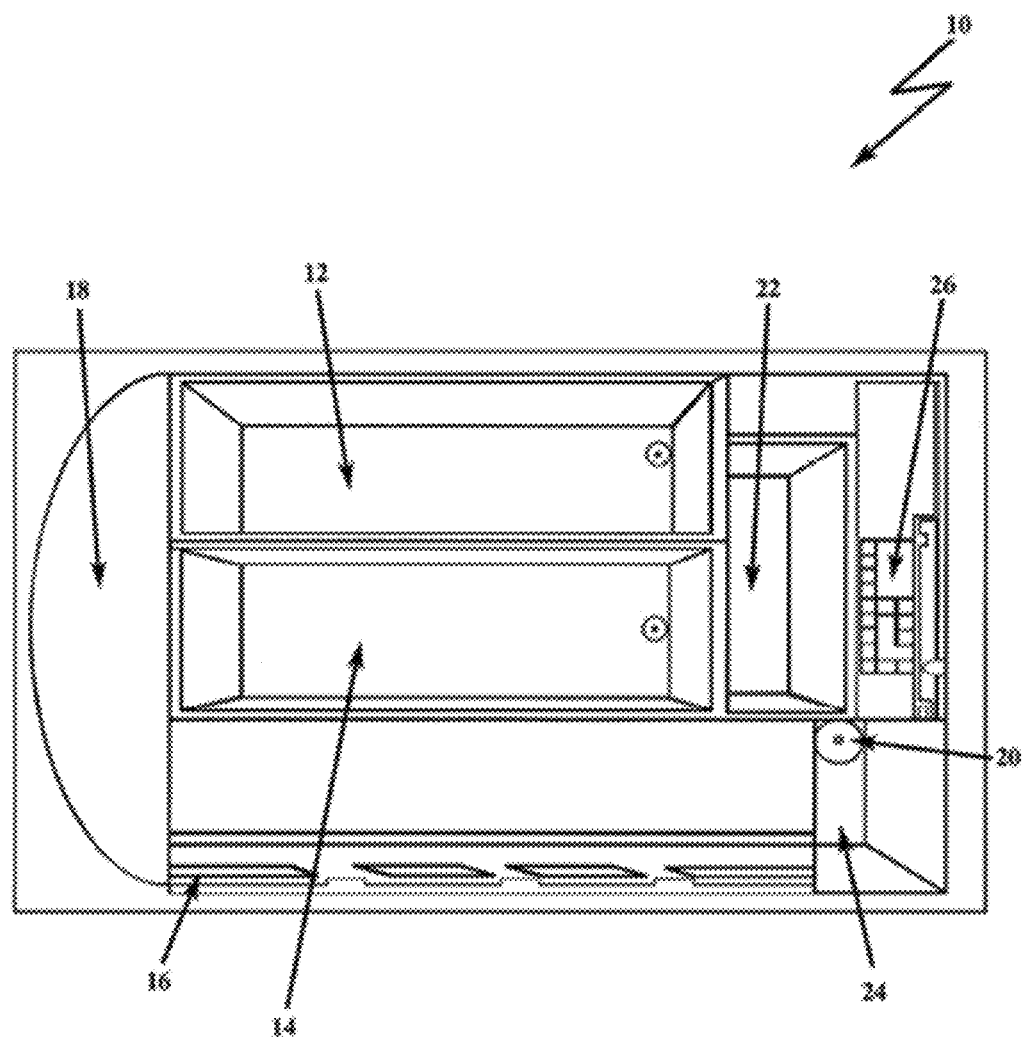
FIG. 3 illustrates a microfluidic system for detecting the presence of bacteria in a sample, according to some embodiments.

The microfluidic device 204 may be any suitable device, examples of which are provided herein, in particular, with respect to FIG. 3. In some embodiments, microfluidic device 204 comprises a microfluidic chip having one or more passages (e.g., microfluidic channels or chambers) through which a fluid sample 202 is provided for analysis. Although the term "microfluidic channel" or simply "channel" is used herein to describe a passage through which fluid flows through microfluidic device 204, it should be appreciated that a fluid passage having any suitable dimensions may be used as said channel, and embodiments are not limited in this respect. Microfluidic device 204 may comprise a single channel or multiple channels configured to receive a single sample 202 (e.g., to perform different analyses on the sample) or multiple channels configured to receive different samples for analysis. In embodiments having multiple channels, the microfluidic device may be configured to process the single sample or multiple samples in parallel (e.g., at the same or substantially the same time).

As described herein, sample 202 may include any fluid containing bacteria or other microorganism of interest. In some embodiments, the sample comprises a biological fluid such as saliva, urine, blood, water, any other fluid such as an environmental sample or potentially contaminated fluid, protein matrices, mammalian cell culture, bacterial culture, growth media, active pharmaceutical ingredients, enzyme products, or substances used in biomanufacturing, etc.

As shown, microfluidic device 204 includes at least one electrode 206. The at least one electrode 206 may be configured to receive one or more voltages to generate positive and/or negative dielectrophoresis (DEP) force(s)

that act on a sample arranged proximate to the at least one electrode. In some embodiments, the at least one electrode 206 may be configured to receive one or more voltages (e.g., one or more AC voltages) to generate at least one dielectrophoresis force or electroosmotic (EO) force that acts on the sample. The at least one DEP and/or EO force may cause certain components of the sample to move relative to (e.g., be attracted to or repulsed from) a surface of the at least one electrode 206. For example, in the absence of an electric field, bacteria and other components of the sample 202 may move freely relative to the surface of the electrode. In the presence of the electric field at least some components (e.g., bacteria) in the sample may be attracted to the electrode surface.

The small size of bacteria presents an obstacle to optical observation and quantification of bacteria in the sample. The inventors have recognized that activation of the at least one electrode 206 results in an electric field that may be used to selectively trap bacteria on the surface of the electrode(s). When used with an optical detection system, capturing bacteria on the surface of the electrode(s) may prevent the bacteria from moving in and out of focus of the optical device to enable real-time bacteria detection and quantification, a process referred to herein as "on-chip quantification."

The electric field used to capture the bacteria concentrates the bacteria, which enables imaging with fluorescence microcopy or another optical detection technique. Accordingly, bacterial capture using the techniques described herein allows for detection and quantification of bacteria at significantly lower limits compared to some conventional methods, such as the PCM technique described in connection with FIG. 1. The ability to detect and/or quantify bacteria in a sample, even in small amounts, may be useful in applications including, but not limited to, biomanufacturing, gene therapy, analysis of patient samples, vaccine development and/or biothreat detection.

For example, the at least one DEP and/or EO forces acting on the sample may cause bacteria to separate from other components of the sample (e.g., via positive DEP). Bacteria in the sample may be attracted to the surface of the at least one electrode 206 allowing for enhanced detection and/or quantification, despite the small size and/or small amount of the bacteria in the sample. Although, microfluidic device 204 is illustrated as having a single electrode, it should be understood that in some embodiments, microfluidic device 204 comprises multiple electrodes arranged in any suitable configuration. The at least one electrode(s) 206 may have any suitable shape. Non-limiting examples of electrode shapes and designs that may be used in accordance with some embodiments are further described below in connection with FIGS. 7A-7F and FIGS. 33-37.

System 200 may further comprise a computing device 210 configured to control one or more aspects of microfluidic device 204. For example, computing device 210 may be configured to direct the sample 202 into a channel of the microfluidic device. In some embodiments, computing device 210 is configured to control the at least one electrode 206 to generate the at least one DEP force and/or EO force acting on the sample 202. In some embodiments, computing device 210 may cause one or more components of the microfluidic system (e.g., an optical device) to perform one or more of detection, quantification, separation, and/or purification of the bacteria or other microorganisms in the sample. Non-limiting examples of a computing device 210 that may be used in accordance with some embodiments are further described herein, for example, with respect to FIG. 31.

An example microfluidic device configured to process a sample in accordance with the techniques described herein is shown in FIG. 3, which is reproduced from U.S. patent application Ser. No. 13/664,967, now U.S. Pat. No. 9,120,105, entitled "ELECTRONIC DEVICE FOR PATHOGEN DETECTION" filed on Oct. 31, 2012, which is hereby incorporated by reference in its entirety. Device 10 in FIG. 3 comprises a sample chamber 12 and a chamber 14 containing a reference solution which may in some embodiments include a separator which purifies the reference solution from contaminants. In some embodiments, device 10 may not include the chamber containing the reference solution.

Chambers 12 and 14 are connected by micropumps adapted to force either fluid around the passage 18 and through separator passage 16. First, the sample comprising bacteria and other components may be pumped through the separator. The separator includes one or more electrodes configured to apply a dielectrophoretic, electroosmotic, and/or other AC kinetic force on the components of the sample, which results in bacteria in the sample being selectively attracted toward the bottom of the figure. The other components not attracted toward the electrode(s) may be trapped in chamber 22, while the bacteria are drawn into the holding chamber 24 by concentrator 20, which the separator and the condenser may in some embodiments comprise a set of coaxial interdigitating rings or arches having independent voltages. Once the bacteria are held by the concentrator 20, the buffer solution may be pumped from chamber 12 around the bend 18 and through the separator passage 16 to flush the chamber 24, effectively changing the medium in which the bacteria are found and eliminating any residual unfiltered elements. The bacteria can then be released from concentrator 20 (by removing the electric field) and may be drawn towards analyzer array 26 (which itself may be provided with one or more electrodes adapted to attract the bacteria thereto).

Device 10 uses dielectrophoresis for purposes of separating bacteria from other components of a sample. Dielectrophoresis uses a natural or induced dipole to cause a net force on a particle in a region having an electric field gradient.

$$F = 2\pi\varepsilon_m R^3 Re[\underline{CM}(\omega) \cdot \nabla \underline{E}^2(r,\omega)]$$

This force depends on the Clausius-Mossotti factor CM(w) defined by $$CM(\omega) = \frac{\epsilon_p^o - \epsilon_m^o}{\epsilon_p^o + 2\epsilon_m^o}$$

where $\epsilon^o$ is the complex permittivity, $$\epsilon^o = \frac{\sigma}{i\omega}.$$

In some embodiments, the values for σ and ω are chosen to reach a maximal separation force between the bacteria or other analyte to be separated and other components in the solution being processed by the device. This can be accomplished by compiling knowledge concerning both the bacteria and other components to be separated. The differential response of the bacteria and other components of a sample to an applied electric field can be inspected for its extrema which will show the greatest differential response tending to separate the bacteria from the other components. The frequency of the applied AC voltage used for separation may be chosen, while the conductivity of the solution can be controlled by titration of a known amount of solution of known conductivity (or equivalently, salinity). Alternatively, a feedback technique may be used by measuring the conductivity of the solution and adding saline or deionized water (for instance) until a desired conductivity is reached. A reference measurement may be used for quality control and identification of the solution. A differential measurement of the control signal (no contamination) with an actual signal (with labeled contaminants) may be used. Conductivity and complex permittivity measurements may be implemented at multiple stages in the devices for quality control of fluid mixing and feedback adjusting the mixing rate. As will be appreciated by one skilled in the art, such analysis of a differential response may be performed for any pair of species in question in a given sample.

Figure 4:
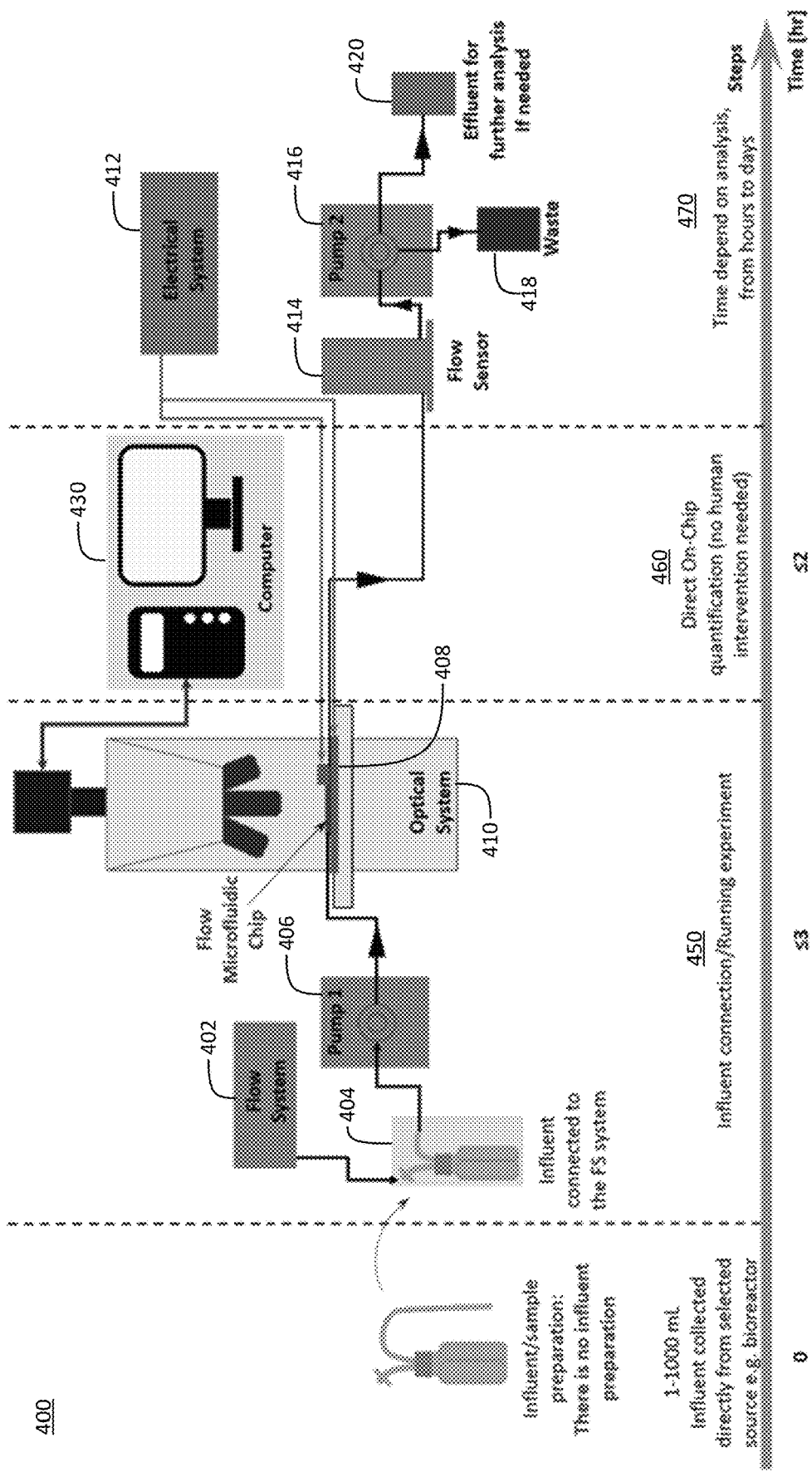
FIG. 4 illustrates a flow-based system for detecting the presence of bacteria in a fluid sample, according to some embodiments.

FIG. 4 illustrates an example system 400 for detecting the presence of bacteria in a sample, in accordance with some embodiments. System 400 includes microfluidic device 408 (e.g., a microfluidic chip) that includes one or more electrodes for generating DEP and/or EO forces that act on a sample 404 provided as input to the system. Sample 404 may contain bacteria for which detection, separation, purification, and/or quantification may be performed. The one or more electrodes may be arranged in any suitable configuration within the microfluidic device 408. For instance, in embodiments that include multiple electrodes the electrodes may be arranged in one-dimension along the flow direction of the fluid, perpendicular to fluid flow direction or on a diagonal relative to the fluid flow direction. In some embodiments, a multidimensional (e.g., 2-dimensional, 3-dimensional) array of electrodes may be used. For instance, a dense array of electrodes arranged both along the direction of fluid flow and perpendicular to the direction of fluid flow may be used.

As shown in FIG. 4, a flow system 402 is provided. The flow system 402 may provide a solution for transporting the sample 404 to the microfluidic device 408. A first pump 406 may be used to pump the solution and the sample 404 to the microfluidic device 408 at a predetermined flow rate. First pump 406 may be of any suitable type. In some embodiments, as further described herein, first pump 406 is omitted, and sample 404 is manually loaded (e.g., using a pipette) as input to one or more channels of microfluidic device 408.

Microfluidic device 408 is configured to receive sample 404 for processing.

Microfluidic device 408 may include one or more channels through which the sample 404 flows. The one or more channels may include at least one electrode formed therein or adjacent thereto. For instance, the at least one electrode may be formed within a channel. The at least one electrode, when activated, is configured to generate an electric field that acts on the sample 404 as it flows through the one or more channels. An electrical system 412 (e.g., a signal generator or controller) is configured to provide one or more voltages to the at least one electrode of the microfluidic device 408 to tune the properties of the electric field for capture of a particular microorganism or microorganisms of interest. Further aspects of the electrical system 412, including example protocols for operating the microfluidic device 408 are provided herein.

An optical system 410 may be provided to facilitate analysis of the sample 404 by performing on-chip quantification. For example, the optical system 410 may comprise one or more optical sensors for viewing and/or imaging the sample. The optical sensor(s) may provide for enhanced detection and/or quantification of the bacteria and/or the other components of the sample 404 relative to detection and quantification techniques that require separate culturing of captured bacteria or an effluent sample from the device. Any suitable optical detector may be used. In some embodiments, the optical sensor(s) comprises a digital camera. In some embodiments, the optical sensor(s) comprises electronic sensors including CMOS compatible technology. In some embodiments, the optical sensor(s) comprise fiber optics. However, any suitable optical sensor(s) may be used. In some embodiments, bacteria in the sample are stained with a fluorescent dye and the optical system 410 is configured to perform fluorescence microscopy of captured stained bacteria. In some embodiments, optical system 410 is configured to capture one or more images of the at least one electrode while the sample is flowing through the microfluidic device 408. In some embodiments, the detector comprises nanowire and/or nanoribbon sensors.

System 400 also includes computer 430 configured to control an operation of optical system 410 and/or to receive images from optical system 410 and to perform processing on the received images (e.g., to count a number of bacteria trapped by the microfluidic device 408). In some embodiments, the received images are analyzed to determine the number of bacteria captured by the at least one electrode. For instance, bacteria may be identified in the received images as spots (e.g., fluorescent spots) located on the edges of the electrodes. In this way a captured target bacterial species may be differentiated from other components in the sample that are not captured and may appear as floating above the at least one electrode or located between electrodes, examples of which are shown and described below in connection with FIGS. 27A-E and 28A-B.

After the sample 404 is processed by the microfluidic device 408 and/or optical system 410 to capture and/or quantify bacteria on the electrode(s), the sample 404 may be removed from the microfluidic device 408. For example, a second pump 416 may be provided for pumping the sample 404 out of the microfluidic device 408. The second pump 416 may be of any suitable type. In some embodiments, system 400 comprises a flow sensor 414 for measuring a flow rate at which the sample 404 is removed from the microfluidic device 408. The flow sensor 414 and the second pump 416 may be in communication to control a flow rate at which the sample 404 is removed from the microfluidic device 408.

As described herein, system 400 may be used for separating bacteria from other components in sample 404. System 400 comprises a waste region 418 arranged to receive other components of the sample 404 which have been separated from the bacteria by the microfluidic device 408 and subsequently removed from the sample 404, for example, using the second pump 416. In the description below, analysis of the fluid collected in waste region 418 may be referred to as analysis of the "effluent sample." System 400 may further include effluent region 420 for receiving a purified version of sample 404 containing substantially only target bacteria that were captured using microfluidic device 408.

In some embodiments, an amount of time needed to process a sample using system 400 is substantially less than an amount of time required to process a sample using a conventional sample processing system (e.g., PCM shown in FIG. 1). As shown in FIG. 4, processing a sample using system 400 may include three steps. In step 450, a sample is provided as input to microfluidic system 408 and bacteria are captured from the sample in the presence of an applied electric field. In step 460, automated on-chip quantification is performed, for example, using an optical system and computer 430 to analyze one or more images recorded by optical system 410. In step 470, further analysis may be performed on waste 418 and/or effluent sample 420, as desired. In sum, the entire process for detecting and/or quantifying bacteria in a sample using system 400 may take on the order of minutes or an hour to a few hours, which is substantially faster than the multiple days (e.g., 1 to 14 days) typically required to process samples using PCM discussed with reference to the system in FIG. 1.

Figure 5:
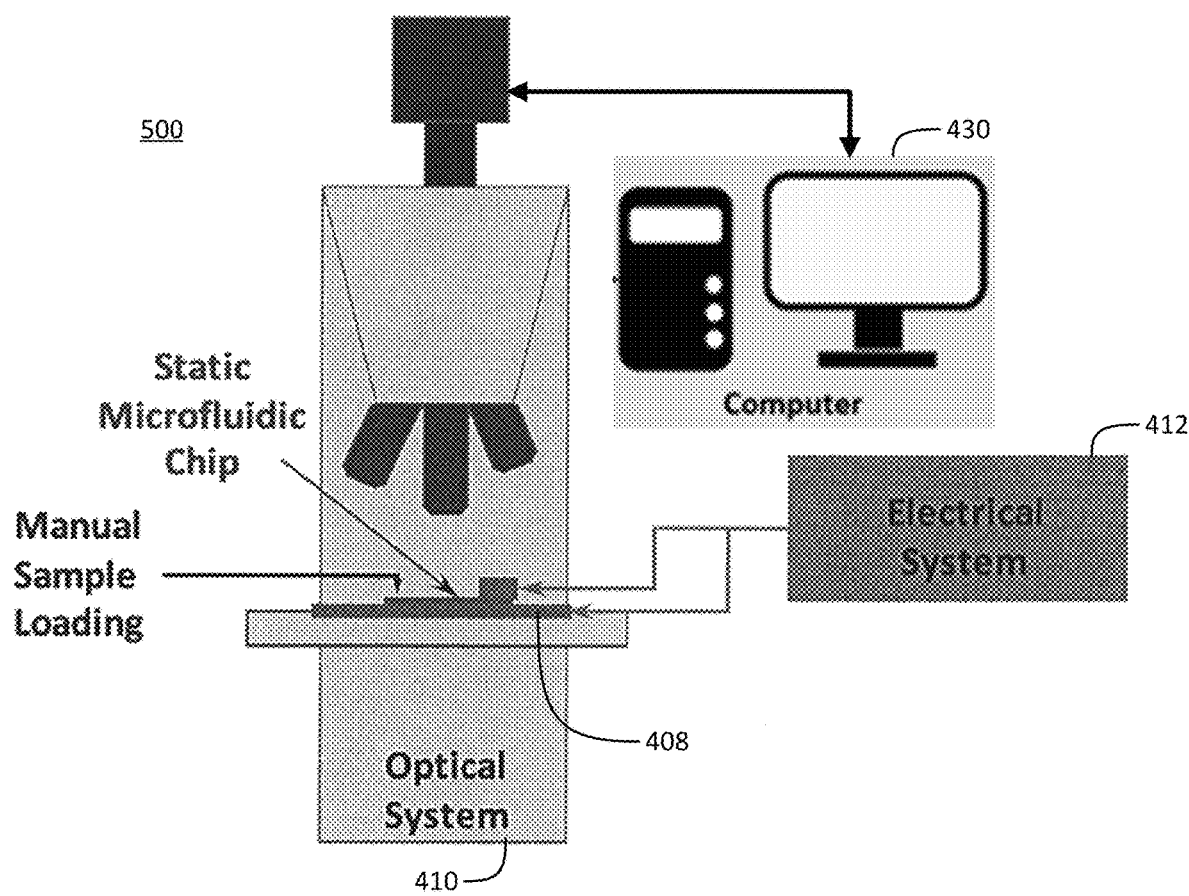
FIG. 5 illustrates a static system for detecting the presence of bacteria in a fluid sample, according to some embodiments.

In some embodiments, rather than pumping sample 404 through one or more channels through which the sample flows, sample 404 may be manually provided as input to microfluidic device 408 for analysis. For instance, one or more droplets of sample 404 may be provided as input to microfluidic device 508 using a pipette or other suitable technique. In such embodiments, the sample is analyzed in a "static" condition rather than in a condition in which bacteria are captured by the at least one electrode as the sample flows past the electrode(s) (e.g., as in the case of system 400 as shown in FIG. 4). FIG. 5 illustrates a system 500 for detecting bacteria in a sample, according to some embodiments. As shown, system 500 may include many of the same components as system 400, but may omit certain components of the system 500, such as the first pump 406, which are not needed when the sample is manually provided as input to the microfluidic device.

Figure 6A:
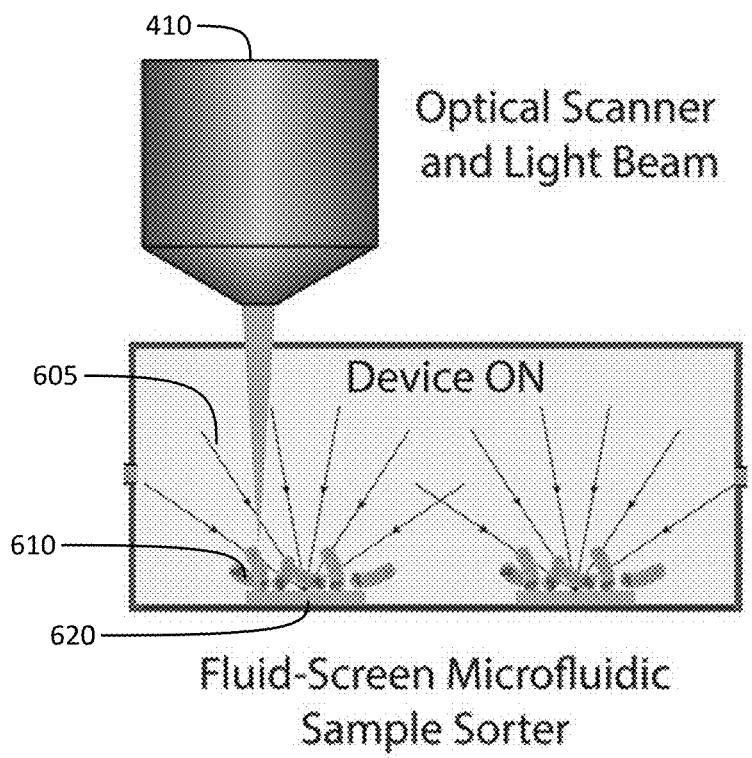
FIG. 6A illustrates a static system in operation for capturing bacteria in a sample, according to some embodiments.

FIG. 6A illustrates a schematic diagram of capturing bacteria from a sample using system 500. As shown, in the presence of an electric field 605 generated using electrode 620, bacteria 610 are attracted to the electrode 620 by a positive DEP force acting on the bacteria 610 in the sample. The trapped bacteria can then be imaged using optical system 410 to perform direct on-chip quantification. In some embodiments, a system with multiple electrodes may be used and the sample may be provided for interrogation by each of the electrodes.

Figure 6B:
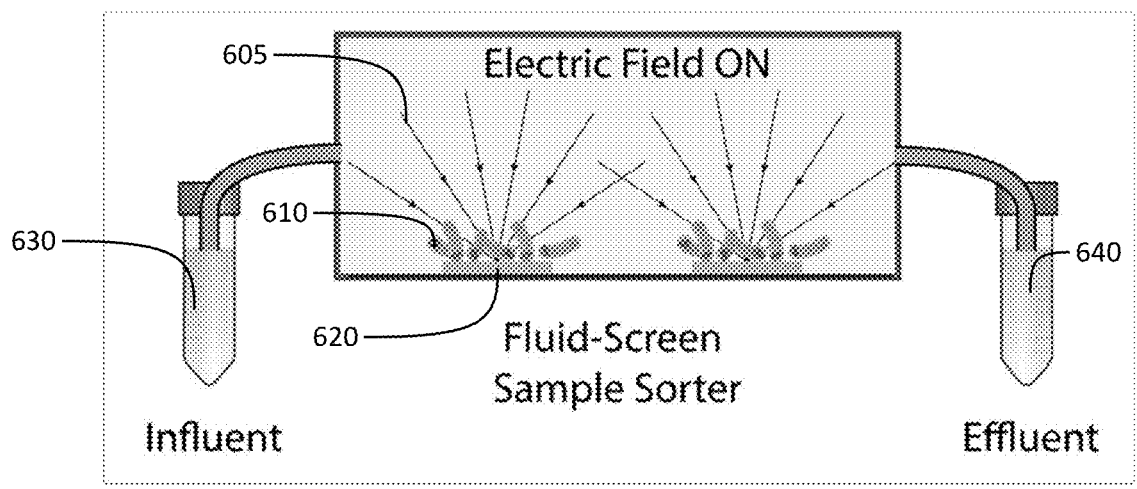
FIG. 6B illustrates a flow-based system in operation for capturing bacteria in a sample, according to some embodiments.

FIG. 6B illustrates a schematic diagram of capturing bacteria from a sample using system 400. In particular, the sample may be introduced to the microfluidic device from an influent region 630. Bacteria 610 included in the sample may be attracted to the surface of electrode 620 in the presence of an electric field 605 generated by the electrode as the sample flows past the electrode in the microfluidic device at a predetermined flow rate. Components not captured by the electrode 620 may be provided into an effluent region 640 (e.g., waste region 418 in FIG. 4) for further analysis or to be discarded. Additionally, or alternatively, bacteria captured by the electrode 620 may be released to effluent region 640 (or a different effluent region) by adjusting the applied electric field (e.g., by deactivating the electrode 620 thereby turning the electric field off).

Figure 7A:
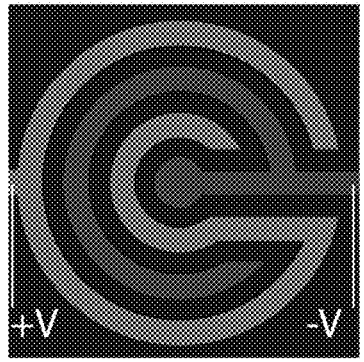
FIG. 7A illustrates a schematic of an electrode configuration that may be used to capture bacteria in accordance with some embodiments.
Figure 7B:
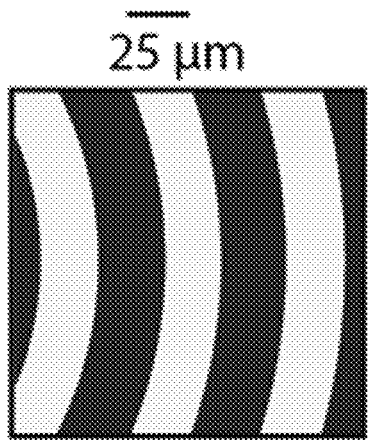
FIGS. 7B and 7C illustrate zoomed-in versions of the electrode configuration of FIG. 7A.
Figure 7C:
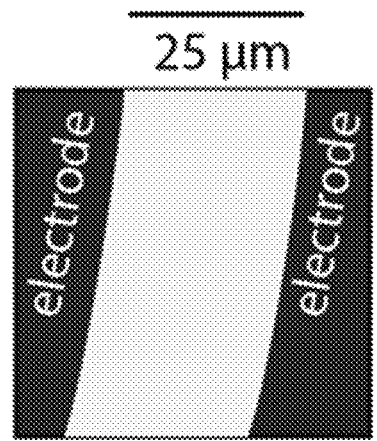
Figure 7D:
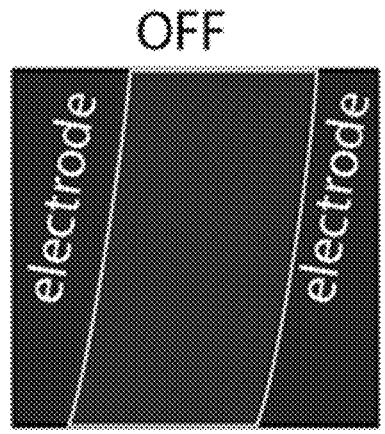
FIGS. 7D and 7E show operation of the electrode configuration of FIG. 7A in the absence and presence of an electric field, respectively, in accordance with some embodiments.
Figure 7E:
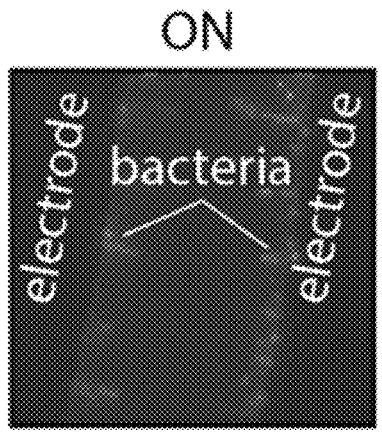
Figure 7F:
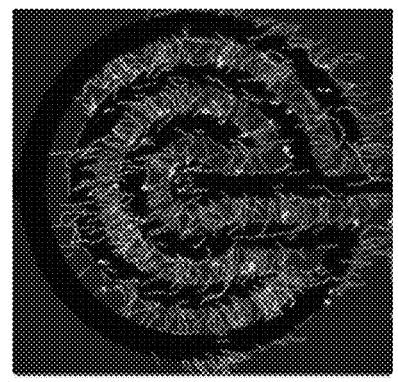
FIG. 7F shows an image of an entire electrode configuration having bacteria captured thereon in accordance with some embodiments.

FIGS. 7A-7F illustrate schematics of an electrode design that may be used in accordance with some embodiments. As shown in FIG. 7A, the electrode design may be a system of concentric rings or arcs in which every other ring from the center is electrically connected. The alternating rings may be connected to a voltage source having different polarities, thereby creating electric field gradients used to capture bacteria on the surface of the electrode. FIG. 7B shows a schematic of a part of an electrode system with applied alternating voltage polarity for the ring structure that may be used in some embodiments. FIG. 7C shows a zoomed-in schematic of part of the electrode design shown in FIG. 7B. For visual clarity the electrode is shown black, and glass, which is between electrodes, is shown in gray. FIG. 7D shows fluorescent imaging of the electrode when the electric field is off and FIG. 7E shows fluorescent imaging of the electrode when the electric field is on. A comparison of FIGS. 7D and 7E shows that *E. coli* bacteria (dots) are captured on the electrode edges of the ring structure when a voltage having an amplitude of 10 V and a frequency of 10 MHz is applied to the electrode. FIG. 7F shows an overview of the electrode with GFP-labelled bacteria captured from a 0.001×PBS solution spiked with bacteria. The device does not show saturation, even with high levels of bacteria.

In some embodiments, for example, the at least one electrode comprises at least one circular-shaped and/or partially-center-symmetric electrode (e.g., the electrode design shown in FIG. 7A). Additional example electrode designs are provided in FIGS. 33-37H.

Figure 33:
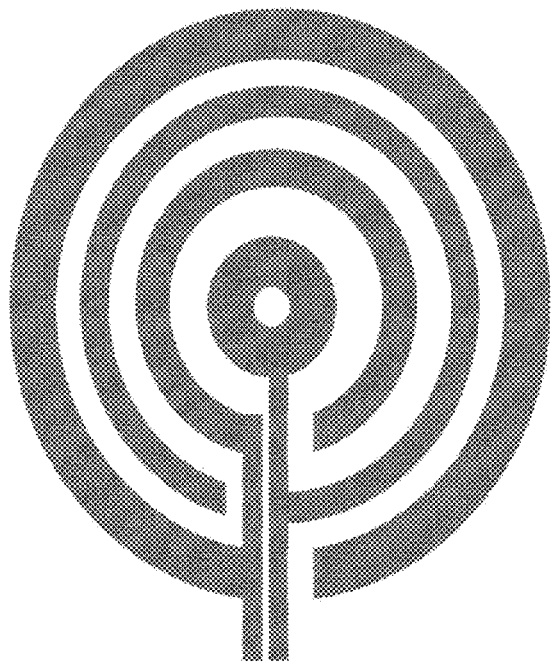
FIG. 33 illustrates a circular assembly of electrodes that may be used in accordance with some embodiments of the technology described herein.

For example, some embodiments make use of a circular assembly of coaxial or spiral-shaped electrodes such as shown in FIG. 33, where two or more independent voltages may be applied to the odd and even rings. This allows for an electric field gradient to be created in the region between the rings. The assembly of electrodes is constructed in such a way as to maximize the effects of the electric field on controlling the motion of the sample components.

Figure 34:
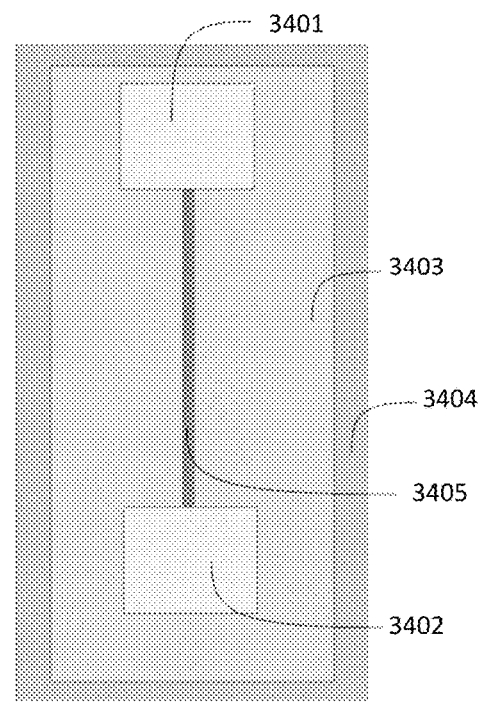
FIG. 34 illustrates a sensor assembly that may be used in combination with the electrode assembly of FIG. 33, according to some embodiments.

Such a device may be used to draw components of a sample, e.g., bacteria or other elements to the sensor array, which may be composed of elements such as those shown in FIG. 34, namely source 3401 and drain 3402, nanowire, nanoribbon or active sensing layer 3405, silicon or other semiconducting substrate 3404 and $SiO_2$ or other insulating interlayer 3403.

Figure 35:
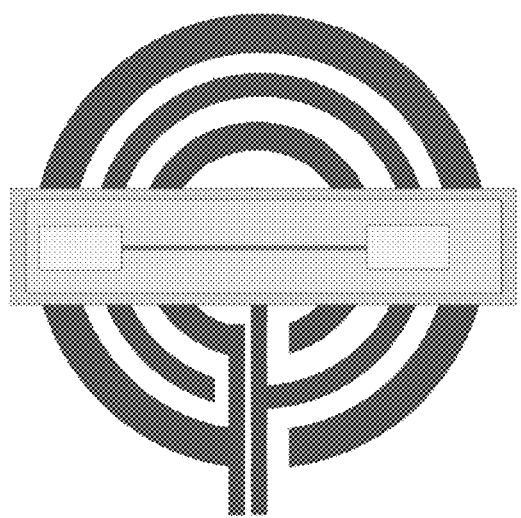
FIG. 35 illustrates the sensor assembly of FIG. 34 fabricated on top of the circular electrode assembly of FIG. 33, according to some embodiments.
Figure 36A:
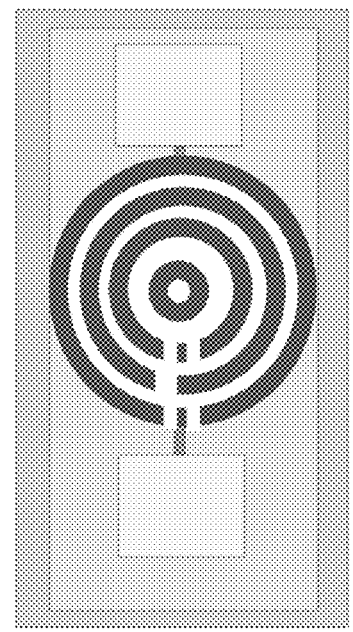
FIG. 36A illustrates the circular electrode assembly of FIG. 33 fabricated on top of the sensor assembly of FIG. 34, according to some embodiments.
Figure 36B:
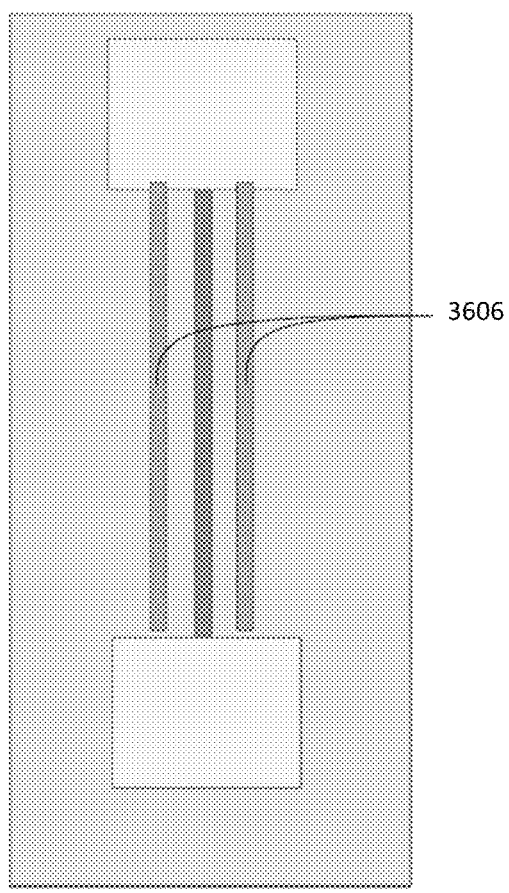
FIG. 36B illustrates an example device that includes supplementary wires arranged to provide a field gradient in a region of a central sensing layer, according to some embodiments.

The sensor assembly of FIG. 34 may be fabricated on top of circular DEP electrodes as shown in FIG. 35, or a set of circular electrodes may be fabricated on top of (or underneath, in some embodiments) the $SiO_2$ or other insulating layer as shown in FIG. 36A. Alternatively, two supplementary wires 3606 may be used as shown in FIG. 36B to provide a field gradient in the region of the central sensing layer.

A further aspect allows for selective treatment of individual sensors in a sensor array, such that each sensor or group of sensors can be made sensitive to a particular pathogen or family of pathogens. The sensor array may be such as that disclosed in U.S. patent application Ser. No. 12/517,230 titled "CMOS-COMPATIBLE SILICON NANO-WIRE SENSORS WITH BIOCHEMICAL AND CELLULAR INTERFACES" filed on Jul. 12, 2010, which is hereby incorporated by reference in its entirety. In some embodiments, the wires of the array form the bases of field-effect transistors, and thus implement nanowire FETs or FETs.

Figure 37A:
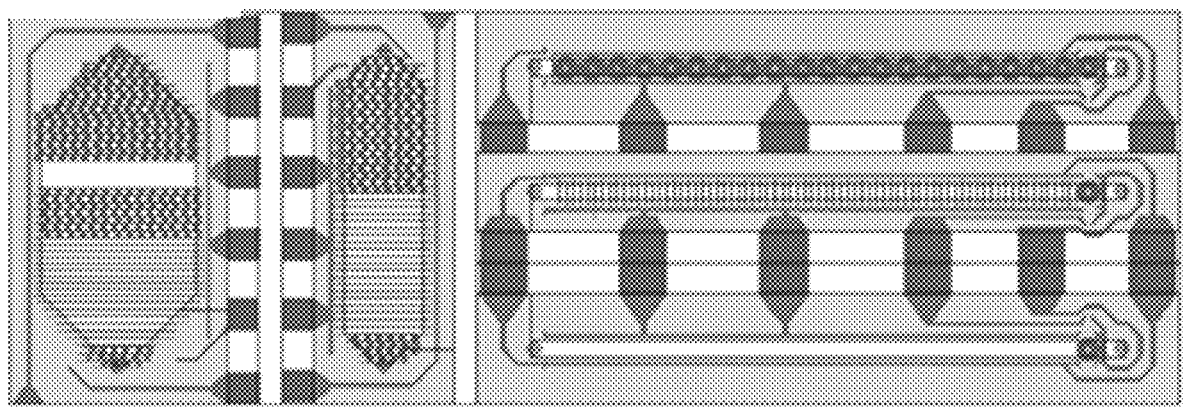
FIG. 37A illustrates a layout for an example microfluidic device, according to some embodiments.
Figure 37B:
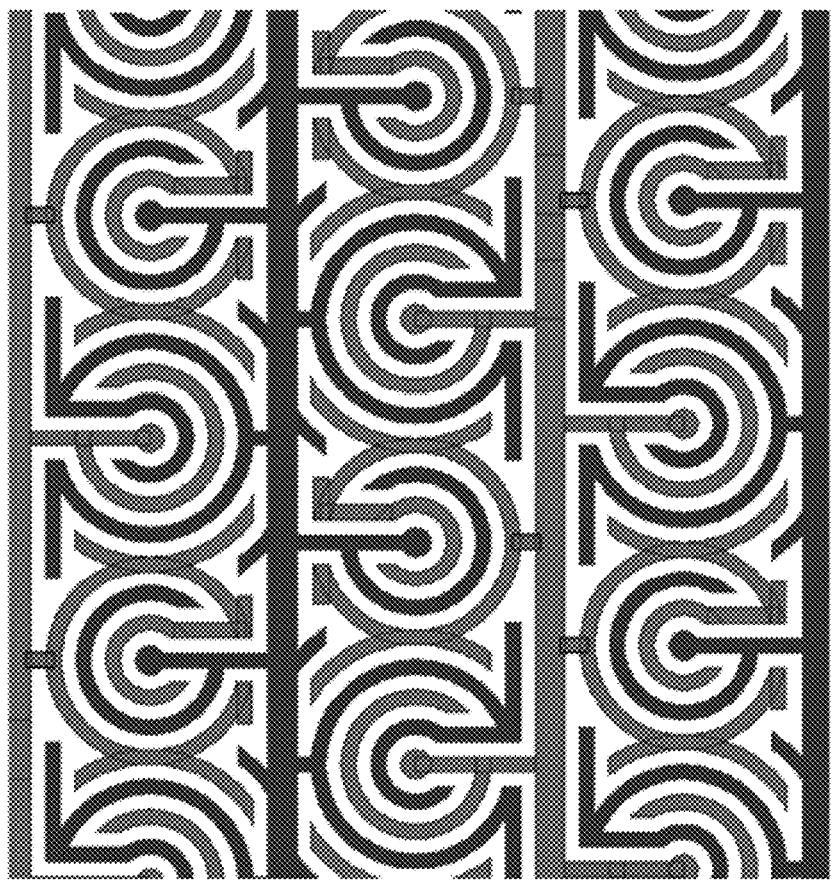
FIGS. 37B-37H illustrate different geometries of electrodes for high surface coverage to achieve high electric field gradients, according to some embodiments.
Figure 37C:
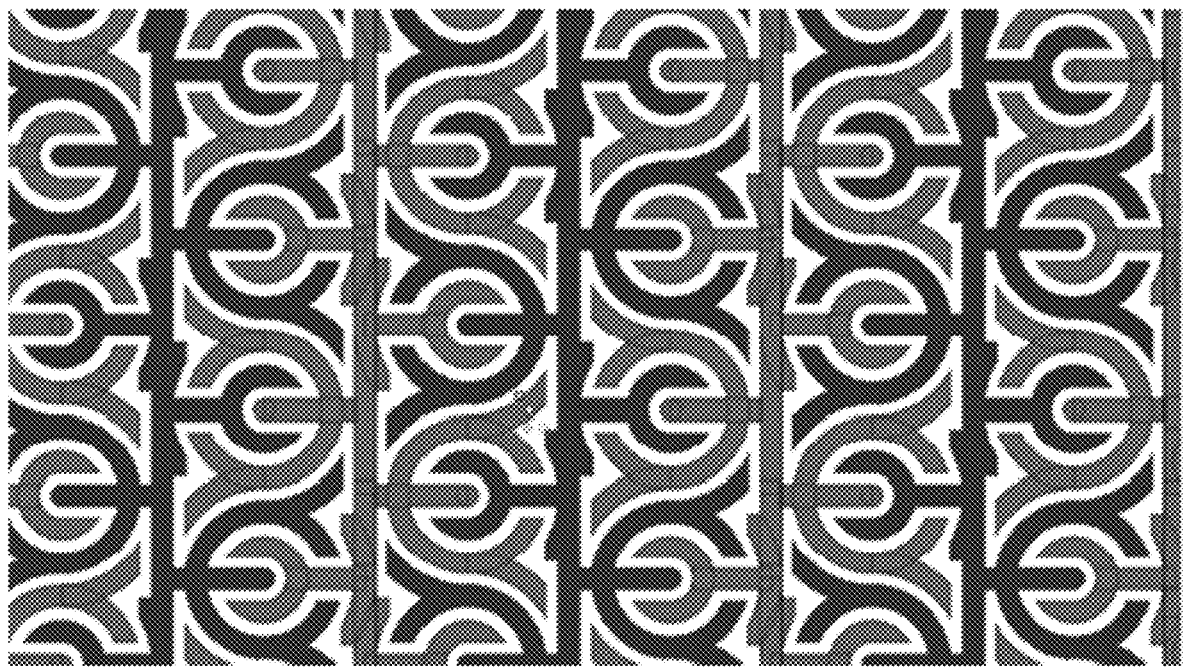
Figure 37D:
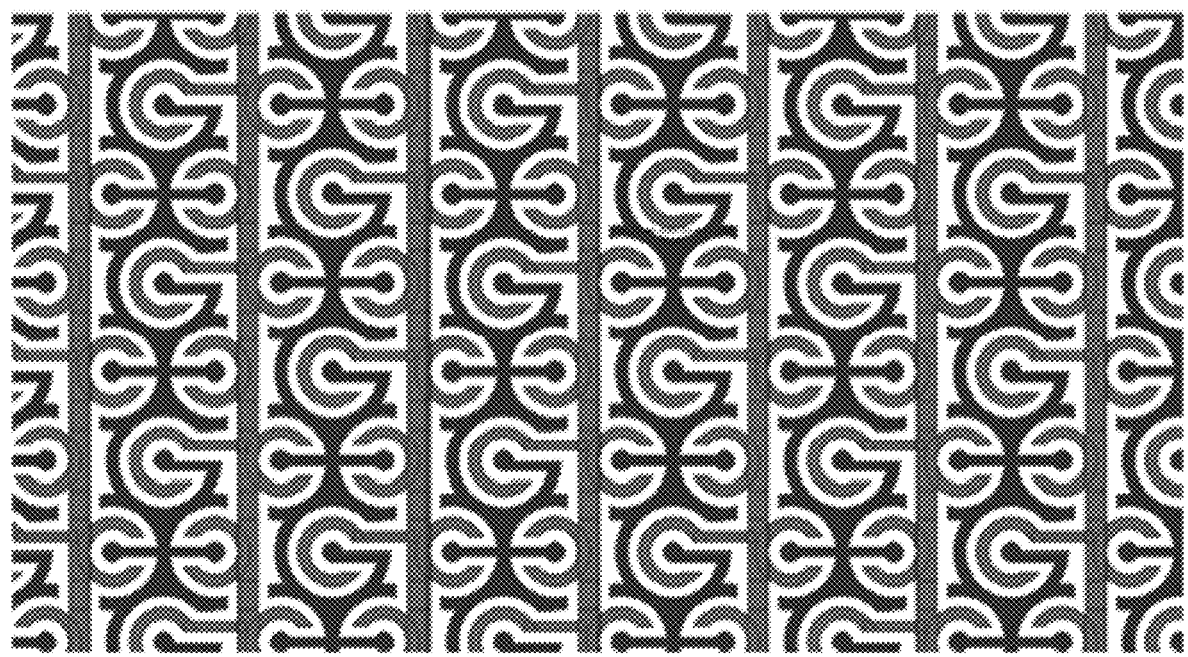
Figure 37E:
Figure 37F:
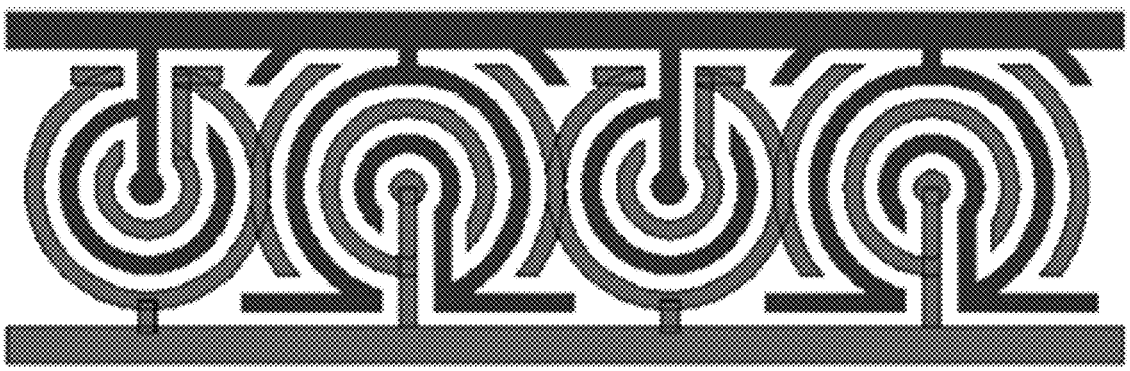
Figure 37G:
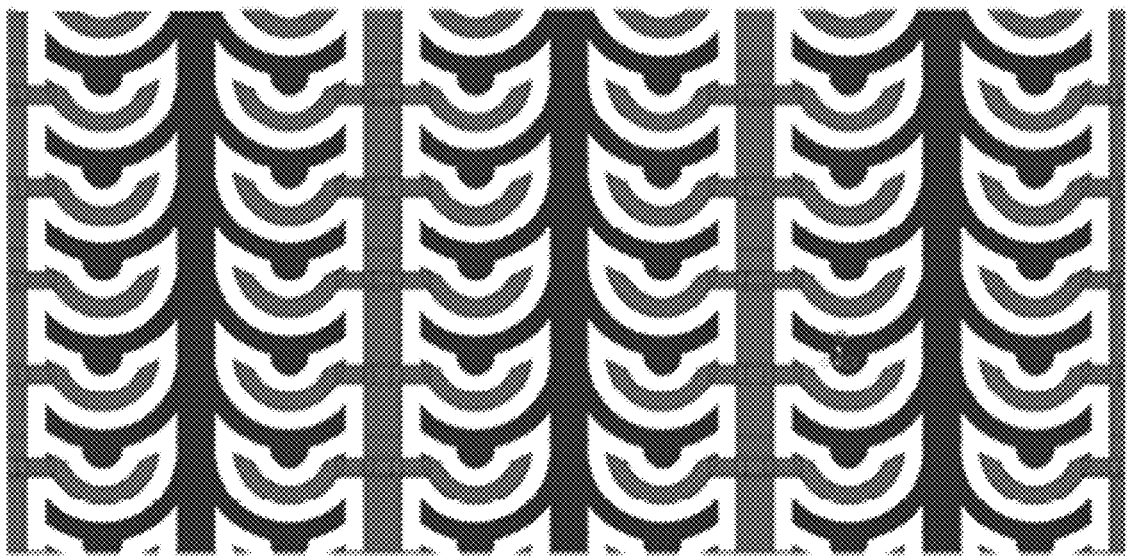
Figure 37H:
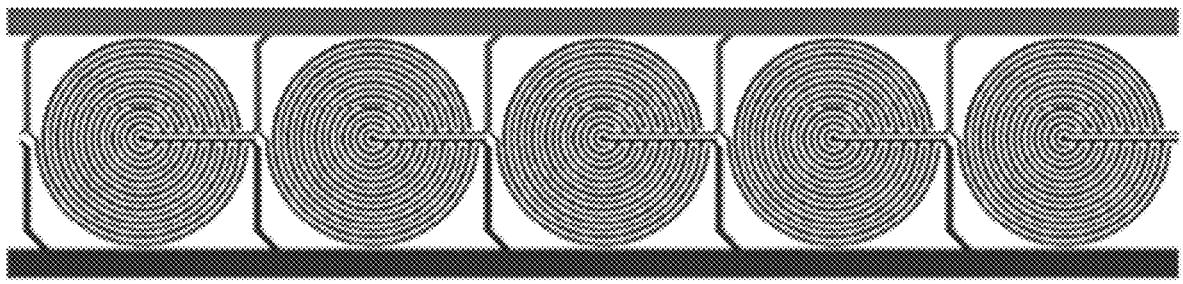

FIG. 37A shows the layout of a microfluidic device in accordance with some embodiments. FIGS. 37B-H illustrate different geometries of electrodes for high surface coverage to achieve high electric field gradients in accordance with some embodiments. In some embodiments, an electrode having one of the geometries shown in FIGS. 37A-H may cover the entire surface of a chamber (e.g., wall, top and/or bottom) of a fluidic device, examples of which are discussed above. The electrodes induce high field gradients, so that samples introduced into the chamber are exposed to high electric fields regardless of their position in the chamber. Such electrode design with a high surface coverage allows for control of over 99% of bacteria present in the sample and reduces false negatives.

As described herein, a further aspect in accordance with some embodiments involves the use of electroosmosis in addition to dielectrophoresis for transport. The frequencies at which electroosmosis are effective (e.g. tens of kHz) are widely separated from those useful in DEP, and therefore the two methods can be used simultaneously to provide a larger variety of separation regimes, and for a wider variety of objects to be separated.

In some embodiments, a high-density gradient of electric field is induced by electrodes which are matched to bacteria size, so that bacteria particles are within 10-500 times the size of the electrode and/or electrode spacing.

Figure 8:
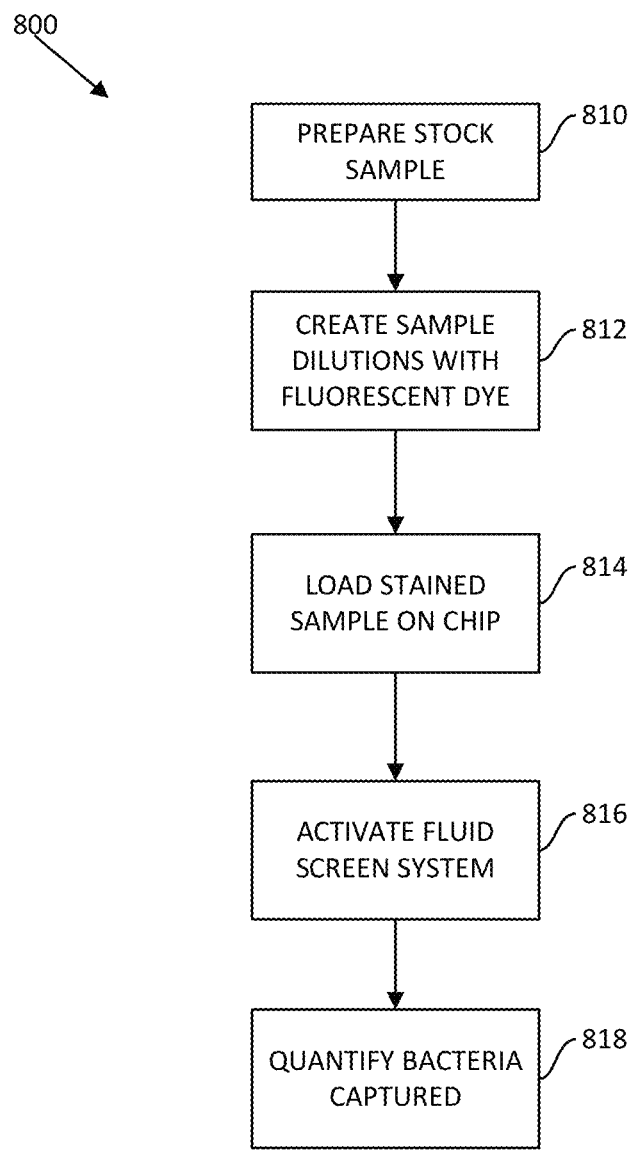
FIG. 8 is a flow chart of a process for detecting and quantifying bacteria in a static fluid sample in accordance with some embodiments.

FIG. 8 illustrates a process 800 for assessing variability in quantifying bacteria using the static system 500 shown in FIG. 5. In act 810 a stock sample including bacteria is prepared. For instance, cultured bacteria (e.g., *E. coli* bacteria) may be collected from a biofilm area of one or more agar plates using a sterile inoculation loop and the collected bacteria may be suspended in an amount (e.g., 2 mL) of Phosphate Buffered Saline (PBS) 1:1000 or another suitable buffer solution. The stock sample may be set up at a concentration ($10^7$-$10^8$ mL) using an optical density meter at 600 nm. An amount (e.g., 5 mL) of the stock sample may be prepared and a small amount (e.g., 1 mL) of the sample may be reserved for plating in serial 10× dilutions (e.g., $10^{-4}$, $10^{-5}$ and $10^{-6}$) on Tryptic Soy Agar (TSA) agar or selective agar media (MacConkey (MAC)) as a control after stock sample preparation. The stock sample prepared in act 810 is then used as a base to prepare the samples to be processed using system 500 to detect bacteria in the samples.

Process 800 then proceeds to act 812, where one or more sample dilutions are created. Fluorescent dye is added to the dilutions to facilitate imaging with the optical system. For instance, a concentration of bacteria in the test sample may be set at 100-400 CFU/mL in PBS diluted to 1:1000 by serial 10× dilution of the stock sample. To visualize the bacterial response to the applied electric field, a small amount (1 µL) of fluorescent dye Sybr Green (or another fluorescent dye) is added to 1 mL of the test sample and the solution is incubated (e.g., for 15 min at room temperature in darkness).

Process 800 then proceeds to act 814, where the diluted and stained sample is loaded into the chip. For instance, a micropipette may be used to load 2 µL of the stained sample into a channel of the chip. Process 800 then proceeds to act 816, where parameters for the applied electric field are determined and the electrode(s) in the microfluidic device are activated, resulting in the capture of bacteria by the electrode(s) by the applied DEP forces acting on the bacteria. Process 800 then proceeds to act 818, where the bacteria captured by the electrode in the presence of the applied electric field are quantified using fluorescence microscopy of the chip. After removing the electric field and flushing the chip with a solution to remove any bacteria microfluidic device, acts 814-818 may be repeated with a new diluted and fluorescently-labeled sample to generate multiple repeats of the on-chip quantification measurement. The chip may be imaged between each repeat to verify chip cleanliness. In the results described herein in connection with FIGS. 9 and 10A-C, multiple (e.g., 12) repeats were generated to assess variability in bacterial quantification. A null control image of the electrode without bacteria using the same fluorescent application was also collected for comparison.

Figure 9:
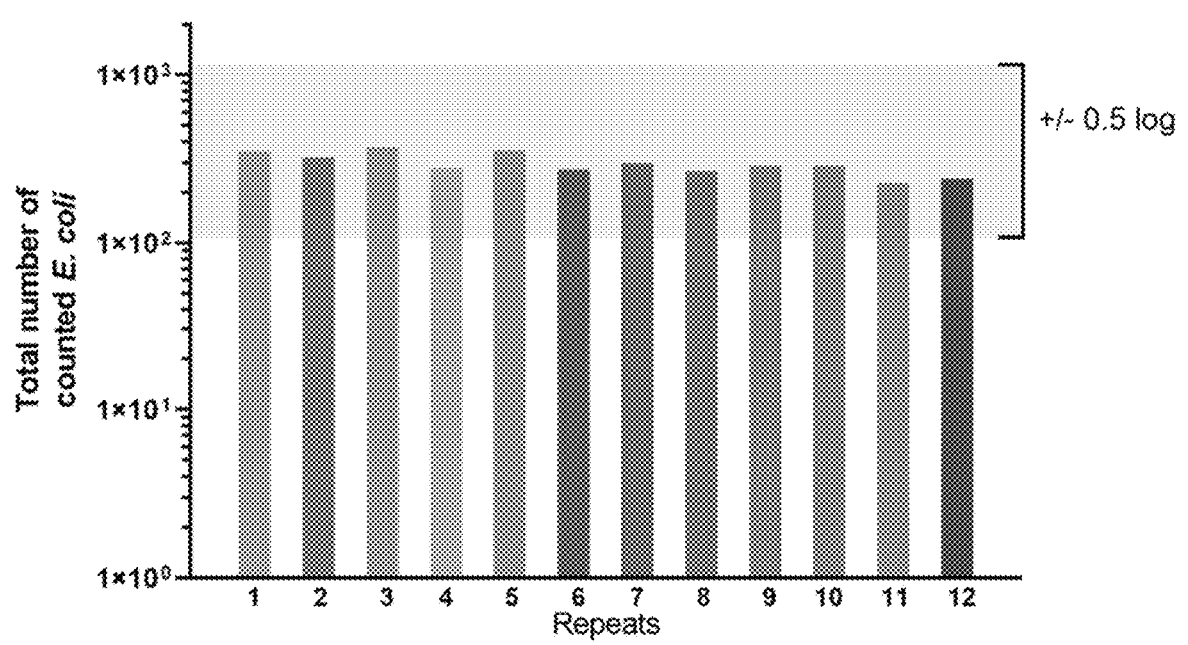
FIG. 9 shows results of an experiment for quantifying bacteria in a sample using the process of FIG. 8.

Two biological samples including bacteria were processed using process 800. Twelve technical repeats were performed to demonstrate the precision and repeatability of bacteria quantification with the system 500. FIG. 9 shows bar plots of the total number of bacteria counted across twelve repeats using process 800 for a first biological sample and a second biological sample, respectively. Each vertical bar represents the number of bacteria counted for an individual experiment. A variability range of +/−0.5 log is shown as a shaded horizontal bar in FIG. 9. As shown, the bacterial quantification variability across repeats using the system 500 was substantially smaller than the +/−0.5 log range for variability (which is a range often used to validate new methods for clinical use), thereby demonstrating a system for bacterial capture and quantification with improved precision and repeatability compared to conventional techniques such as PCM, which typically have measurements at or near the boundaries of the acceptable +/−0.5 log spread.

Figures 10A, 10B, 10C:
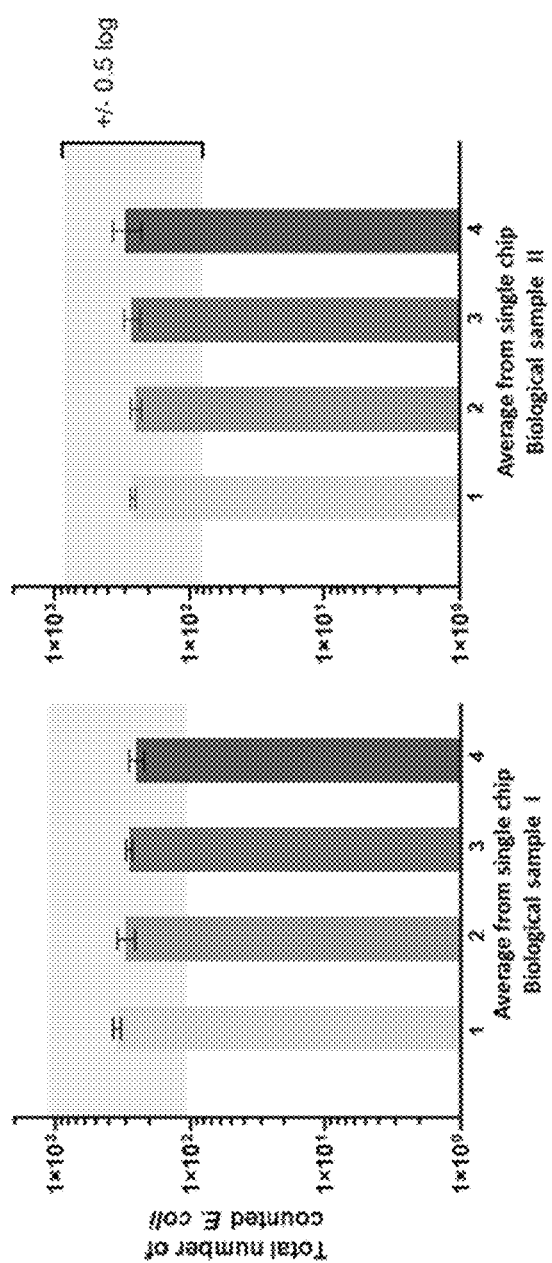
FIGS. 10A-10C show results of experiments for quantifying bacteria in a sample using multiple microfluidic devices using the process of FIG. 8.

The precision and repeatability in enumeration of multiple microfluidic chips designed in accordance with the techniques herein is shown in FIGS. 10A-C. Eight different microfluidic chips were used to quantify the number of captured bacteria across the two biological samples. Each chip was used to count the bacteria three times (each chip had three channels), demonstrating a high degree of precision and repeatability in chip capture and image processing performance. FIGS. 10A and 10B show the total number of bacteria counted on each of four different chips for the first and second biological samples, respectively. For reference, as with the bar plot in FIG. 9, the +/−0.5 log variability range is shown as a shaded horizontal bar in FIGS. 10A-C. The variability from chip to chip is substantially smaller than the +/−0.5 log variability spread for each of the biological samples. FIG. 10C shows a statistical comparison of the two biological samples across twelve repeats for each sample. Overall, there was no significant difference between biological repeats, demonstrating the very high precision and repeatability in the capture and quantification of bacteria using the techniques described herein. Statistical analysis from the eight different chips tested is summarized in Table 2 below.

TABLE 2

Statistical analysis of the repeatability of bacteria capture compared between eight microfluidic chips.

| | | True number of bacteria | Mean | SD | % CV |
|---|---|---|---|---|---|
| Biological repeat 1 | | | | | |
| Chip 1 | Channel 1 | 350 | 348.000 | 23.065 | 6.628 |
| | Channel 2 | 324 | | | |
| | Channel 3 | 370 | | | |
| Chip 2 | Channel 1 | 279 | 302.333 | 45.709 | 15.119 |
| | Channel 2 | 355 | | | |
| | Channel 3 | 273 | | | |

TABLE 2-continued

Statistical analysis of the repeatability of bacteria capture compared between eight microfluidic chips.

|  |  | True number of bacteria | Mean | SD | % CV |
|---|---|---|---|---|---|
| Chip 3 | Channel 1 | 297 | 283.667 | 15.275 | 5.385 |
|  | Channel 2 | 267 |  |  |  |
|  | Channel 3 | 287 |  |  |  |
| Chip 4 | Channel 1 | 287 | 252.000 | 31.000 | 12.302 |
|  | Channel 2 | 228 |  |  |  |
|  | Channel 3 | 241 |  |  |  |
| Biological repeat 2 | | | | | |
| Chip 1 | Channel 1 | 254 | 263.333 | 11.372 | 4.319 |
|  | Channel 2 | 260 |  |  |  |
|  | Channel 3 | 276 |  |  |  |
| Chip 2 | Channel 1 | 235 | 251.000 | 21.932 | 8.739 |
|  | Channel 2 | 242 |  |  |  |
|  | Channel 3 | 276 |  |  |  |
| Chip 3 | Channel 1 | 312 | 269.333 | 36.950 | 13.719 |
|  | Channel 2 | 248 |  |  |  |
|  | Channel 3 | 248 |  |  |  |
| Chip 4 | Channel 1 | 239 | 297.333 | 70.727 | 23.787 |

Figure 11:
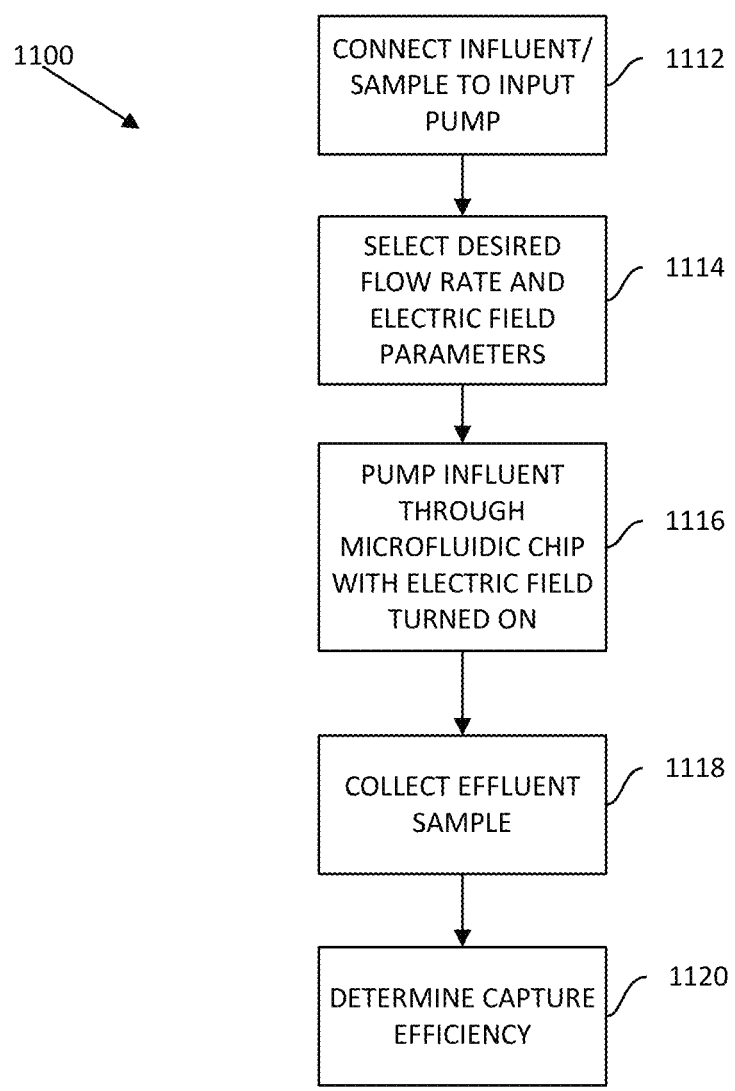
FIG. 11 is a flow chart of a process for detecting and quantifying bacteria in a flowing fluid sample in accordance with some embodiments.

FIG. 11 illustrates a process 1100 for assessing the efficiency of bacterial capture using the microfluidic system 400 shown in FIG. 4. In act 1112, an influent sample is connected to an input pump of the microfluidic system. A small amount (e.g., 1 mL) of influent sample is reserved for culturing using PCM, as discussed in further detail below. Process 1110 then proceeds to act 1114, where a desired flow rate and electric field parameters are selected. As discussed further below, capture efficiency of system 400 at a plurality of flow rates was tested. The electric field parameters may be tuned to attract multiple types of bacteria to the electrode(s) within the microfluidic system or may be tuned to selectively capture one or more types of bacterial species while repelling one or more other types of bacterial species. In some embodiments, setting electric field parameters comprises setting an amplitude and/or frequency of a voltage provided to activate the one or more electrodes within the microfluidic system.

Process 1100 then proceeds to act 1116, where the electric field is turned on in accordance with the selected parameters and the influent sample is pumped at the selected flow rate through one or more channels in the microfluidic device associated with the one or more electrodes. As the sample traverses the portion of the channel(s) proximate to the one or more electrodes, bacteria are captured from the sample on the surface of the electrode(s) due to a positive DEP force acting on the bacteria in the sample. The remaining components in the sample not captured by the electrode proceed through the channel(s), where they are collected as effluent in act 1118. In some embodiments, the components in the sample that are not captured by the electrode(s) are first stored in a chamber prior to being pumped out of the microfluidic system into an effluent region for further analysis.

Process 1100 then proceeds to act 1120, where the capture efficiency of the microfluidic device is determined. Capture efficiency may be determined using one of at least two techniques. In a first technique, "on-chip quantification" of bacteria captured by the electrode is performed to count the number of captured bacteria in one or more images captured by an optical system. For instance, following capture of the bacteria by the electrode(s), an optical system may be used to capture one or more images of the electrode(s) while the bacteria are captured by the electrode. The number of bacteria captured on the electrode(s) may be then be quantified by analyzing the one or more images captured by the optical system and compared to an analysis of the effluent sample.

In a second technique, "PCM quantification" of bacteria is performed by comparing an amount of bacteria in the influent sample with an amount of bacteria in the effluent sample. For instance, PCM quantification may proceed according to steps described in connection with FIG. 1.

FIGS. 1 and 4, respectively show general schematics of the PCM quantification and on-chip quantification counting techniques for assessing efficiency of bacterial capture of a microfluidic system designed in accordance with some embodiments. For both techniques 1 mL of the effluent (output sample) was collected and plated immediately on MAC agar plates for enumeration using PCM to calculate the number of Colony Forming Units (CFUs).

For PCM quantification, a biological sample provided as input to the microfluidic device is referred to as the influent sample. The sample that exits the chip following collection of the bacteria on the electrode(s) in the microfluidic device is collected as the effluent sample. Both the influent sample and the effluent sample are cultured on proper media, and after 24 hours of growth, the number of bacteria are quantified, and the two numbers are compared. The factor that shows the efficiency of the process is called the capture efficiency and is calculated as:

$$\text{Capture Efficiency} = \left(1 - \frac{Conc_{eff}}{Conc_{inf}}\right) * 100\%$$

where $Conc_{eff}$ is the concentration of bacteria in the effluent sample and $Conc_{inf}$ is the concentration of bacteria in the influent sample.

FIG. 12A illustrates the capture efficiency for various influent concentrations of bacteria as determined using PCM quantification. As shown, the capture efficiency is 100% or nearly 100% at all influent concentrations tested. FIG. 12B illustrates capture efficiency for various influent concentrations and flow rates. As shown, the capture efficiency depends on flow rate and electric field settings (e.g., how strong the DEP force is for particular bacteria being captured). At flow rates less than 480 uL/min the capture efficiency is greater than or equal to 99.99%. Though not shown, flow rates as low as 10 uL/min were tested and showed capture efficiencies of at least 99.99%. As flow rates are increased, the capture efficiency is decreased, but still remains above 99.9% in experiments in which the flow rate was 960 uL/min or less. FIG. 12C shows additional capture efficiency results when the electric field settings were changed from those used in the experiment that produced the results in FIG. 12B. The results in FIG. 12C confirm that capture efficiency depends on flow rate and electric field parameters.

Additional experiments in which an observed overall 100% bacterial capture efficiency, as verified by PCM quantification, were also performed. An unstained bacteria capture experiment was repeated in four biological replicates (each corresponding to a new separately grown bacterial sample) with three technical replicates (each being a triplicate repetition of the bacteria capture experiment, done sequentially, from the same biological replicate) per each biological replicate for a total of 12 tests. All four biological repeats using the system 400 in each of the 12 total conducted experiments, demonstrated 100% bacteria capture efficiency and repeatability. Detailed data of the additional PCM quantification experiments is summarized in Table 3, including the number of bacterial colonies in the negative control, bacterial concentration in influent, bacterial concentration in effluent and the calculated capture efficiency. The number of CFUs in each influent was between 20 CFU/mL and 420 CFU/mL.

Note that in the PCM quantification experiment having results summarized in Table 3 and resulting in 100% capture efficiency, bacteria in the influent sample were not stained with any fluorescent stain. Lack of bacterial staining in a PCM quantification experiment avoids any potential growth inhibition by the fluorescent dye on MAC agar plates. For all conducted experiments, acceptable growth and viability range +/−0.5 log were reported.

FIGS. 13A and 13B show the results of capture efficiency experiments performed using a microfluidic device designed in accordance with the techniques described herein, and using PCM quantification of bacteria in influent and effluent samples. FIG. 13A shows data presented as a mean and +/−SD from 3 technical replicates for each biological replicate. FIG. 13B shows data presented as a mean and +/−SD from four biological replicates and their technical replicates, for a total of 12 tests. The shaded bar represents a growth and viability variance range of +/−0.5 log. In every experiment, the microfluidic device captured 100% of bacteria, as evidenced by zero PCM growth in effluent samples. The 100% capture efficiency is maintained in a broad range of bacteria concentrations. Numeric values associated with the plots shown in FIGS. 13A and 13B is shown in Table 4 below.

TABLE 3

Bacterial capture results using PCM quantification and on-chip quantification techniques
Plate-Count Method [cfu/mL] "PCM quantification"

| | Biol Rep 1 | | | Biol Rep 2 | | | Biol Rep 3 | | |
| --- | --- | --- | --- | --- | --- | --- | --- | --- | --- |
| | Tech Rep 1 [Ave cfu/mL] | Tech Rep 2 [Ave cfu/mL] | Tech Rep 3 [Ave cfu/mL] | Tech Rep 1 [Ave cfu/mL] | Tech Rep 2 [Ave cfu/mL] | Tech Rep 3 [Ave cfu/mL] | Tech Rep 1 [Ave cfu/mL] | Tech Rep 2 [Ave cfu/mL] | Tech Rep 3 [Ave cfu/mL] |
| $Neg_{CTRL}$ | 0 | 0 | 0 | 0 | 0 | 0 | 0 | 0 | 0 |
| Influent ≤250 cfu/mL | $7 \times 10^1$ | $2 \times 10^1$ | $1.7 \times 10^1$ | $5.2 \times 10^1$ | $1.2 \times 10^1$ | $4.2 \times 10^1$ | $6.5 \times 10^1$ | $5.33 \times 10^1$ | $2.0 \times 10^1$ |
| Effluent | 0 | 0 | 0 | 0 | 0 | 0 | 0 | 0 | 0 |
| $Cap_{eff}$ [%] | 100 | 100 | 100 | 100 | 100 | 100 | 100 | 100 | 100 |
| On-Chip Quantification | | | | | | | | | |
| $Neg_{CTRL}$ | 6 | 15 | 3 | 4 | 3 | 12 | 26 | 13 | 5 |
| Capture | 184 | 130 | 198 | 124 | 179 | 189 | 124 | 128 | 139 |
| Total Capture [Cap-$Neg_{CTRL}$] | 178 | 115 | 195 | 120 | 176 | 177 | 98 | 115 | 134 |

TABLE 4

Results of capture efficiency experiments according to some embodiments
Plate-Count Method [cfu/mL]

| | Biological Replicate 1 | | | Biological Replicate 2 | | | Biological Replicate 3 | | | Biological Replicate 4 | | |
|---|---|---|---|---|---|---|---|---|---|---|---|---|
| | Tech Rep 1 [Ave cfu/mL] | Tech Rep 2 [Ave cfu/mL] | Tech Rep 3 [Ave cfu/mL] | Tech Rep 1 [Ave cfu/mL] | Tech Rep 2 [Ave cfu/mL] | Tech Rep 3 [Ave cfu/mL] | Tech Rep 1 [Ave cfu/mL] | Tech Rep 2 [Ave cfu/mL] | Tech Rep 3 [Ave cfu/mL] | Tech Rep 1 [Ave cfu/mL] | Tech Rep 2 [Ave cfu/mL] | Tech Rep 3 [Ave cfu/mL] |
| $Neg_{CTRL}$ | 0 | 0 | 0 | 0 | 0 | 0 | 0 | 0 | 0 | 0 | 0 | 0 |
| Influent ≤250 cfu/mL | $3.3 \times 10^2$ | $2.4 \times 10^2$ | $2 \times 10^2$ | $2.8 \times 10^2$ | $4.2 \times 10^2$ | $1.3 \times 10^2$ | $1.6 \times 10^2$ | $2.9 \times 10^2$ | $0 \times 10^2$ | $1.9 \times 10^2$ | $1.5 \times 10^2$ | $2 \times 10^2$ |
| Effluent | 0 | 0 | 0 | 0 | 0 | 0 | 0 | 0 | 0 | 0 | 0 | 0 |
| $Cap_{eff}$ [%] | 100 | 100 | 100 | 100 | 100 | 100 | 100 | 100 | 100 | 100 | 100 | 100 |

Rather than comparing the number of cultured bacteria in influent and effluent samples using PCM quantification as described above, some embodiments use "on chip quantification" of bacteria imaged while the bacteria are captured on the microfluidic chip. For on-chip quantification, the number of bacteria was determined by background subtraction from the total count on the chip. The total number of bacteria was determined optically as a number of spots that produced a fluorescent signal. A spot was counted if the size of the spot corresponded to at least 25% of bacterial size, in this case more than 8 connected pixels, which corresponds to 0.5 μm. First, bacteria were recognized from the fluorescent images based on spot size and the difference of intensity between the intensity maximum and the background. Electrode position was determined from the optical electrode image. Capture efficiency was calculated as: 1−Number of bacteria captured on electrode/Total number of bacteria The fluorescent images were filtered with a digital band-pass filter to pass the wavelength of the fluorophore (509 nm for green fluorescent protein (GFP)); the range between black (minimum) and the brightest bacterium pixel (maximum) was then reassigned to a full color scale.

Figure 14:
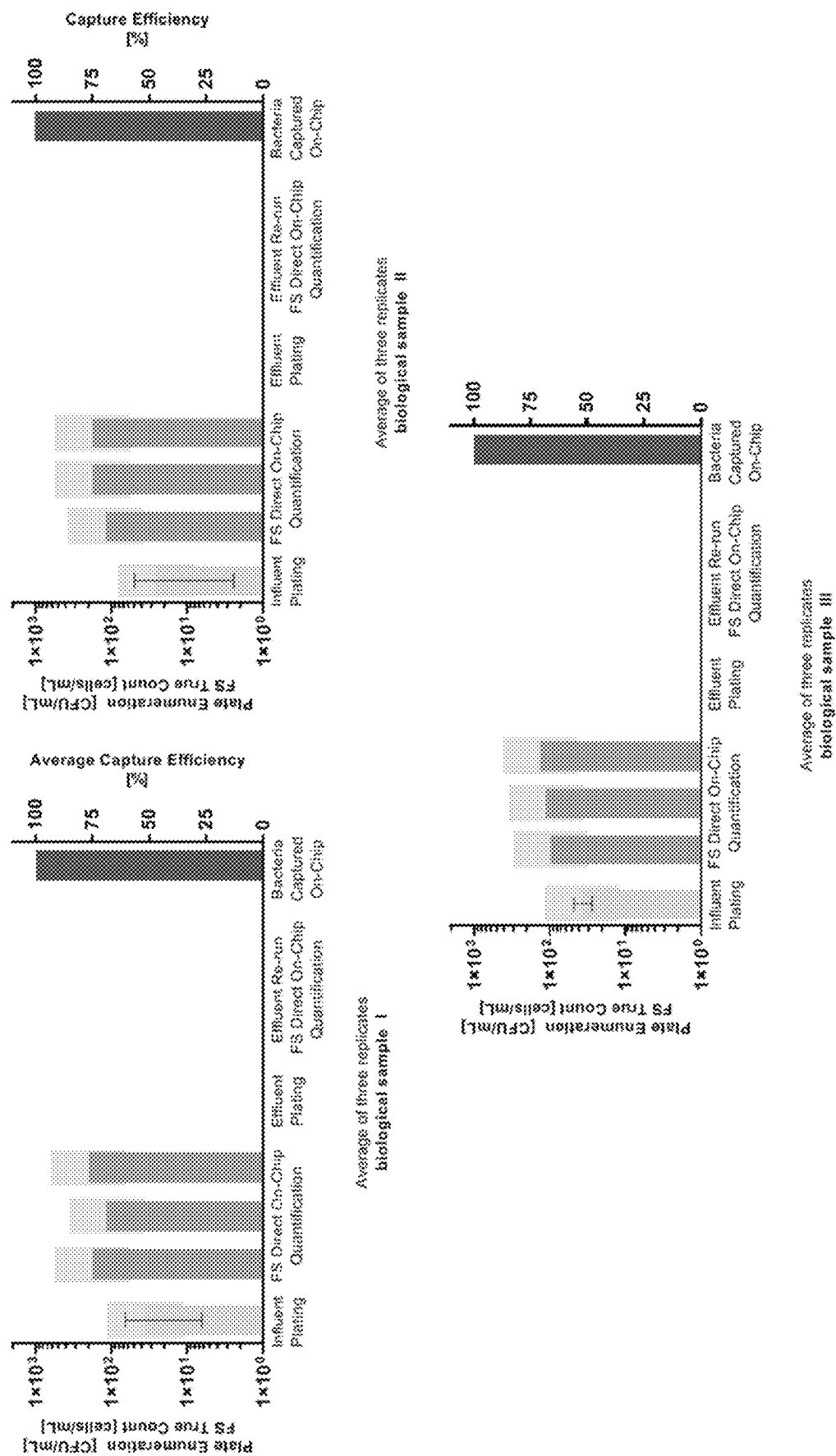
FIG. 14 shows capture efficiency results of an on-chip quantification technique for captured bacteria in accordance with some embodiments.

As shown in FIG. 14, direct "on chip quantification" of captured bacteria may be a more reliable technique for quantifying bacteria in a sample compared to a standard established, indirect "PCM quantification," which requires converting the real number of captured bacteria to CFU/mL values. Additionally, FIG. 14 shows that the direct "on chip quantification" technique yields a very small bacteria counting error, which may be due in part, to manual operation of the system 400. The PCM quantification technique was shown to be generally less reliable, as it is not only indirect, but also introduces multiple human errors (e.g., during sample preparation and dilution, plating on agar plates, etc.). Therefore, standard PCM quantification is subjected to a large statistical error that often goes beyond the +/−0.5 log range.

Figure 15:
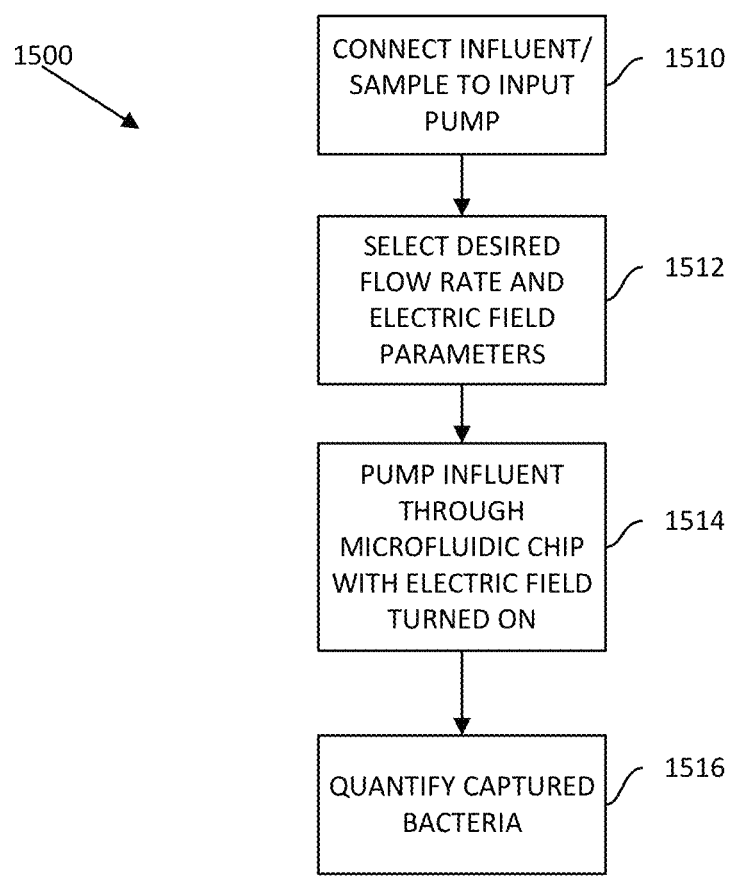
FIG. 15 is a flow chart of a process for quantifying bacteria in a sample in accordance with some embodiments.

FIG. 15 illustrates a process for detecting and quantifying bacteria in a sample in accordance with some embodiments. In act 1510, an influent sample is connected to an input pump of the microfluidic system. The influent sample may include a fluorescent dye configured to label bacteria in the sample to facilitate on-chip quantification. Alternatively, a fluorescent dye may be provided to the microfluidic system to label bacteria after they have been captured. In some embodiments, a fluorescent dye is not used. Process 1500 then proceeds to act 1512, where a desired flow rate and electric field parameters are selected. In some embodiments, the flow rate may be selected to achieve an expected capture efficiency of bacteria by the electrode. For instance, in some embodiments, a flow rate between 10-960 ul/min may be selected to achieve a capture efficiency of at least 99%. In some embodiments, a flow rate between 480-960 ul/min may be selected to achieve a capture efficiency of at least 99%. In some embodiments, a flow rate between 720-960 ul/min may be selected to achieve a capture efficiency of at least 99%. In some embodiments, a flow rate between 840-960 ul/min may be selected to achieve a capture efficiency of at least 99%. In some embodiments, a flow rate may be selected to achieve a capture efficiency of at least 99.6%. In some embodiments, a flow rate between 240-480 ul/min may be selected to achieve a capture efficiency of at least 99.9%. In some embodiments, a flow rate of 240 ul/min may be selected to achieve a capture efficiency of at least 99.99%.

The electric field parameters may be tuned to attract multiple types of bacteria to the electrode(s) within the microfluidic system or may be tuned to selectively capture one or more types of bacterial species while repelling one or more other types of bacterial species. In some embodiments, setting electric field parameters comprises setting an amplitude and/or frequency of a voltage provided to activate the one or more electrodes within the microfluidic system. In some embodiments, the frequency of an AC voltage provided to the electrode(s) is within a range between 900 Hz-2 MHz. In some embodiments, the frequency of the AC voltage is 1 MHz.

Process 1500 then proceeds to act 1514, where the electric field is turned on in accordance with the selected parameters and the influent sample is pumped at the selected flow rate through one or more channels in the microfluidic device associated with the one or more electrodes. As the sample traverses the portion of the channel(s) proximate to the one or more electrodes, bacteria are captured from the sample on the surface of the electrode(s) due to a positive DEP force acting on the bacteria in the sample.

Process 1500 then proceeds to act 1516, where a number of bacteria captured on the electrode(s) are quantified, for example, by analyzing one or more images captured by an optical system while the bacteria are captured by the electrode(s) (e.g., using direct on-chip quantification, as described herein).

Recent discoveries have shown relationships between the human microbiome and human health. There is a great promise of creating therapeutics that change the human microbiome to cure diseases such as obesity, diabetes, autism, bipolar disorder and Alzheimer's disease.

Research and development of new therapeutics requires sequencing human samples such as fecal samples, skin swabs, vagina swabs, nasal swabs, samples from intestines and the gastrointestinal (GI) tract, mouth and gums swabs.

Most microbiome samples from a human body contain both non-bacterial cells and bacterial species that are present in high abundance. The majority of DNA extracted from human microbiome samples is from the non-bacterial cells and bacterial species that are present in high abundance, which makes it challenging to detect the presence of bacterial or viral species present in low abundance. Although human microbiome samples are used as an example of the type of sample that may be processed in accordance with some embodiments, it should be appreciated that microbiome samples may alternatively be processed from plants, soil, water or animals.

Some embodiments are directed to methods and apparatus for detecting bacteria at low concentrations in a complex sample by enriching the bacteria following capture. For instance, some embodiments relate to a method for enriching for bacterial species from complex samples, such as fecal samples, where the bacterial species of interest are below 0.1% of the total bacterial or cellular concentration, which is generally considered the reliable limit of bacterial detection with sequencing. In particular, some embodiments relate to a method that uses an electric field in a microfluidic chip to remove cellular noise from samples and selectively enrich a bacterial species of interest. An application of such techniques is to selectively capture bacterial species in fecal samples or other complex samples while removing non-bacterial cells and non-target bacteria (e.g., gram-negative bacteria) from the samples. Such an improved process for detecting low concentrations of bacteria may provide an automated process for specific enrichment of a bacterial species from a fecal sample or another complex sample in minutes to hours, instead of days as is typically required using standard techniques for detecting bacteria in samples (e.g., PCM).

The inventors have recognized some limitations of conventional molecular techniques include the inability of such techniques to detect and quantify DNA from a species that is present in a complex sample in low abundance. Such detection becomes more challenging with an increasing concentration of foreign DNA in a sample. Increasing the sample volume further limits detection capabilities of molecular methods by diluting the concentration of the species of interest. Precise detection of a low concentration of DNA in a sample has many applications including, but not limited to liquid biopsy, microbiome therapeutics, and disease diagnostics.

Tumors release circulating tumor cells into the body. The circulating tumor cells and DNA coming from the cells are present in low abundance. Sensitive detection of DNA from circulating tumor cells can help detect early stage tumors, which can lead to diagnosing cancer at an early stage and potentially improve patient outcomes.

Detecting DNA from circulating tumor cells in blood is challenging, because there are billions of red blood cells and other DNA in every milliliter of blood, which causes high background noise for cell and DNA detection. In some embodiments, DNA present in low abundance in a blood sample is detected by performing a liquid biopsy on the blood sample following enhancement of the DNA of interest using one or more of the techniques described herein.

Similar to liquid biopsy or human microbiome samples, disease agents at an early stage of a disease are usually present in low abundance. DNA from a disease-causing agent may be hard to detect due to the presence of DNA noise arising from cells and other microbes. In some embodiments, DNA from a disease-causing agent is detected in low abundance in a liquid sample (e.g., blood, urine, saliva) following enhancement of the DNA using one or more of the techniques described herein.

Although the example microorganism described herein is bacteria, it should be appreciated that other microorganisms including, but not limited to, yeast, mold and viruses may also be detected in low abundance using one or more of the techniques for enrichment described herein.

As discussed in more detail below, enrichment of a target bacterial species is achieved by capturing bacteria on one or more electrodes of the microfluidic chip by applying an electric field in a preselected frequency range, washing away debris and non-target bacteria, and releasing captured components from the electrodes of the microfluidic chip.

Figure 16:
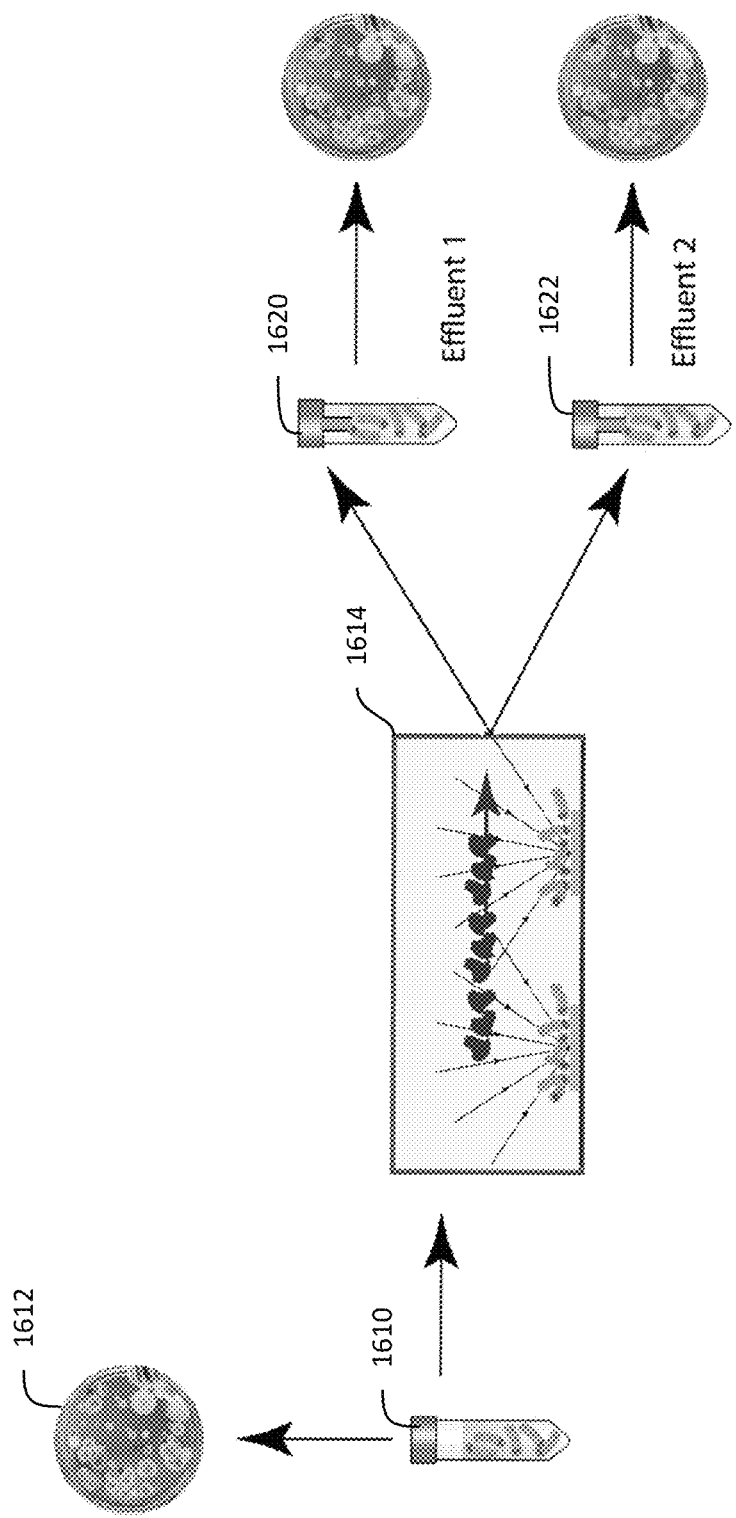
FIG. 16 schematically illustrates a process for enriching bacteria in a sample in accordance with some embodiments.

FIG. 16 schematically illustrates a process for enriching bacteria in accordance with some embodiments. An influent sample 1610 may contain multiple types of bacteria and non-bacterial components in different concentrations. Some bacteria may be at such low concentrations that they may not be detectable when cultured on a petri dish 1612, for example, using PCM. Influent sample 1610 is provided as input to a microfluidic channel of microfluidic device 1614 configured to capture bacteria on one or more electrodes using dielectrophoresis as the sample 1610 flows from an inlet of the microfluidic channel to an outlet of the microfluidic channel. Components of sample 1610 that are not captured by the electrode(s) in the microfluidic devices exit the outlet of the microfluidic channel and are collected in effluent sample container 1620 for further analysis, if desired. Following capture, the components (e.g., cells) are released from the electrodes and may be output from an outlet of the microfluidic channel into effluent sample container 1622 for further analysis, if desired.

Release of the captured components from the electrodes of the microfluidic chip may be accomplished in some embodiments using one or a combination of following techniques:

Captured target bacterial species are released from the electrodes to an outlet of a microfluidic channel by turning off the electric field. Turning off the electric field causes the dielectrophoresis force that captures bacteria to disappear. Fluid flow through the microfluidic channel washes off bacteria to an outlet of the microfluidic channel. At the outlet of the microfluidic channel bacteria are collected for DNA extraction or further processing for enrichment with bacterial culture or a growth-based technique.

Captured target bacterial species are released from the electrodes to an outlet of a microfluidic channel by applying a high frequency electric field to induce negative dielectrophoresis that repels captured cells including the target bacterial species from the electrodes. Fluid flow through the microfluidic channel washes off bacteria to an outlet of the microfluidic channel. At the outlet of a microfluidic channel bacteria are collected for DNA extraction or further processing for enrichment with bacterial culture or a growth-based technique.

Captured target bacterial species are released from the electrodes to an outlet of a microfluidic channel by flushing the microchannel of the microfluidic chip with a fluid at a high pressure. The fluid at a high pressure removes target bacterial species and DNA adherent to the surface of the electrodes to an outlet of the microfluidic channel. At the outlet of a microfluidic channel bacteria are collected for DNA extraction or further processing for enrichment with bacterial culture or a growth-based technique.

Figure 17A:
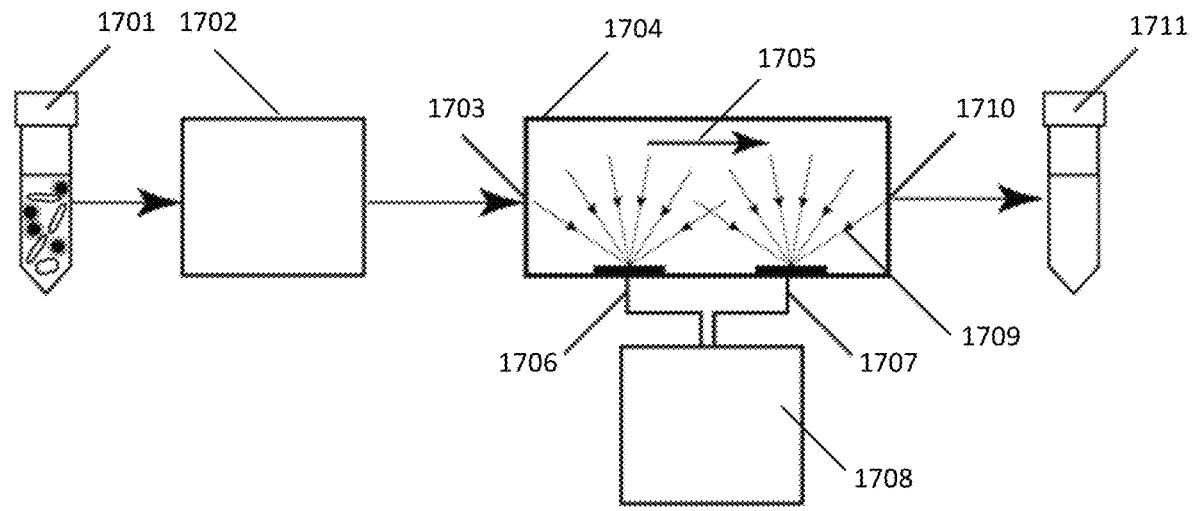
FIG. 17A illustrates a system configuration for enriching bacteria in a sample in accordance with some embodiments.
Figure 17B:
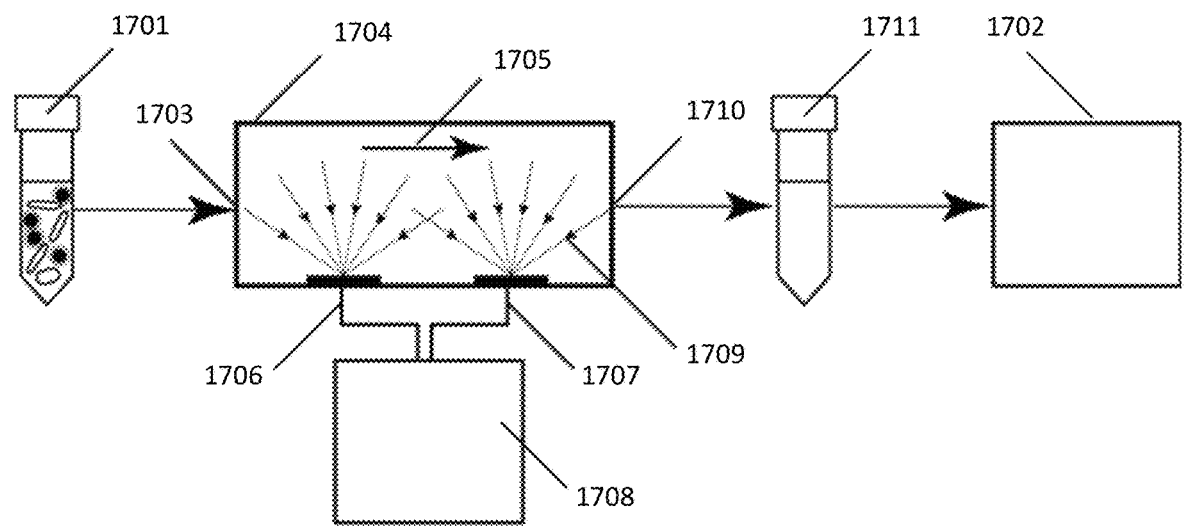
FIG. 17B illustrates an alternate system configuration for enriching bacteria in a sample in accordance with some embodiments.

FIGS. 17A and 17B schematically illustrate two configurations of a system for, among other things, detecting, quantifying, sorting, and enriching bacteria from microbiome samples in accordance with some embodiments. Influent sample 1701 contains a microbiome sample (e.g., a fecal sample, a skin swab sample, etc.). In some embodiments, a fecal sample is prepared for processing using the following process. The fecal sample is diluted 1:10 and emulsified mechanically preserving cell integrity. The emulsified sample is then filtered through a series of cell strainers including 100 um, 70 um, 40 um, 20 um and 10 um pore sizes. Several volumes of 0.001×PBS are passed through the cell strainers after the sample to wash the strainers of the sample and bring the final volume to a 1:100 dilution. Filtration is helpful to prevent particulates present in the fecal sample from clogging the microfluidic device. In some embodiments, a skin swab sample is prepared for processing using the systems shown in FIGS. 17A and 17B. One or more samples are collected from a donor using one or more skin swabs placed into a sterile buffer solution (e.g., 100 mL of 0.001×PBS). Between each swab collection, a container with the buffer solution may be agitated to ensure that the majority of the sample is transferred to the PBS media. The sample for processing may be aspirated (e.g., using a 27-gauge needle) from PBS media to high-pressure homogenize the sample. Aspiration in this manner breaks up clumps of skin cells in the sample without disturbing the native microbiota that may be adhered to the cells.

In the configuration shown in FIG. 17A, influent sample 1701 is connected to pump 1702, which is configured to cause the sample 1701 to flow through the inlet 1703 coupled to a microfluidic channel of the microfluidic device 1704. Arrow 1705 shows the direction of fluid flow through the microfluidic channel. The system also includes signal generator 1708 configured to generate a fixed signal or a variable frequency and amplitude signal having a voltage amplitude between 5V and 100V and frequency between 100 Hz and 400 MHz. As shown, signal generator 1708 is configured to generate electric signal 1706 applied to alternating (e.g., odd-numbered) rings of an electrode disposed within the microfluidic channel and electric signal 1707 applied to the other alternating (e.g., even-numbered) rings of the electrode and having an opposite polarity to electric signal 1706 or ground (e.g., 0V). Activation of the rings of the electrode create an electric field having a gradient 1709 pointing towards the electrode or electrode edge. As the sample 1701 flows through the microfluidic channel, bacteria of interest are captured onto the surface of the electrode by the electric field, whereas other components in the sample 1701 are not captured by the electric field and proceed to flow through output 1710 in the microfluidic channel which is coupled to effluent sample container 1711.

FIG. 17B shows a configuration similar to that described for FIG. 17A, but with pump 1702 located outside of the flow path, such that the sample 1701 does not pass through the pump during processing. In the configuration of FIG. 17B the pump creates sub-pressure in the system that causes the fluid flow through the microfluidic device as illustrated by arrow 1605.

In accordance with some embodiments, methods and apparatus for enriching organisms (e.g., bacteria) in a sample are provided, as shown in FIGS. 18A-D. Sample 1804 to be processed may include target bacterial species 1801, other bacterial species 1802 (e.g., Bacteroidetes for a fecal sample) and non-bacterial components 1803 (e.g., cells of human, plant or animal origin for a fecal sample; skin cells for a skin swab sample) as shown in FIG. 18A.

FIG. 18B shows a process by which bacteria in the influent sample 1804 are separated from non-bacterial microscopic components. The influent sample 1804 is provided to inlet 1805 of a microfluidic channel in microfluidic device 1806. As the sample 1804 flows through the microfluidic channel in the direction shown by arrow 1810, target bacterial species 1801 and other bacterial species 1802 are attracted to electrode 1809 due to a positive dielectrophoretic force exerted on the bacterial species as shown by the bacteria moving towards the electrode 1809 (see e.g., target bacterial species 1807 and other bacterial species 1808). In some embodiments, the amplitude and frequency of an AC voltage applied to the electrode 1809 to generate an applied electric field may be selected to attract and capture a broad range of bacteria (e.g., bacteria including, but not exclusive to, the target bacterial species 1801) on the electrode. For instance, the frequency of the applied AC voltage may be in the range 100 kHz-5 MHz and the amplitude of the applied AC voltage may be in the range 5V-100V peak-to-peak. Identifier 1811 in FIG. 18B schematically shows a trajectory of bacterial motion towards the electrode 1709 due to the applied electric field and identifier 1812 shows that non-bacterial components in the sample 1804 are not captured by the electric field, but instead flow toward outlet 1813 of the microfluidic channel to be collected in effluent sample container 1814. For instance, effluent sample container 1814 collects microscopic components and fluid that passes through the microfluidic device without being captured by the electrode 1809 while the electric field is turned on.

FIG. 18C shows a process for releasing the captured bacteria from the electrodes and collecting the released bacteria into effluent sample container 1818. One or more characteristics (e.g., amplitude, frequency) of the applied electric field 1815 may be changed to release the captured bacteria. For instance, the applied electric field 1815 may be altered by deactivating the electrodes by turning off the electric field or by applying an electric field with different characteristics (e.g., a high frequency electric field) that reduces the positive dielectrophoresis force or induces a negative dielectrophoresis force on the captured bacteria to repel the bacteria from the electrode surface. In some embodiments, the sample matrix may be exchanged to a controlled matrix (e.g., a buffer solution 0.001×PBS) prior to releasing the captured bacteria. Indicators 1816 and 1817 show the captured target bacterial species and the captured other bacterial species, respectively, moving away from the electrode in response to changes in the electric field. The fluid flow (e.g., including the introduced buffer solution) pushes the released bacteria toward effluent sample container 1818, which may be a different effluent sample container than the one used to collect waste during capture of the bacteria.

FIG. 18D shows a process for mechanically releasing captured components (e.g., bacterial cells) from the electrodes. A high-pressure wash solution 1820 is flushed through the microfluidic channel of the microfluidic device to mechanically release cells adhering to the electrodes (e.g., in the absence of the applied electric field. The released components are collected in the effluent wash sample container 1819.

In accordance with some embodiments, methods and apparatus for enriching organisms (e.g., a target bacterial species) in a sample are provided, as shown in FIGS. 19A-D.

Sample 1904 to be processed may include target bacterial species 1901, other bacterial species 1902 (e.g., Bacteroidetes for a fecal sample) and non-bacterial components 1903 (e.g., cells of human, plant or animal origin for a fecal sample; skin cells for a skin swab sample) as shown in FIG. 19A.

FIG. 19B shows a process by which target bacterial species 1901 in the influent sample 1904 are selectively separated from other bacterial species 1902 and non-bacterial components 1903 in the sample. The influent sample 1904 is provided to inlet 1905 of a microfluidic channel in microfluidic device 1906. As the sample 1904 flows through the microfluidic channel in the direction shown by arrow 1910, target bacterial species 1901 is attracted to electrode 1909 due to a positive dielectrophoretic force exerted on the target bacterial species as shown by the target bacterial species moving towards the electrode 1909 (see e.g., target bacterial species 1907). In some embodiments, the amplitude and frequency of an AC voltage applied to the electrode 1909 to generate an applied electric field may be selected to attract and selectively capture target bacterial species 1901 on the electrode without capturing other components. For instance, the frequency of the applied AC voltage may be in the range 2 MHz-5 MHz and the amplitude of the applied AC voltage may be in the range 5V-100V peak-to-peak. Identifier 1911 in FIG. 19B schematically shows a trajectory of the motion of the target bacterial species 1901 towards the electrode 1909 due to the applied electric field and identifier 1912 shows that other bacterial components 1902 and non-bacterial components 1903 in the sample 1904 are not captured by the electric field, but instead flow toward outlet 1913 of the microfluidic channel to be collected in effluent sample container 1914. For instance, effluent sample container 1914 collects microscopic components and fluid that passes through the microfluidic device without being captured by the electrode 1909 while the electric field is turned on.

FIG. 19C shows a process for releasing the captured target bacterial species from the electrodes and collecting the released bacteria into effluent sample container 1917. One or more characteristics (e.g., amplitude, frequency) of the applied electric field 1915 may be changed to release the captured target bacterial species. For instance, the applied electric field 1915 may be altered by deactivating the electrodes by turning off the electric field or by applying an electric field with different characteristics (e.g., a high frequency electric field) that reduces the positive dielectrophoresis force or induces a negative dielectrophoresis force on the captured bacteria to repel the bacteria from the electrode surface. In some embodiments, the sample matrix may be exchanged to a controlled matrix (e.g., a buffer solution 0.001×PBS) prior to releasing the captured bacteria. Indicator 1916 indicates that the captured target bacterial species moves away from the electrode in response to changes in the electric field. The fluid flow (e.g., including the introduced buffer solution) pushes the released bacteria toward effluent sample container 1917, which may be a different effluent sample container than the one used to collect waste during capture of the bacteria.

FIG. 19D shows a process for mechanically releasing captured any remaining target bacterial species 1901 from the electrodes. A high-pressure wash solution 1919 is flushed through the microfluidic channel of the microfluidic device to mechanically release cells adhering to the electrodes (e.g., in the absence of the applied electric field). The released components are collected in the effluent wash sample container 1918.

In accordance with some embodiments, methods and apparatus for enriching multiple organisms (e.g., a first target bacterial species and a second target bacterial species) in a sample are provided, as shown in FIGS. 20A-E. For instance, the processes described in FIGS. 18A-D and 19A-D may be combined. In some embodiments, the steps shown in FIGS. 19A-D may be repeated multiple times with multiple runs being applied sequentially on separate microfluidic devices or being applied on the same microfluidic device with an electrode geometry that allows for application of a sequence of electric field signals with controlled amplitude and/or frequency to separate multiple target bacterial species. Selectivity may be achieved by selectively releasing species that are not target species of interest.

Sample 2004 to be processed may include first target bacterial species 2001 (e.g., *E. coli* in a fecal sample), second target bacterial species 2002 (e.g., Bacteroidetes for a fecal sample) and non-bacterial components 2003 (e.g., cells of human, plant or animal origin for a fecal sample; skin cells for a skin swab sample) as shown in FIG. 20A.

FIG. 20B shows a process by which first target bacterial species 2001 in the influent sample 2004 is selectively separated from second target bacterial species 2002 and non-bacterial components 2003 in the sample. The influent sample 2004 is provided to inlet 2005 of a microfluidic channel in microfluidic device 2006. As the sample 2004 flows through the microfluidic channel in the direction shown by arrow 2010, both first target bacterial species 2001 and second target bacterial species 2002 are attracted to electrode 2009 due to a positive dielectrophoretic force exerted on the first and second target bacterial species as shown by the first and second target bacterial species moving towards the electrode 2009 (see e.g., first target bacterial species 2007 and second bacterial species 2008). In some embodiments, the amplitude and frequency of an AC voltage applied to the electrode 2009 to generate an applied electric field may be selected to attract both first target bacterial species 2001 and second target bacterial species 2002 on the electrode without capturing other components. For instance, the frequency of the applied AC voltage may be in the range 100 kHz-5 MHz and the amplitude of the applied AC voltage may be in the range 5V-100V peak-to-peak. Identifier 2011 in FIG. 20B schematically shows a trajectory of the motion of the target bacterial species towards the electrode 2009 due to the applied electric field and identifier 2012 shows that non-bacterial components 2003 in the sample 2004 are not captured by the electric field, but instead flow toward outlet 2013 of the microfluidic channel to be collected in effluent sample container 2014. For instance, effluent sample container 2014 collects microscopic components and fluid that passes through the microfluidic device without being captured by the electrode 2009 while the electric field is turned on.

FIG. 20C shows a process for releasing one of the two captured target bacterial species from the electrodes and collecting the released bacteria into effluent sample container 2018. One or more characteristics (e.g., amplitude, frequency) of the applied electric field 2015 may be changed to selectively release one of the two captured target bacterial species from the electrode. For instance, the applied electric field 2015 may be altered by applying an electric field with different characteristics (e.g., an electric field with a different frequency) that reduces the positive dielectrophoresis force or induces a negative dielectrophoresis force on either the first or the second captured bacteria to repel the bacteria from the electrode surface. In some embodiments, the sample matrix may be exchanged to a controlled matrix (e.g., a buffer solution 0.001×PBS) prior to releasing the captured bacteria. Indicator 2016 indicates that the captured second target bacterial species moves away from the electrode in response to changes in the electric field. The fluid flow (e.g., including the introduced buffer solution) pushes the released bacteria toward effluent sample container 2018, which is a different effluent sample container than the one used to collect waste during capture of the bacteria. Indicator 2016 indicates that the first target bacterial species remains captured by the electrode.

FIG. 20D shows a process for releasing the captured first target bacterial species from the electrodes and collecting the released bacteria into effluent sample container 2021. One or more characteristics (e.g., amplitude, frequency) of the applied electric field 2019 may be changed to release the captured first target bacterial species from the electrode. For instance, the applied electric field 2019 may be altered by turning the electric field off or by applying an electric field with different characteristics (e.g., an electric field with a different frequency) that reduces the positive dielectrophoresis force or induces a negative dielectrophoresis force on the captured first target bacterial species to repel the bacteria from the electrode surface. In some embodiments, the sample matrix may be exchanged to a controlled matrix (e.g., a buffer solution 0.001×PBS) prior to releasing the captured bacteria. Indicator 2010 indicates that the captured first target bacterial species moves away from the electrode in response to changes in the electric field. The fluid flow (e.g., including the introduced buffer solution) pushes the released bacteria toward effluent sample container 2021, which is a different effluent sample container than the one used to collect the second target bacterial species or waste collected during capture of the bacteria.

FIG. 20E illustrates a process for mechanically releasing captured any remaining bacterial species from the electrodes. A high-pressure wash solution 2023 is flushed through the microfluidic channel of the microfluidic device to mechanically release cells adhering to the electrodes (e.g., in the absence of the applied electric field). The released components are collected in the effluent wash sample container 2022.

Figure 21A:
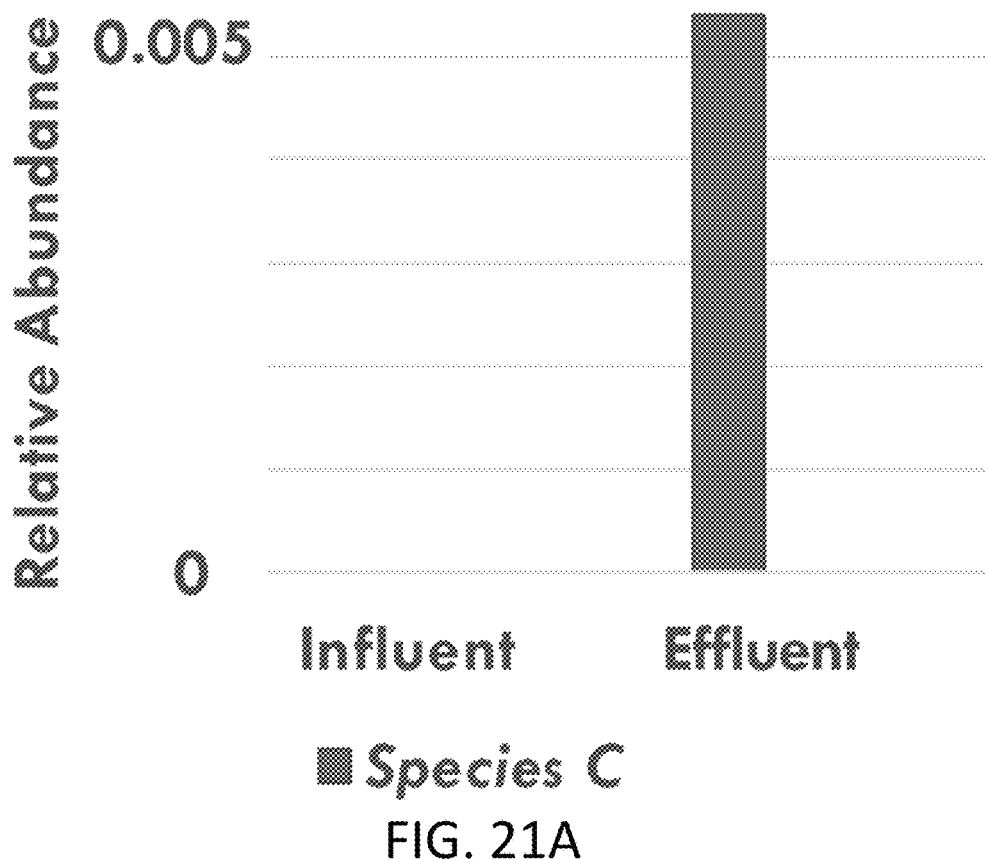
FIGS. 21A and 21B show results of bacteria enrichment experiments in accordance with some embodiments.

FIG. 21A illustrates results from an experiment in which the limit of detection for a target bacterial species C was enhanced. An aliquot of an influent sample was sequenced and all species having a relative abundance lower than 0.001 were considered not detectable. The results show no detectable presence of species C in the influent sample. The influent sample was then processed by the microfluidic device with an electric field having characteristics of frequency between 100 kHz-25 MHz at an amplitude between 5-50V and the effluent sample containing the released bacteria captured on the electrode was sequenced. The results show the relative abundance of species C being over 0.005, which is over five times above the detectable limit of 0.001. This result was repeated for four different bacterial species.

Figure 21B:
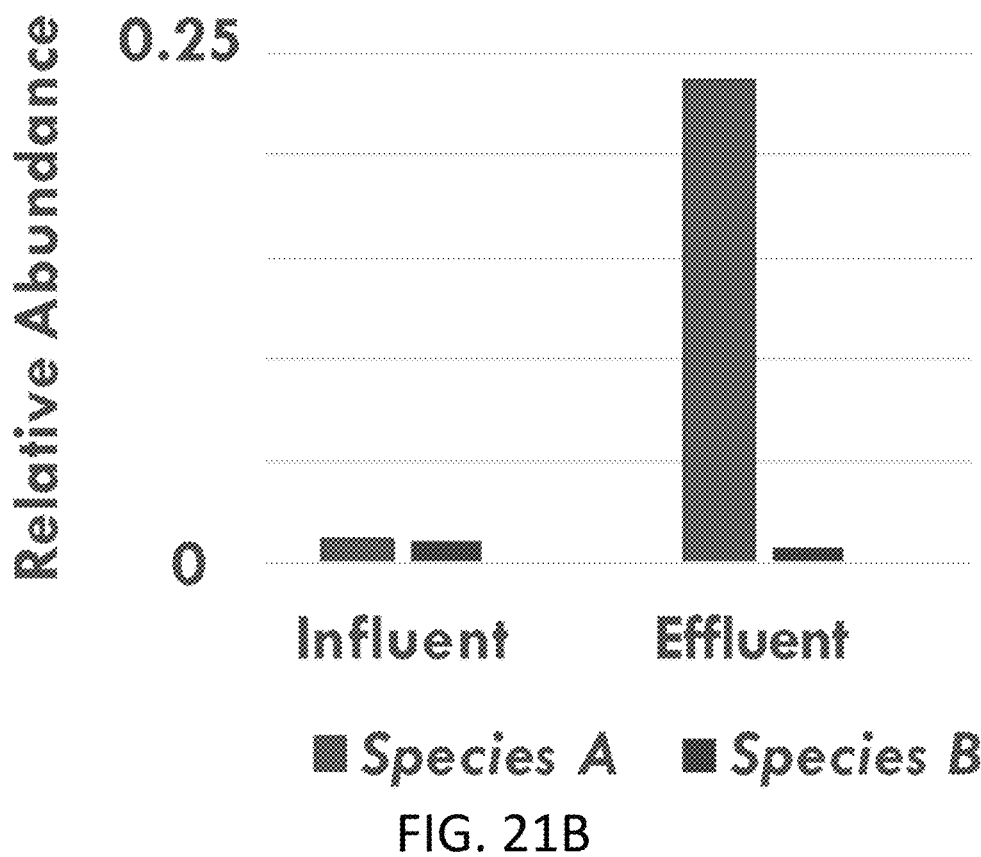

FIG. 21B illustrates results from another experiment in which the influent sample containing a mixture of bacterial species A and bacterial species B was sequenced. The results show the relative abundance of the two bacterial species is about equal in the influent sample (i.e., the sample prior to processing by the microfluidic device). The influent sample was then processed using the microfluidic device with an electric field having an operating frequency which selectively captured species A but not species B. The released effluent sample was sequenced and the results show the relative abundance of species A was close to 25 times higher than that of species B, demonstrating that some embodiments are capable of enriching, on a species level, about 25 times relative to the background in the sample.

Microbiome therapeutics often consist of lyophilized consortia of multiple bacterial strains. To preserve therapeutic properties, it is important that manufacturers ensure reproducibility of the manufacturing process. The lyophilized bacterial strains need to yield live bacteria after the therapeutic is administered to a patient. This requires control and reproducibility of a manufacturing process. It also requires ensuring that each batch of microbiome drugs has the same ratio and viability of the strains within a consortium.

Controlling the manufacturing processes using current methods is challenging. Bacterial culture requires at least two days for most of the bacterial strains used in such processes, which results in process delays due to the time it takes to receive feedback on the process. Additionally, it can be challenging to ensure reproducibility of manufacturing processes where bacterial levels within a bioreactor can vary by about 100 from batch to batch.

Stain based methods and flow cytometry suffer from high error rates. Additionally, molecular methods do not differentiate between live and dead bacteria. Some embodiments relate to an accurate and real time in-process test that enables more efficient in-process control and ensure reproducibility of manufacturing within an acceptable +/−0.5 log variability range.

Manufacturing microbiome therapeutics requires controlling the composition of the final product. The final product release test requires quantifying the number of bacteria in a pill after lyophilization by strain and also the number of viable bacteria. Bacterial strains included in a microbiome therapeutic are often closely related and cannot be grown on selective media. This can make it challenging to use bacterial culture as a method for the final product release test. Some embodiments address at least some of these challenges by (1) enabling differentiation and/or quantification of live and dead bacteria in a sample and (2) enabling differentiation and/or quantification of bacteria from a complex mixture.

Some embodiments relate to methods and apparatus for sorting multiple bacterial species in a complex sample using dielectrophoresis. The inventors have recognized and appreciated that different bacterial species are attracted (due to positive dielectrophoresis) or repulsed (due to negative dielectrophoresis) from the surface of an electrode based on the frequency of an AC voltage applied to the electrode. Within certain frequency ranges (e.g., 900 Hz-2 MHz) multiple species of bacteria respond similarly, being attracted to the electrode due to positive dielectrophoresis. Within other higher frequency ranges some bacterial species experience positive dielectrophoresis whereas other bacterial species experience negative dielectrophoresis. The inventors have recognized that this differential response, especially at higher frequencies, may be used to sort bacteria by selecting stimulation frequencies in which one bacterial species is attracted to the electrode and one or more other bacterial species are repulsed.

Figure 22A:
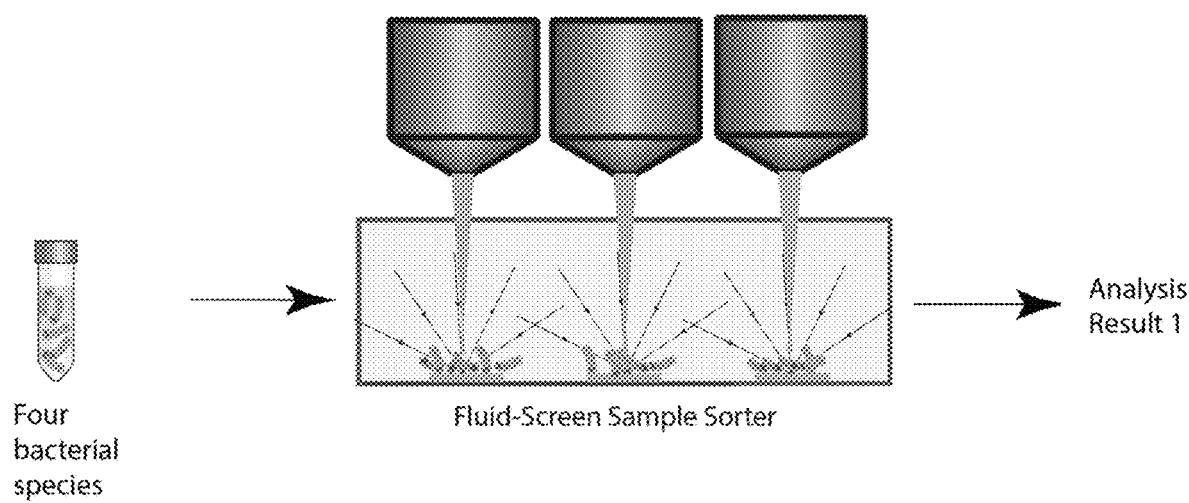
FIG. 22A schematically illustrates a system for sorting bacteria from a complex sample including multiple bacterial species in accordance with some embodiments.

FIG. 22A illustrates a schematic of a microfluidic system in which a complex mixture of four bacterial species is sorted in accordance with some embodiments. The microfluidic device shown in FIG. 22A includes multiple electrodes, each of which can be tuned to provide an electric field that selectively captures one of the bacterial species in the complex mixture on the electrode while other components of the mixture pass to the next electrode in the sequential chain. By using three electrodes, each tuned with different electronic conditions, the four bacterial species in the complex mixture can be separated.

Figure 22B:
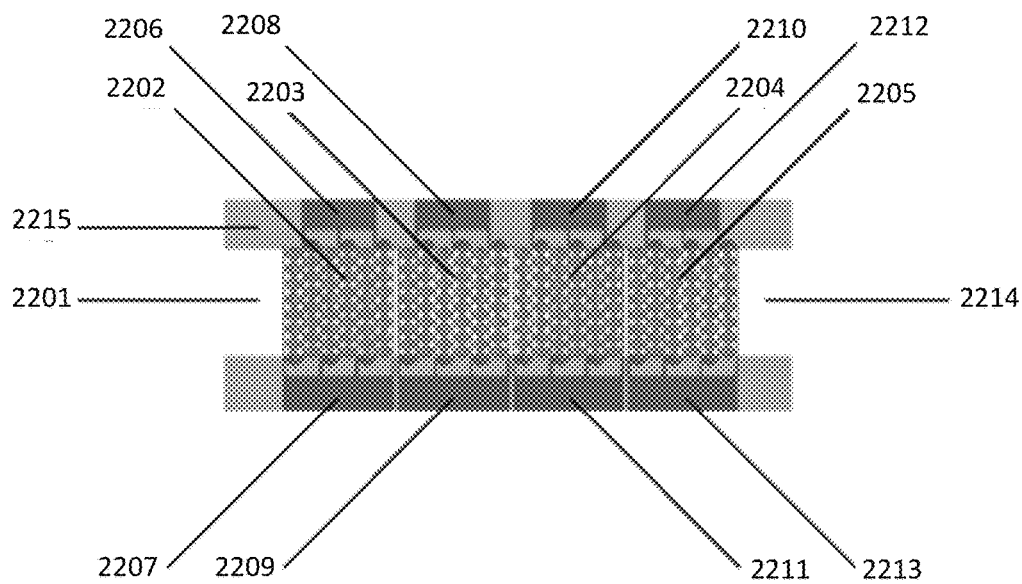
FIG. 22B schematically illustrates a microfluidic device having four electrode systems for sorting bacteria from a complex sample in accordance with some embodiments.

FIG. 22B illustrates a top view of an example microfluidic device including four electrode systems that may be used to perform bacteria sorting in accordance with some embodiments. The microfluidic system includes a microfluidic channel having an inlet 2201, an outlet 2214 and a wall 2215. The microfluidic channel may have any suitable dimensions. Arranged between inlet 2201 and outlet 2214 along the fluid flow path are first electrode system 2202, second electrode system 2203, third electrode system 2204 and fourth electrode system 2205. First electrode system 2202 is coupled to electric contact 2206 configured to supply an AC voltage (voltage: +V1, frequency: f1) and electric contact 2207 configured to supply an AC voltage (voltage: −V1 (or ground), frequency: f1). Second electrode system 2203 is coupled to electric contact 2208 configured to supply an AC voltage (voltage: +V2, frequency: f2) and electric contact 2209 configured to supply an AC voltage (voltage: −V2 (or ground), frequency: f2). Third electrode system 2204 is coupled to electric contact 2210 configured to supply an AC voltage (voltage: +V3, frequency: f3) and electric contact 2211 configured to supply an AC voltage (voltage: −V3 (or ground), frequency: f3). Fourth electrode system 2204 is coupled to electric contact 2212 configured to supply an AC voltage (voltage: +V4, frequency: f4) and electric contact 2213 configured to supply an AC voltage (voltage: −V4 (or ground), frequency: f4).

Figure 22C:
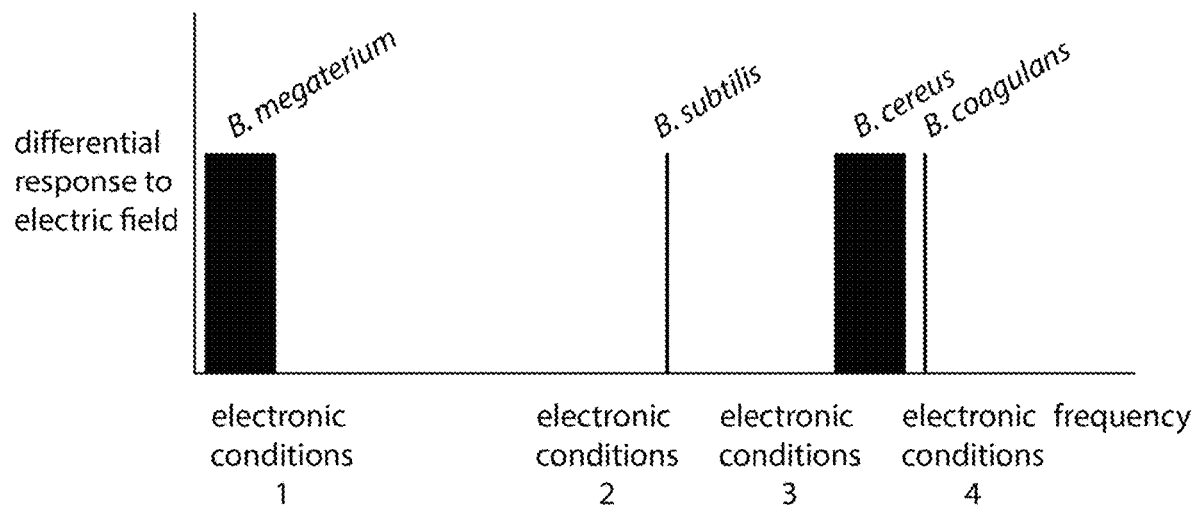
FIG. 22C illustrates cross-over frequencies for different bacterial species in a complex sample that may be used to sort bacteria in accordance with some embodiments.

In an experiment, the results of which are shown in FIG. 22C, it was demonstrated that a microfluidic device designed in accordance with the techniques described herein can discriminate between four closely related bacterial species—*B. subtilis, B. cereus, B. coagulans* and *B. megaterium* by changing the frequency characteristic of the applied electric field when the amplitude of the applied AC voltage is held constant. Each bacterial species was suspended separately in tested buffer (PBS 1:1000 in deionized water) and stained with SybrGreen I dye. After 30 minutes of incubation in darkness 2 μL of the sample was loaded onto a microfluidic chip designed in accordance with the techniques described herein and was visualized using the static system 500 described in connection with FIG. 5. The frequency of the applied electric field was swept from a low frequency to a high frequency, and when certain frequencies were reached particular bacterial species responded to the electric field in characteristic manner in which loosely floating bacteria (when electric field is off) were forced from any area of chip to the edges of electrodes (when electric field is on), thereby exhibiting positive dielectrophoresis. When the electric field was turned off the bacteria were released from the edges of the electrode. In particular, the plot in FIG. 22C shows that the closely related species respond to the electric field in a differential way and these electronic conditions are characteristic for specific species.

In particular, FIG. 22C illustrates a plot of four different bacterial species and their respective cross-over frequency responses for a constant amplitude AC voltage. For each of the bacterial species, its cross-over frequency is the frequency at which the bacterial species switches from exhibiting positive dielectrophoresis below the cross-over frequency and negative dielectrophoresis above the cross-over frequency. For instance, as shown in FIG. 22C, the bacterial species *B. megaterium* has a lower cross-over frequency than *B. subtilis*, which has a lower cross-over frequency than *B. cerus*, which has a lower cross-over frequency than *B. coagulans*. By setting the frequency of the applied electric field to a frequency that falls between two cross-over frequencies of different bacterial species, one species will be attracted to the electrode via positive dielectrophoresis while the other species will be repelled via negative dielectrophoresis, thereby enabling separation of the two species.

In accordance with some embodiments, methods and apparatus for separating organisms (e.g., bacteria) in a sample are provided, as shown in FIGS. 23A-C. An influent sample 2305 to be processed may be, for example, a microbiome sample containing a bacterial consortium with multiple bacterial strains. For instance, sample 2305 may include a first target bacterial species 2301 (e.g., *E. coli*), a second target bacterial species 2302 (e.g., *B. cerus*) and a third target bacterial species 2303 (e.g., *B. megaterium*) as shown in FIG. 23A.

FIG. 23B shows a process by which bacteria in the sample 2305 are separated and captured on different electrode systems. The sample 2305 is provided to inlet 2304 of a microfluidic channel in microfluidic device 2306. As the sample 2305 flows through the microfluidic channel in the direction shown by arrow 2313, the first target bacterial species is captured using positive dielectrophoresis by a first electrode system 2307 being driven by an AC voltage having amplitude and frequency characteristics (V1;f1). In particular, the AC voltage signal is applied to electrodes of opposite polarity in first electrode system 2307 as (+V1, f1; −V1, f1) or (+V1, f1; 0V) to generate an electric field 2310 which acts to capture the first bacterial species on the surface of the electrodes in first electrode system 2307, as illustrated by indicator 2314). As illustrated by indicators 2315 and 2316, the second target bacterial species and the third target bacterial species, respectively, are not captured by the first electrode system 2307, but continue flowing through the microfluidic device 2306.

As the sample 2305 flows through the microfluidic channel in the direction shown by arrow 2313, the second target bacterial species is captured using positive dielectrophoresis by a second electrode system 2308 being driven by an AC voltage having amplitude and frequency characteristics (V2; f2). In particular, the AC voltage signal is applied to electrodes of opposite polarity in second electrode system 2308 as (+V2, f2; −V2, f2) or (+V2, f2; 0V) to generate an electric field 2311 which acts to capture the second bacterial species on the surface of the electrodes in second electrode system 2308, as illustrated by indicator 2317). As illustrated by indicator 2318, the third target bacterial species is not captured by the second electrode system 2308, but continues flowing through the microfluidic device 2306.

As the sample 2305 flows through the microfluidic channel in the direction shown by arrow 2313, the third target bacterial species is captured using positive dielectrophoresis by a third electrode system 2309 being driven by an AC voltage having amplitude and frequency characteristics (V3; f3). In particular, the AC voltage signal is applied to electrodes of opposite polarity in second electrode system 2309 as (+V3, f3; −V3, f3) or (+V3, f3; 0V) to generate an electric field 2312 which acts to capture the third bacterial species on the surface of the electrodes in third electrode system 2309, as illustrated by indicator 2319).

Any remaining components not captured by one of the electrode systems flow through outlet 2320 into effluent sample container 2321. For instance, the effluent sample may contain microscopic components and fluid that passes the microfluidic device while the electric fields are turned on. It should be appreciated that although a three electrode system has been illustrated, any number of electrode systems (including fewer or more electrode systems) to separate any number of organisms in the sample, and embodiments are not limited in this respect.

FIG. 23C shows a process for quantifying captured bacteria, selectively releasing the captured bacteria from the electrodes, and collecting the released bacteria into effluent sample container 2332. Influent sample container 2322 containing a fluid may be connected to the inlet 2304 of the microfluidic device. For instance, the fluid in influent sample container 2322 may be used to flush the microfluidic device with a controlled matrix such as a buffer solution. Additionally or alternatively, the microfluidic device may be flushed with a fluorescent stain or a label and incubated for a period of time.

As shown, the system includes optical system 2329 configured to capture an image of bacteria captured on an electrode. For instance, optical system 2329 may include an optical sensor with a fluorescent light detector, such as a fluorescent microscope or light emitting diode (LED) light source 2330 with an objective and a detector. Light source 2330 may be configured to excite a fluorophore in the labeled bacteria. It should be appreciated that not all embodiments use fluorescent labeling of bacteria or other captured organism, as some embodiments are configured to generate bright field images.

Optical system 2329 may be configured to sequentially image the first electrode system, the second electrode system, and the third electrode system to record, for each electrode system, a fluorescent signal and/or an image corresponding to the electrode system while the fluorescently stained target bacterial species remain captured by the electrodes in the electrode system (as shown by indicators 2326, 2327 and 2328). Computer 2331 or another image processor is configured to process images captured by optical system 2329 to recognize bacteria in the captured images and to quantify a number of bacteria in the images.

One or more characteristics (e.g., amplitude, frequency) of the applied electric fields generated by the electrode systems 2323, 2324 and 2325 may be changed to release the captured bacteria from the electrodes. For instance, one or more of the applied electric fields may be altered by deactivating the electrodes of a corresponding electrode system by turning off the electric field or by applying an electric field with different characteristics (e.g., a high frequency electric field) that reduces the positive dielectrophoresis force or induces a negative dielectrophoresis force on the captured bacteria to repel the bacteria from the electrode surface of the electrode system. In some embodiments, the sample matrix may be exchanged to a controlled matrix (e.g., a buffer solution 0.001×PBS) prior to releasing the captured bacteria. Fluid flow in the microfluidic device may push the released bacteria toward effluent sample container 2332, which may be a different effluent sample container than the one used to collect waste during capture of the bacteria.

In accordance with some embodiments, methods and apparatus for separating organisms (e.g., bacteria) in a sample are provided, as shown in FIGS. 24A-C. An influent sample 2405 to be processed may be, for example, a microbiome sample containing a bacterial consortium with multiple bacterial strains and other particles. For instance, sample 2405 may include a first target bacterial species 2401 (e.g., *E. coli*), a second target bacterial species 2402 (e.g., *B. cerus*), a third target bacterial species 2403 (e.g., *B. megaterium*), and non-bacterial components or bacteria that are not of interest in a sample (e.g., cells of human, plant or animal origin in a fecal sample, skin cells in a skin swab sample, or components of growth media from a bioreactor), as shown in FIG. 24A.

FIG. 24B shows a process by which bacteria in the sample 2405 are separated from the non-bacterial components and are captured on different electrode systems. The sample 2405 is provided to an inlet of a microfluidic channel in microfluidic device 2406. As the sample 2405 flows through the microfluidic channel in the direction shown by arrow 2413, the first target bacterial species is captured using positive dielectrophoresis by a first electrode system 2407 being driven by an AC voltage having amplitude and frequency characteristics (V1;f1). In particular, the AC voltage signal is applied to electrodes of opposite polarity in first electrode system 2407 as (+V1, f1; −V1, f1) or (+V1, f1; 0V) to generate an electric field 2410 which acts to capture the first bacterial species on the surface of the electrodes in first electrode system 2407, as illustrated by indicator 2414). As illustrated by indicators 2415, 2416, and 2420, the second target bacterial species, the third target bacterial species, and the other components, respectively, are not captured by the first electrode system 2407, but continue flowing through the microfluidic device 2406.

As the sample 2405 flows through the microfluidic channel in the direction shown by arrow 2413, the second target bacterial species is captured using positive dielectrophoresis by a second electrode system 2408 being driven by an AC voltage having amplitude and frequency characteristics (V2; f2). In particular, the AC voltage signal is applied to electrodes of opposite polarity in second electrode system 2408 as (+V2, f2; −V2, f2) or (+V2, f2; 0V) to generate an electric field 2411 which acts to capture the second bacterial species on the surface of the electrodes in second electrode system 2408, as illustrated by indicator 2417). As illustrated by indicators 2418 and 2421, the third target bacterial species and the other components, respectively, are not captured by the second electrode system 2408, but continues flowing through the microfluidic device 2406.

As the sample 2405 flows through the microfluidic channel in the direction shown by arrow 2413, the third target bacterial species is captured using positive dielectrophoresis by a third electrode system 2409 being driven by an AC voltage having amplitude and frequency characteristics (V3; f3). In particular, the AC voltage signal is applied to electrodes of opposite polarity in second electrode system 2409 as (+V3, f3; −V3, f3) or (+V3, f3; 0V) to generate an electric field 2412 which acts to capture the third bacterial species on the surface of the electrodes in third electrode system 2409, as illustrated by indicator 2419).

Any remaining components not captured by one of the electrode systems flow through an outlet of the microfluidic device into effluent sample container 2423. For instance, the effluent sample may contain microscopic components and fluid that passes the microfluidic device while the electric fields are turned on. It should be appreciated that although a three electrode system has been illustrated, any number of electrode systems (including fewer or more electrode systems) to separate any number of organisms in the sample, and embodiments are not limited in this respect.

FIG. 24C shows a process for quantifying captured bacteria, selectively releasing the captured bacteria from the electrodes, and collecting the released bacteria into effluent sample container 2432. Influent sample container 2434 containing a fluid may be connected to the inlet of the microfluidic device. For instance, the fluid in influent sample container 2434 may be used to flush the microfluidic device with a controlled matrix such as a buffer solution. Additionally or alternatively, the microfluidic device may be flushed with a fluorescent stain or a label and incubated for a period of time.

As shown, the system includes optical system 2429 configured to capture an image of bacteria captured on an electrode. For instance, optical system 2429 may include an optical sensor with a fluorescent light detector, such as a fluorescent microscope or light emitting diode (LED) light source 2430 with an objective and a detector. Light source 2430 may be configured to excite a fluorophore in the labeled bacteria. It should be appreciated that not all embodiments use fluorescent labeling of bacteria or other captured organism, as some embodiments are configured to generate bright field images.

Optical system 2429 may be configured to sequentially image the first electrode system, the second electrode system, and the third electrode system to record, for each electrode system, a fluorescent signal and/or an image corresponding to the electrode system while the fluorescently stained target bacterial species remain captured by the electrodes in the electrode system (as shown by indicators 2426, 2427 and 2428). Computer 2431 or another image processor is configured to process images captured by optical system 2429 to recognize bacteria in the captured images and to quantify a number of bacteria in the images.

One or more characteristics (e.g., amplitude, frequency) of the applied electric fields generated by the electrode systems 2433, 2424 and 2425 may be changed to release the captured bacteria from the electrodes. For instance, one or more of the applied electric fields may be altered by deactivating the electrodes of a corresponding electrode system by turning off the electric field or by applying an electric field with different characteristics (e.g., a high frequency electric field) that reduces the positive dielectrophoresis force or induces a negative dielectrophoresis force on the captured bacteria to repel the bacteria from the electrode surface of the electrode system. In some embodiments, the sample matrix may be exchanged to a controlled matrix (e.g., a buffer solution 0.001×PBS) prior to releasing the captured bacteria. Fluid flow in the microfluidic device may push the released bacteria toward effluent sample container 2432, which may be a different effluent sample container than the one used to collect waste during capture of the bacteria.

In accordance with some embodiments, methods and apparatus for separating live from dead organisms (e.g., bacteria) in a sample are provided, as shown in FIGS. 25A-C. An influent sample 2503 to be processed may include a first target bacterial species 2501 (e.g., live *E. coli*) and a second target bacterial species 2502 (e.g., dead *E. coli*) as shown in FIG. 25A.

FIG. 25B shows a process by which live and dead bacteria in the sample 2503 are separated and captured on different electrode systems. The sample 2503 is provided to inlet 2504 of a microfluidic channel in microfluidic device 2506. As the sample 2503 flows through the microfluidic channel in the direction shown by arrow 2505, the first target bacterial species is captured using positive dielectrophoresis by a first electrode system 2507 being driven by an AC voltage having amplitude and frequency characteristics (V1; f1). In particular, the AC voltage signal is applied to electrodes of opposite polarity in first electrode system 2507 as (+V1, f1; −V1, f1) or (+V1, f1; 0V) to generate an electric field 2509 which acts to capture the first target bacterial species on the surface of the electrodes in first electrode system 2507, as illustrated by indicator 2511). As illustrated by indicator 2512, the second target bacterial species is not captured by the first electrode system 2507, but continues flowing through the microfluidic device 2506.

As the sample 2503 flows through the microfluidic channel in the direction shown by arrow 2505, the second target bacterial species is captured using positive dielectrophoresis by a second electrode system 2508 being driven by an AC voltage having amplitude and frequency characteristics (V2; f2). In particular, the AC voltage signal is applied to electrodes of opposite polarity in second electrode system 2508 as (+V2, f2; −V2, f2) or (+V2, f2; 0V) to generate an electric field 2510 which acts to capture the second bacterial species on the surface of the electrodes in second electrode system 2508, as illustrated by indicator 2513).

Any remaining components not captured by one of the electrode systems flow through outlet 25140 into effluent sample container 2515. For instance, the effluent sample may contain microscopic components and fluid that passes the microfluidic device while the electric fields are turned on.

FIG. 25C shows a process for quantifying captured bacteria, selectively releasing the captured bacteria from the electrodes, and collecting the released bacteria into effluent sample container 2524. Influent sample container 2516 containing a fluid may be connected to the inlet of the microfluidic device. For instance, the fluid in influent sample container 2516 may be used to flush the microfluidic device with a controlled matrix such as a buffer solution. Additionally or alternatively, the microfluidic device may be flushed with a fluorescent stain or a label and incubated for a period of time.

As shown, the system includes optical system 2521 configured to capture an image of bacteria captured on an electrode. For instance, optical system 2521 may include an optical sensor with a fluorescent light detector, such as a fluorescent microscope or light emitting diode (LED) light source 2522 with an objective and a detector. Light source 2522 may be configured to excite a fluorophore in the labeled bacteria. It should be appreciated that not all embodiments use fluorescent labeling of bacteria or other captured organism, as some embodiments are configured to generate bright field images.

Optical system 2521 may be configured to sequentially image the first electrode system and the second electrode system to record, for each electrode system, a fluorescent signal and/or an image corresponding to the electrode system while the fluorescently stained target bacterial species remains captured by the electrodes in the electrode system (as shown by indicators 2519 and 2520). Computer 2523 or another image processor is configured to process images captured by optical system 2521 to recognize bacteria in the captured images and to quantify a number of bacteria in the images.

One or more characteristics (e.g., amplitude, frequency) of the applied electric fields generated by the electrode systems 2517 and 2518 may be changed to release the captured bacteria from the electrodes. For instance, one or more of the applied electric fields may be altered by deactivating the electrodes of a corresponding electrode system by turning off the electric field or by applying an electric field with different characteristics (e.g., a high frequency electric field) that reduces the positive dielectrophoresis force or induces a negative dielectrophoresis force on the captured bacteria to repel the bacteria from the electrode surface of the electrode system. In some embodiments, the sample matrix may be exchanged to a controlled matrix (e.g., a buffer solution 0.001×PBS) prior to releasing the captured bacteria. Fluid flow in the microfluidic device may push the released bacteria toward effluent sample container 2524, which may be a different effluent sample container than the one used to collect waste during capture of the bacteria.

In accordance with some embodiments, methods and apparatus for separating live from dead organisms (e.g., bacteria) in a sample are provided, as shown in FIGS. 26A-C. An influent sample 2603 to be processed may include a first target bacterial species 2601 (e.g., live *E. coli*) and a second target bacterial species 2602 (e.g., dead *E. coli*) as shown in FIG. 26A.

FIG. 26B shows a process by which live and dead bacteria in the sample 2603 are separated and either the live bacteria or the dead bacteria are captured on an electrode system. The sample 2603 is provided to inlet 2604 of a microfluidic channel in microfluidic device 2609. The first target bacterial species in the sample 2603 is captured using positive dielectrophoresis by an electrode system 2605 being driven by an AC voltage having amplitude and frequency characteristics (V1;f1). In particular, the AC voltage signal is applied to electrodes of opposite polarity in electrode system 2605 as (+V1, f1; −V1, f1) or (+V1, f1; 0V) to generate an electric field 2606, which acts to capture the first target bacterial species on the surface of the electrodes in electrode system 2605, as illustrated by indicator 2607). As illustrated by indicator 2608, the AC voltage characteristics are selected such that the second target bacterial species is not captured by the electrode system 2605.

As shown, the system includes optical system 2611 configured to capture an image of bacteria captured on an electrode. For instance, optical system 2611 may include an optical sensor with a fluorescent light detector, such as a fluorescent microscope or light emitting diode (LED) light source 2610 with an objective and a detector. Light source 2610 may be configured to excite a fluorophore in the labeled bacteria. It should be appreciated that not all embodiments use fluorescent labeling of bacteria or other captured organism, as some embodiments are configured to generate bright field images.

Optical system 2611 may be configured to image electrode system 2605 to record a fluorescent signal and/or an image corresponding to the electrode system while the fluorescently stained target bacterial species remains captured by the electrodes in the electrode system (as shown by indicator 2615). Computer 2612 or another image processor is configured to process image(s) captured by optical system 2611 to recognize bacteria in the captured image(s) and to quantify a number of bacteria in the image(s).

FIG. 26C shows a process for capturing both the first target bacterial species and the second target bacterial species on the electrode system. Both the first target bacterial species and the second target bacterial species are captured using positive dielectrophoresis by an electrode system 2613 being driven by an AC voltage having amplitude and frequency characteristics (V2;f2). In particular, the AC voltage signal is applied to electrodes of opposite polarity in electrode system 2613 as (+V2, f2; −V2, f2) or (+V2, f2; 0V) to generate an electric field 2614, which acts to capture both the first target bacterial species and the second target bacterial species on the surface of the electrodes in electrode system 2613, as illustrated by indicator 2615). In some embodiments V2 is between 1 V and 100V and f2 is between 100 kHz and 20 MHz.

As shown, the system includes optical system 2616 configured to capture an image of bacteria captured on an electrode. For instance, optical system 2616 may include an optical sensor with a fluorescent light detector, such as a fluorescent microscope or light emitting diode (LED) light source 2617 with an objective and a detector. Light source 2617 may be configured to excite a fluorophore in the labeled bacteria. It should be appreciated that not all embodiments use fluorescent labeling of bacteria or other captured organism, as some embodiments are configured to generate bright field images.

Optical system 2616 may be configured to image electrode system 2613 to record a fluorescent signal and/or an image corresponding to the electrode system while the fluorescently stained target bacterial species remains captured by the electrodes in the electrode system (as shown by indicator 2615). Computer 2618 or another image processor is configured to process image(s) captured by optical system 2616 to recognize bacteria in the captured image(s) and to quantify a number of bacteria in the image(s).

In another experiment, bacteria from two different genera suspended in (PBS 1:1000 in deionized water) and stained with SybrGreen I were shown to respond to the applied electric field differently. *E. coli* and *B. megaterium* were suspended in tested buffer, stained with SybrGreen I dye separately and after 30 minutes of incubation in darkness were combined and loaded to the microfluidic chip described previously in system 500 of FIG. 5. When certain voltage and frequency for *B. megaterium* were reached bacteria responded to the electric field in characteristic manner by being captured on the surface of the electrode, which is characteristic of positive dielectrophoresis, while *E. coli* was not attracted to the electrodes. When electronic conditions were specifically changed, *E. coli* also responded by responding to the electric field and were attracted to the edges of electrodes, thereby exhibiting positive dielectrophoresis.

The same set of experiments was performed for mixtures of *E. coli/B. cereus*, *E. coli/B. coagulans* and *E. coli/B. subtilis*. For each successive pair of Gram (−) and Gram (+) bacteria, the same behavior was observed. Depending on electrical conditions was capture *Bacillus* spp. or both genera.

In subsequent experiments it was demonstrated that even closely related species respond to the electric field differently. The *B. cereus* and *B. coagulans* were suspended in tested buffer, stained with SybrGreen I dye separately and after 30 minutes of incubation in darkness were combined and loaded to the microfluidic chip and visualized using the static system 500 shown in FIG. 5. When a certain voltage and frequency for *B. cereus* was reached, bacteria responded to the electric field in a characteristic manner, while *B. coagulans* was not attracted to the electrodes. When electronic conditions were changed, *B. coagulans* also responded to the electric field and was captured on the edges of electrodes.

The same set of experiments was also performed for mixtures of *B. megaterium* and *B. subtilis*. As described above at a certain voltage and frequency *B. megaterium* was captured while *B. subtilis* did not respond to the electric field. The change in electrical conditions resulted in capture both *B. megaterium* and *B. subtilis*.

Figure 27A:
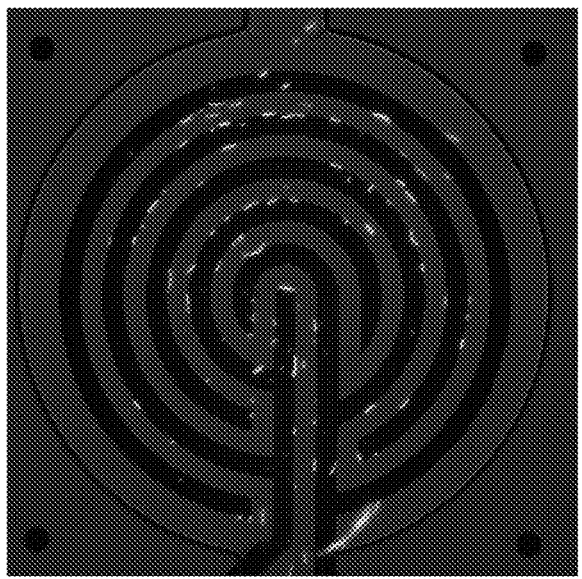
FIGS. 27A-27E illustrate images of selective capture of bacterial species by tuning an electric field based on cross-over frequencies for different bacterial species in accordance with some embodiments.
Figure 27B:
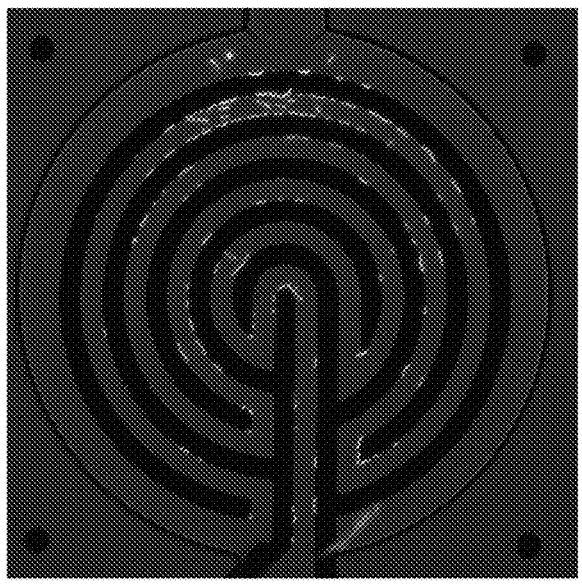
Figure 27C:
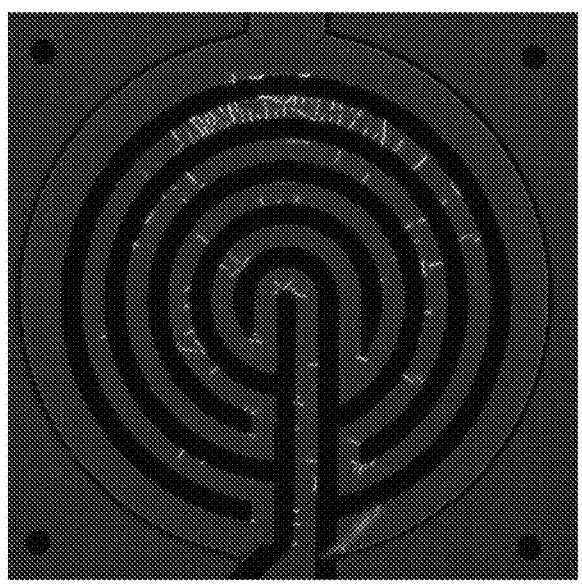
Figure 27D:
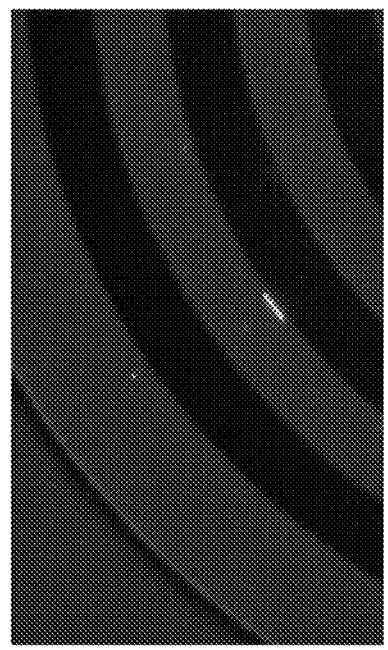

FIGS. 27A-27E illustrate images showing selective capture of *B. megaterium* (shown as long strands) and *B. subtilis* (shown as dots) in accordance with the techniques described above. FIG. 27A illustrates an image taken at electric field settings (90 MHz, 20 Vpp) that correspond to positive dielectrophoresis for *B. megaterium*. *B. megaterium* bacteria are captured at the electrode edges, while *B. subtilis* is not captured, but instead floats above the electrodes. FIG. 27D illustrates a zoomed in version of the electrode in which the electric field was tuned to capture *B. megaterium* (which is in focus in the image, but not *B. subtilis* (which is out of focus).

Figure 27E:
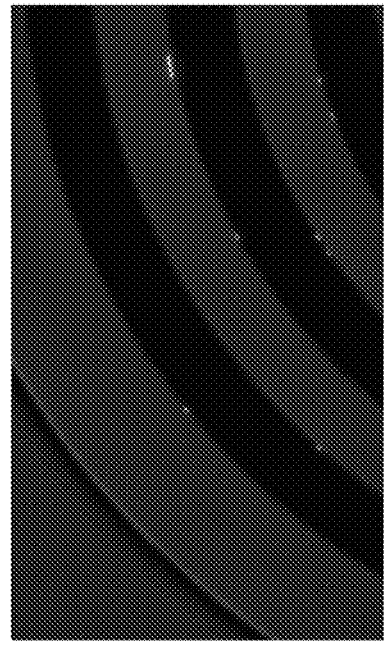

FIG. 27B illustrates an image taken when the electric field (20 MHz, 20 Vpp) was turned on as to achieve positive dielectrophoresis for *B. megaterium* and *B. subtilis*. Both species are captured on the electrode edges. *B. megaterium* orientation under both electronic conditions in FIG. 27A and FIG. 27B is tangential (parallel) to the electrode edge. FIG. 27E illustrates a zoomed in version of the electrode in which the electric field is tuned such that both *B. megaterium* and *B. subtilis* are captured.

FIG. 27C illustrates an image taken when the frequency of the electric field is adjusted in the low frequency range (1 MHz, 20 Vpp). Only *B. subtilis* remains captured on the edges of the electrode while *B. megaterium* switched orientation from tangential (parallel) to orthogonal to the electrode edge.

Figure 28B:
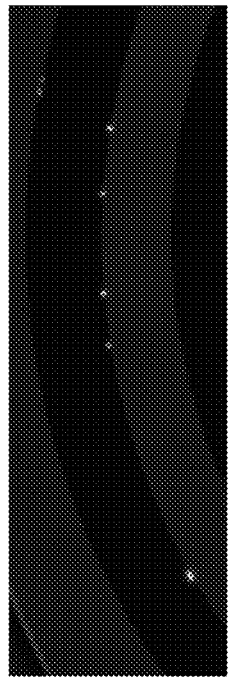
FIGS. 28A and 28B illustrate images of selective capture of bacterial species by tuning an electric field based on cross-over frequencies for different bacterial species in accordance with some embodiments.
Figure 28B:
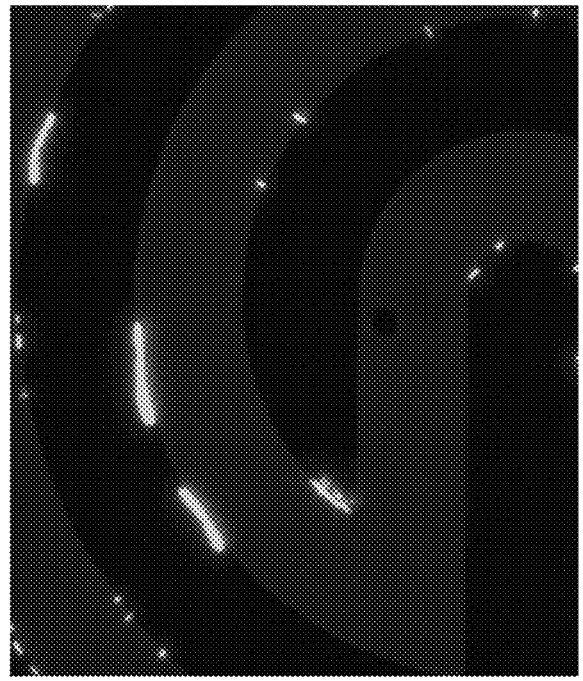
Figure 28A:
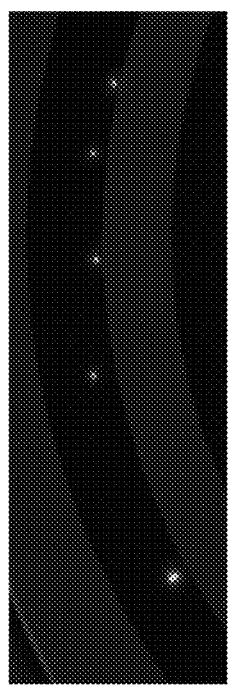
Figure 28A:
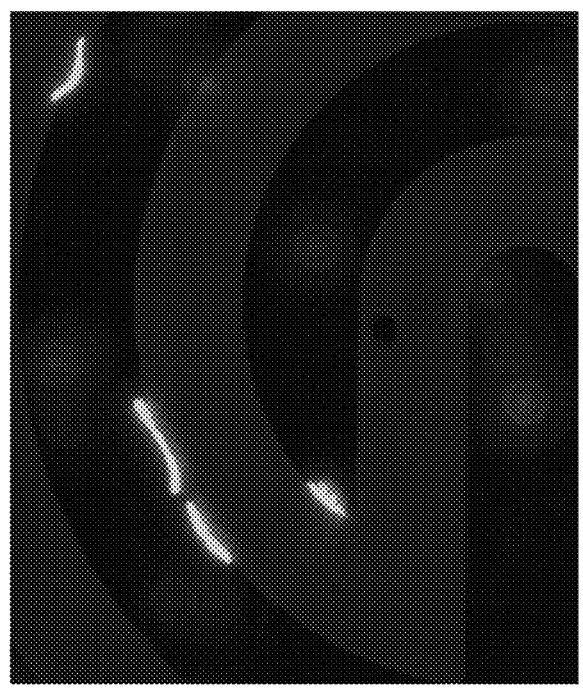

FIGS. 28A and 28B illustrate images showing selective capture of *B. megaterium* (shown as long strands) from *E. coli* (shown as dots). FIG. 28A illustrates an image taken when the frequency of the electric field is 50 Vpp and 90 MHz tuned to capture only *B. megaterium* but not *E. coli*, which is out of focus. FIG. 28B illustrates an image taken when the frequency of the electric field is 50 Vpp and 20 MHz tuned to capture both *B. megaterium* and *E. coli*.

Figure 29A:
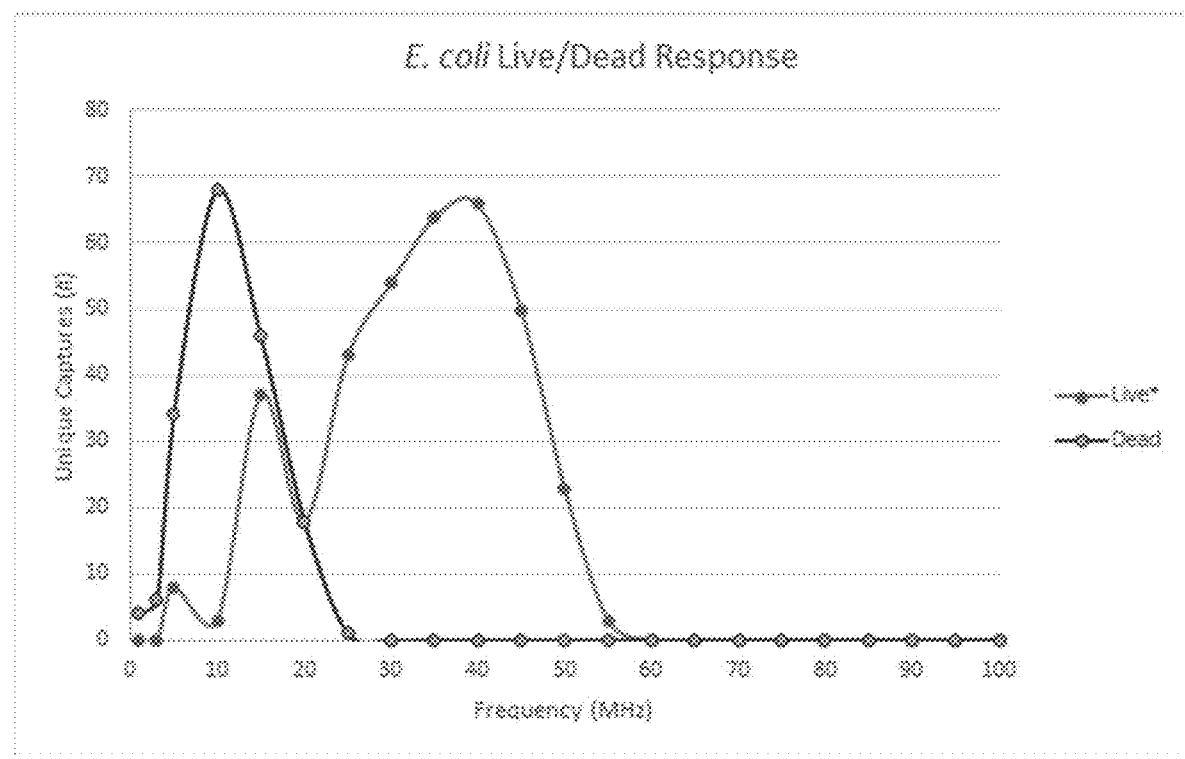
FIGS. 29A and 29B illustrate plots showing viability of bacteria following capture and release using some embodiments.
Figure 29B:
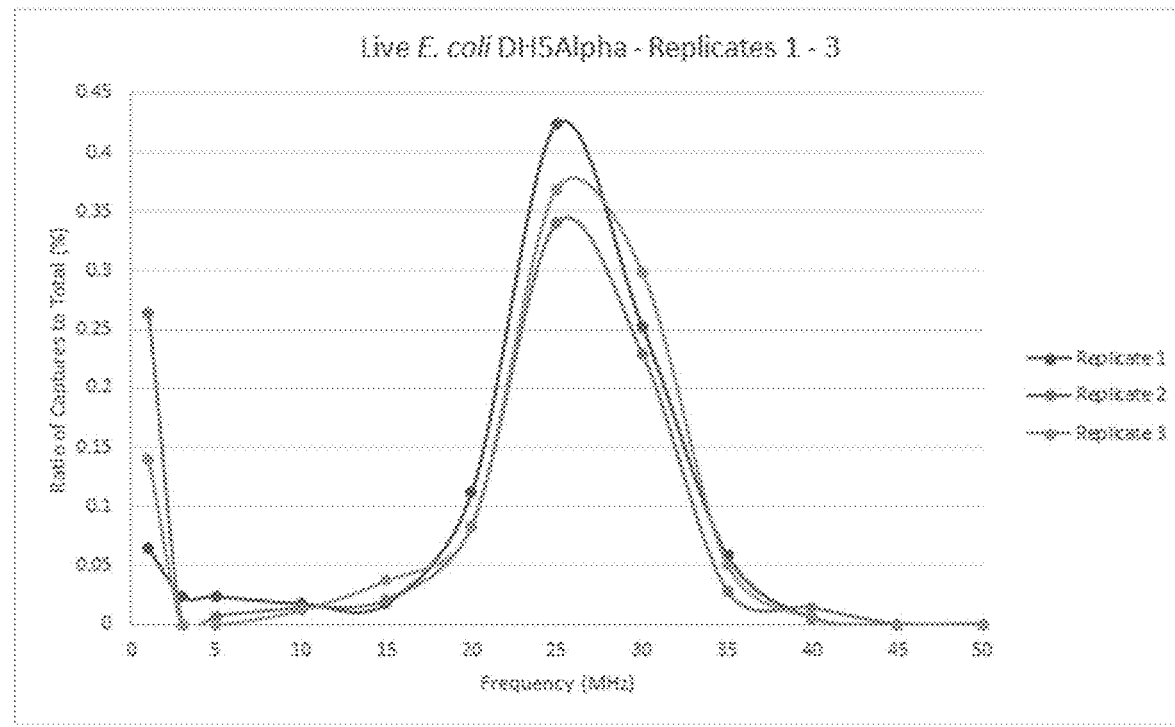

Bacteria detected in samples using stain-based methods or molecular methods are no longer viable. By contrast, the inventors have recognized that detection of bacteria using one or more of the techniques described herein (e.g., using dielectrophoresis capture) yields viable bacteria following their capture (i.e., capture of the bacteria does not kill the bacteria). Accordingly, some embodiments relate to methods and apparatus for detection and separation of bacteria from a sample that remain viable. FIG. 29A shows that live vs. dead *E. coli* bacteria respond differently to an electric field indicating that live and dead bacteria in a sample may be separated by tuning the frequency of the electric field to a frequency of maximal capture. For instance, dead bacteria show a peak response for capture around 10 MHz with essentially no capture above 25 MHz, whereas live bacteria show a peak response for capture around 40 MHz. Accordingly, to capture only live bacteria, the applied electric field may be tuned to a frequency above 25 MHz, which would result in capture of the live bacteria, while dead bacteria would not be captured. FIG. 29B shows results of testing multiple replicates of live bacteria showing a consistent peak response of capture around 25 MHz.

In a viability experiment, it was demonstrated that *B. cereus* suspended in a tested buffer (PBS 1:1000 in deionized water) without staining with SybrGreen I is efficiently captured on a microfluidic chip designed in accordance with the techniques describe herein when the electric field was on. The tested buffer flowing through the chip was collected and plated on selected agar pates to calculate capture efficiency of the system. Bacteria captured on the electrodes were flushed with the tested buffer solution while the electric field was still on. The electric field was then turned off and the bacteria released from the electrodes were collected and plated on agar plates to calculate release efficiency and to confirm viability. The results of the experiment are shown in FIG. 30, which demonstrate that more that 60% of the bacteria captured on the microfluidic chip and then release remained viable after release.

Figure 31:
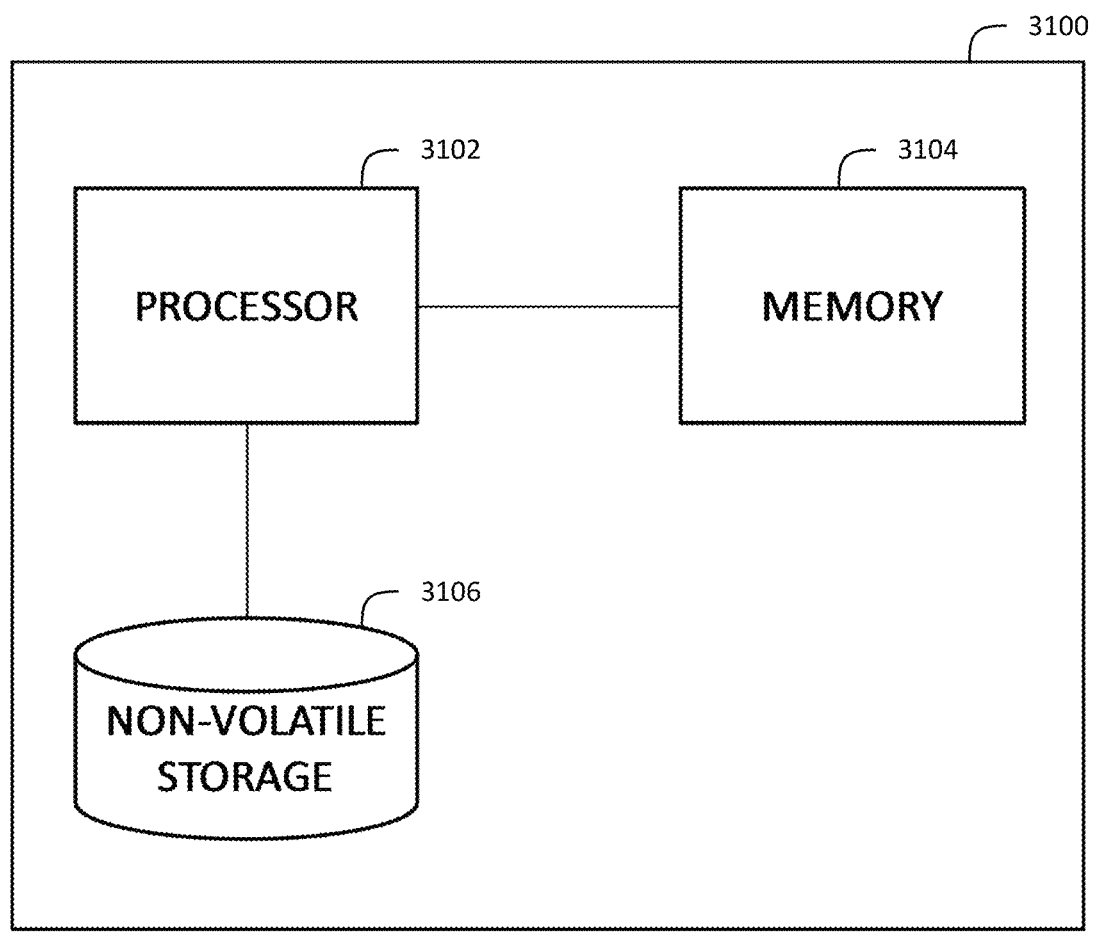
FIG. 31 illustrates a schematic of a computing system that may be used in accordance with some embodiments.

FIG. 31 shows a block diagram of an example computer system 3100 that may be used to implement embodiments of the technology described herein. The computing system 3100 may include one or more computer hardware processors 3102 and non-transitory computer-readable storage media (e.g., memory 3104 and one or more non-volatile storage devices 3106). The processor(s) 3102 may control writing data to and reading data from (1) the memory 3104; and (2) the non-volatile storage device(s) 3106. To perform any of the functionality described herein, the processor(s) 3102 may execute one or more processor-executable instructions stored in one or more non-transitory computer-readable storage media (e.g., the memory 3104), which may serve as non-transitory computer-readable storage media storing processor-executable instructions for execution by the processor(s) 3102.

Having thus described several aspects and embodiments of the technology set forth in the disclosure, it is to be appreciated that various alterations, modifications, and improvements will readily occur to those skilled in the art. For example, while aspects of the present technology relate to an apparatus and methods for detection, separation, purification, and/or quantification of bacteria as described herein, the inventors have recognized that such apparatus and methods are broadly applicable to other organisms of interest, e.g. viruses, yeast, and aspects of the technology are not limited in this respect.

Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The above-described embodiments of the present technology can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated. that any component or collection of components that perform the functions described above can be generically considered as a controller that controls the above-described function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The terms "substantially", "approximately", and "about" may be used to mean within ±20% of a target value in some embodiments, within ±10% of a target value in some embodiments, within ±5% of a target value in some embodiments, within ±2% of a target value in some embodiments. The terms "approximately" and "about" may include the target value.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The invention claimed is:

1. A bacterial separation system configured to separate live organisms from dead organisms in a fluid sample, the system comprising:
 a microfluidic device including:
  a microfluidic passage configured to receive the sample at an inlet of the microfluidic passage; and at least one electrode system comprising a first electrode system disposed adjacent to a first portion of the microfluidic passage and a second electrode system disposed adjacent to a second portion of the microfluidic passage;

at least one signal generator electrically connected to the at least one electrode system and configured to:

generate a first AC voltage to drive the first electrode system, the first AC voltage having first characteristics that causes the first electrode system to generate a first electric field configured to selectively capture only the live organisms on a surface of at least one first electrode in the first electrode system via positive dielectrophoresis, and generate a second AC voltage to drive the second electrode system, the second AC voltage having second characteristics that causes the second electrode system to generate a second electric field configured to selectively capture only the dead organisms on a surface of at least one second electrode in the second electrode system via positive dielectrophoresis;

an optical system configured to image the at least one first electrode while the live organisms are captured on the surface of the at least one first electrode and/or to image the at least one second electrode while the dead organisms are captured on the surface of the at least one second electrode; and a computer configured to:

process one or more images captured by the optical system to detect and/or quantify the live organisms in the one or more images; and/or process the one or more images captured by the optical system to detect and/or quantify the dead organisms in the one or more images.

2. The bacterial separation system of claim 1, further comprising:

a pump configured to pump the fluid sample from the inlet of the microfluidic passage to an outlet of the microfluidic passage.

3. The bacterial separation system of claim 2, wherein the pump is coupled to the inlet of the microfluidic passage.

4. The bacterial separation system of claim 2, wherein the pump is coupled to the outlet of the microfluidic passage.

5. The bacterial separation system of claim 1, wherein a frequency of the second AC voltage is less than a frequency of the first AC voltage.

6. The bacterial separation system of claim 5, wherein the frequency of the first AC voltage is greater than or equal to 25 MHz.

7. The bacterial separation system of claim 1, wherein the optical system is configured to image the first electrode system during capture of the live organisms and to image the second electrode system during capture of the dead organisms.

8. The bacterial separation system of claim 1, wherein;

the first electrode system comprises an array of first electrodes arranged in at least one dimension along the first portion of the microfluidic passage; and the second electrode system comprises an array of second electrodes arranged in the at least one dimension along the second portion of the microfluidic passage.

9. The bacterial separation system of claim 8, wherein each of the array of first electrodes and the array of second electrodes is arranged in at least two dimensions along the microfluidic passage.

10. The bacterial separation system of claim 1, wherein the at least one signal generator is further configured to:

generate, following capture of the live organisms, a third AC voltage to drive the first electrode system to produce a third electric field having third characteristics within the first portion of the microfluidic passage, wherein the third characteristics are selected such that the third electric field exerts a negative dielectrophoresis force on the captured live organisms sufficient to release the captured live organisms from the at least one first electrode in the first electrode system.

11. The bacterial separation system of claim 10, further comprising:

a container configured to collect at an outlet of the microfluidic passage, a fluid comprising the live organisms released from the at least one first electrode.

12. The bacterial separation system of claim 10, wherein the at least one signal generator is further configured to:

generate, following capture of the dead organisms, a fourth AC voltage to drive the second electrode system to produce a fourth electric field having fourth characteristics within the second portion of the microfluidic passage, wherein the fourth characteristics are selected such that the fourth electric field exerts a negative dielectrophoresis force on the captured dead organisms sufficient to release the captured dead organisms from the at least one second electrode in the second electrode system.

13. The bacterial separation system of claim 1, wherein the live organisms comprise live bacteria.

14. A bacterial separation system configured to separate live organisms from dead organisms in a fluid sample, the system comprising:

a microfluidic device including:

a microfluidic passage configured to receive the sample at an inlet of the microfluidic passage; and at least one electrode system disposed adjacent to the microfluidic passage, wherein the at least one electrode system includes only a single electrode system comprising at least one electrode;

at least one signal generator electrically connected to the at least one electrode system and configured to generate at least one AC voltage to drive the at least one electrode system such that each electrode system of the at least one electrode system is driven by an AC voltage having characteristics that causes the electrode system to generate an electric field configured to capture the live organisms and/or the dead organisms on a surface of an electrode in the electrode system via positive dielectrophoresis;

an optical system configured to image the at least one electrode while the live organisms or the dead organisms are captured on the surface of the electrode; and a computer configured to:

process one or more images captured by the optical system to detect and/or quantify the live organisms in the one or more images; and/or process the one or more images captured by the optical system to detect and/or quantify the dead organisms in the one or more images, wherein the at least one signal generator is further configured to generate, during a first time period, a first AC voltage to drive the single electrode system, the first AC voltage having first characteristics that causes the single electrode system to selectively capture only the live organisms on the surface of the at least one electrode in the single electrode system via positive dielelectrophoresis.

15. The bacterial separation system of claim 14, wherein a frequency of the first AC voltage is 25 MHz or higher.

16. The bacterial separation system of claim 14, wherein the at least one signal generator is further configured to generate, during a second time period after the first time period, a second AC voltage to drive the single electrode system, the second AC voltage having second characteristics that causes the single electrode system to release the live organisms from the surface of the at least one electrode in the single electrode system via negative dielelectrophoresis.

17. A bacterial separation system configured to separate live organisms from dead organisms in a fluid sample, the system comprising:
  a microfluidic device including:
    a microfluidic passage configured to receive the sample at an inlet of the microfluidic passage; and
    at least one electrode system disposed adjacent to the microfluidic passage, wherein the at least one electrode system includes only a single electrode system comprising at least one electrode;
  at least one signal generator electrically connected to the at least one electrode system and configured to generate at least one AC voltage to drive the at least one electrode system such that each electrode system of the at least one electrode system is driven by an AC voltage having characteristics that causes the electrode system to generate an electric field configured to capture the live organisms and/or the dead organisms on a surface of an electrode in the electrode system via positive dielelectrophoresis;
  an optical system configured to image the at least one electrode while the live organisms or the dead organisms are captured on the surface of the electrode; and
  a computer configured to:
    process one or more images captured by the optical system to detect and/or quantify the live organisms in the one or more images; and/or
    process the one or more images captured by the optical system to detect and/or quantify the dead organisms in the one or more images,
  wherein the at least one signal generator is further configured to generate, during a first time period, a first AC voltage to drive the single electrode system, the first AC voltage having first characteristics that causes the single electrode system to capture both the live organisms and the dead organisms on the surface of the at least one electrode in the single electrode system via positive dielelectrophoresis.

18. The bacterial separation system of claim 17, wherein the at least one signal generator is further configured to generate, during a second time period after the first time period, a second AC voltage to drive the single electrode system, the second AC voltage having second characteristics that causes the single electrode system to selectively release either the live organisms or the dead organisms from the surface of the at least one electrode in the single electrode system via negative dielelectrophoresis.

19. The bacterial separation system of claim 14, wherein; the at least one electrode comprises an array of electrodes arranged in at least one dimension along the microfluidic passage.

20. The bacterial separation system of claim 19, wherein the array of electrodes is arranged in at least two dimensions along the microfluidic passage.

* * * * *